(12) United States Patent
Bouillon et al.

(10) Patent No.: US 7,888,338 B2
(45) Date of Patent: Feb. 15, 2011

(54) 7-(2-CYCLOHEXYLIDENE-ETHYLIDENE)-SPIRO[4.5]DECANES

(75) Inventors: Roger Bouillon, Winksele (BE); Pierre De Clercq, Gent (BE); Wim Schepens, Wetteren (BE); Maurits Vandewalle, Gent (BE); Annemieke Verstuyf, Oud-Heverlee (BE)

(73) Assignees: K.U. Leuven Research & Development, Leuven (BE); Universiteit Gent, Gent (BE)

( * ) Notice: Subject to any disclaimer, the term of this patent is extended or adjusted under 35 U.S.C. 154(b) by 1326 days.

(21) Appl. No.: 11/295,000

(22) Filed: Dec. 6, 2005

(65) Prior Publication Data

US 2006/0178350 A1 Aug. 10, 2006

Related U.S. Application Data

(60) Provisional application No. 60/633,670, filed on Dec. 6, 2004.

(51) Int. Cl.
*A61K 31/59* (2006.01)
*C07C 401/00* (2006.01)

(52) U.S. Cl. ...................................... 514/167; 552/653

(58) Field of Classification Search .................. 514/167; 552/653
See application file for complete search history.

(56) References Cited

U.S. PATENT DOCUMENTS

| 5,283,197 | A | 2/1994 | Robins |
| 5,395,830 | A | 3/1995 | Deluca et al. |
| 7,704,986 | B2 * | 4/2010 | Bouillon et al. ............. 514/183 |

OTHER PUBLICATIONS

Schepens et al., "Synthesis and biological activity of 22-oxa CD-ring modified analogues of 1α, 25-dihydroxyvitamin $D_3$: spiro[5.5]undecane CF-ring analogues," *Bioorg. Med. Chem. Lett.* 14:3889-3892 (2004).
Office Action for U.S. Appl. No. 11/295,007 mailed on Oct. 23, 2006.
International Search Report mailed May 10, 2006 (PCT/BE2005/000180).

* cited by examiner

*Primary Examiner*—Sabiha Qazi
(74) *Attorney, Agent, or Firm*—Clark & Elbing LLP

(57) ABSTRACT

The present invention relates to 7-(2-cyclohexylidene-ethylidene)-spiro[4.5]-decanes, compositions which comprise said 7-(2-cyclohexylidene-ethylidene)-spiro[4.5]-decanes, and methods for treating diseases, illnesses, and the like with said 7-(2-cyclohexylidene-ethylidene)-spiro[4.5]decanes.

21 Claims, No Drawings

7-(2-CYCLOHEXYLIDENE-ETHYLIDENE)-SPIRO[4.5]DECANES

CROSS REFERENCE TO RELATED APPLICATIONS

This application claims priority under Title 35, United States Code 119(e) from Provisional Application Ser. No. 60/633,670, filed Dec. 6, 2004, which is hereby incorporated by reference.

FIELD OF THE INVENTION

The present invention relates to 7-(2-cyclohexylidene-ethylidene)-spiro[4.5]-decanes, compositions which comprise said 7-(2-cyclohexylidene-ethylidene)-spiro[4.5]-decanes, and methods for treating diseases, illnesses, and the like with said 7-(2-cyclohexylidene-ethylidene)-spiro[4.5]decanes.

DETAILED DESCRIPTION OF THE INVENTION

The present invention addresses several unmet medical needs, inter alia:

1) Providing compositions effective against diseases affected by cell proliferation, cell differentiation or related to calcium and phosphate or bone homeostasis disorders, inter alia, osteomalacia, osteoporosis, renal osteodystrophy, and disorders of the parathyroid function.

2) Providing compositions effective against diseases affected by immune disorders:

i) auto-immune diseases, inter alia, diabetes mellitus type 1, multiple sclerosis, lupus and lupus like disorders, asthma, glomerulonephritis, and auto-immune thyroidis;

ii) selective dysfunctions of the immune system, inter alia, Acquired Immune Deficiency Syndrome (AIDS);

iii) medically induced immune disorders, inter alia, the body's rejection of foreign tissue due to tissue grafts (e.g. kidney, heart, bone marrow, liver, islets or whole pancreas, and skin);

iv) autoimmune and other inflammatory diseases, inter alia, rheumatoid arthritis; and v) skin disorders, inter alia, those characterized by hyperproliferation, inflammation and (auto)immune reactions, for example psoriasis, dyskeratosis, and acne.

3) Providing compositions effective against diseases affected by cell proliferation disorders such as cancer, for example, breast cancer, leukemia, myelo-dysplastic syndromes and lymphomas, squamous cell carcinomas and gastrointestinal cancers, melanomas, and osteosarcoma.

The following chemical hierarchy is used throughout the specification to describe and enable the scope of the present invention and to particularly point out and distinctly claim the units which comprise the compounds of the present invention. The term "hydrocarbyl" stands for any carbon atom-based unit (organic molecule), said units optionally containing one or more heteroatoms such as, but not limited to, oxygen, nitrogen or sulfur and/or containing one or more organic functional groups, including inorganic atom comprising salts, inter alia, carboxylate salts, quaternary ammonium salts and the like. Encompassed within the term "hydrocarbyl" are the terms "acyclic" and "cyclic" units which divide hydrocarbyl units into cyclic and non-cyclic classes.

A. Substituted and unsubstituted $C_1$-$C_{20}$ acyclic hydrocarbyl:

For the purposes of the present invention the term "substituted and unsubstituted $C_1$-$C_{20}$ acyclic hydrocarbyl" encompasses 3 categories of units:

1) $C_1$-$C_{20}$ linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted $C_1$-$C_{20}$ linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.

2) $C_2$-$C_{20}$ linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted $C_2$-$C_{20}$ linear or branched alkenyl, non-limiting examples of which includes, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

3) $C_2$-$C_{20}$ linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted $C_2$-$C_{20}$ linear or branched alkynyl, non-limiting examples of which includes, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

For the purposes of the present invention the term "substituted and unsubstituted $C_1$-$C_{20}$ acyclic hydrocarbyl" also includes groups optionally containing one or more heteroatoms such as, but not limited to, oxygen, nitrogen or sulfur in the $C_1$-$C_{20}$ alkyl portion, respectively the $C_2$-$C_{20}$ alkenyl portion or $C_2$-$C_{20}$ alkynyl portion, of said groups.

B. Substituted and unsubstituted $C_3$-$C_{20}$ cyclic hydrocarbyl:

For the purposes of the present invention the term "substituted and unsubstituted $C_3$-$C_{20}$ cyclic hydrocarbyl" encompasses 5 categories of units:

1) The term "carbocyclic" is defined herein as "encompassing rings comprising from 3 to 20 carbon atoms as the only atoms in the rings, wherein each ring can be independently substituted with one or more moieties capable of replacing one or more hydrogen atoms." The following are non-limiting examples of "substituted and unsubstituted $C_3$-$C_{20}$ carbocyclic rings" which encompass the following categories of units:

i) carbocyclic rings having a single substituted or unsubstituted, saturated or ethylenically unsaturated, hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxy-cyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), decalinyl ($C_{10}$), 2-methylcyclopropyl ($C_3$), 2,5-dimethylcyclopentyl ($C_5$), 4-tert-butyl-cyclopentyl ($C_5$), 3,5-dichloro-cyclohexyl ($C_6$), 4-hydroxycyclohexyl ($C_6$), and 3,3,5-trimethylcyclohex-1-enyl ($C_9$).

ii) carbocyclic rings having two or more substituted or unsubstituted fused hydrocarbon rings, non-limiting examples of which include, octahydro-pentalenyl ($C_8$), octahydro-1H-indenyl ($C_9$), 3a,4,5,6,7,7a-hexahydro-3H-inden-4-yl ($C_9$), decahydroazulenyl ($C_{10}$); bicyclo[6.2.0]decanyl ($C_{10}$), 1,2,3,4,4a,5,8,8a-octahydro-naphthalenyl ($C_{10}$), and dodecahydro-1H-fluorenyl ($C_{13}$).

iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]-undecanyl.

2) The term "aryl" is defined herein as "units encompassing at least one phenyl or naphthyl ring with no other rings containing a heteroatom as part of the ring, wherein each ring can be independently substituted with one or more moieties capable of replacing one or more hydrogen atoms." The following are non-limiting examples of "substituted and unsubstituted $C_6$-$C_{14}$ aryl rings" which encompass the following categories of units:

i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), 6-methyl-carboxynaphthylen-2-yl ($C_{10}$), 6-cyano-naphthylen-1-yl ($C_{10}$), 4-biphenyl ($C_{12}$), 4'-flouro-4-biphenyl ($C_{12}$), 3',5'-dicyano-4-biphenyl ($C_{12}$), 4'-chloro-3-biphenyl ($C_{12}$), and 4-phenylnaphthylen-1-yl ($C_{14}$).

ii) $C_6$ or $C_{10}$ aryl rings fused with 1 or 2 saturated carbocyclic rings, non-limiting examples of which include bicyclo[4.2.0]octa-1,3,5-trienyl ($C_8$), indanyl ($C_9$), 1H-indenyl ($C_9$), 1,2,3,4-tetrahydronaphthalenyl ($C_{10}$), 1,2-dihydronaphthalenyl ($C_{10}$), 1,4-dihydronaphthalenyl ($C_{10}$), acenaphthenyl ($C_{12}$), 2,3-dihydro-1H-phenalenyl ($C_{13}$), 1,2,3,4-tetrahydrophenanthrenyl ($C_{14}$), and 1,2,3,4-tetrahydroantracenyl ($C_{14}$).

3) The term "heterocyclic" is defined herein as "encompassing non-aromatic rings comprising from 3 to 20 atoms wherein at least one atom in at least one ring is a heteroatom independently chosen from nitrogen (N), oxygen (O) and sulfur (S), wherein each ring can be independently substituted with one or more moieties capable of replacing one or more hydrogen atoms." The following are non-limiting examples of "substituted and unsubstituted $C_3$-$C_{20}$ heterocyclic rings" which encompass the following categories of units:

i) heterocyclic units having a single ring containing one or more heteroatoms, non-limiting examples of which include, 1,2,3,4-tetrazolyl ($C_1$), diazirinyl ($C_1$), aziridinyl ($C_2$), [1,2,3]triazolyl ($C_2$), [1,2,4]triazolyl ($C_2$), urazolyl ($C_2$), oxazolyl ($C_3$), azetidinyl ($C_3$), pyrazolidinyl ($C_3$), imidazolidinyl ($C_3$), oxazolidinyl ($C_3$), isoxazolinyl ($C_3$), oxazolyl ($C_3$) isoxazolyl ($C_3$), thiazolidinyl ($C_3$), thiazolyl ($C_3$), imidazol-idinonyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), tetrahydrothiopenyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$).

ii) heterocyclic units having two or more rings, at least one of which is a heterocyclic ring and at least one of which is a carbocyclic or aryl ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1H-indolyl ($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more rings comprising from 5 to 20 atoms wherein at least one atom in at least one ring is a heteroatom independently chosen from nitrogen (N), oxygen (O) and sulfur (S), and at least one ring containing a heteroatom is an aromatic ring, wherein each ring can be independently substituted with one or more moieties capable of replacing one or more hydrogen atoms." The following are non-limiting examples of "substituted and unsubstituted $C_5$-$C_{20}$ heteroaryl rings" which encompass the following categories of units:

i) heteroaryl rings containing a single ring, non-limiting examples of which include, triazinyl ($C_3$), thiazyl ($C_3$), 1H-imidazoyl ($C_3$), furanyl ($C_4$), thiophenyl ($C_4$), pyrimidinyl ($C_4$), 2-phenylpyrimidinyl ($C_4$), pyridinyl ($C_5$), 3-methylpyridinyl ($C_5$), and 4-dimethylamino-pyridinyl ($C_5$)

ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 4,5,6,7-tetrahydro-1-H-indolyl ($C_8$), quinoxalinyl ($C_8$), 5-methylquinoxalinyl ($C_8$), quinazolinyl ($C_8$), 6,7-dihydro-5H-[1]pyridine ($C_8$), quinolinyl ($C_9$), n8-hydroxyquinolinyl ($C_9$), isoquinolinyl ($C_9$), and phenyanthridinyl ($C_{13}$).

5) $C_1$-$C_{12}$ tethered $C_3$-$C_{20}$ cyclic hydrocarbyl units (whether $C_3$-$C_{20}$ carbocyclic units, $C_6$-$C_{14}$ aryl units, $C_3$-$C_{20}$ heterocyclic units, or $C_5$-$C_{20}$ heteroaryl units, all of them as defined hereinabove), i.e. $C_3$-$C_{20}$ cyclic hydrocarbyl units which are connected to another moiety, unit, or core of the molecule by way of a substituted and unsubstituted $C_1$-$C_{12}$ alkylene linking unit. Non-limiting examples of tethered $C_3$-$C_{20}$ cyclic hydrocarbyl units include benzyl $C_1$—($C_6$) having the formula:

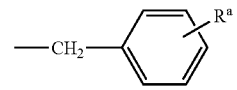

wherein multiple $R^a$ can be present and $R^a$ is (are) optionally one or more independently chosen substitutions for hydrogen. Further examples include other aryl units, inter alia, (2-hydroxy-phenyl)hexyl $C_6$—($C_6$); naphthalen-2-yl-methyl $C_1$—($C_{10}$), 4-fluorobenzyl $C_1$—($C_6$), 2-(3-hydroxy-phenyl)ethyl $C_2$—($C_6$), as well as substituted and unsubstituted $C_1$-$C_{12}$ alkylenecarbocyclic units, for example cyclopropylmethyl $C_1$—($C_3$), cyclopentyl-ethyl $C_2$—($C_5$), cyclohexylmethyl $C_1$—($C_6$) and the like; included within this category are substituted and unsubstituted $C_1$-$C_{12}$ alkylene-heteroaryl units, for example a 2-picolyl $C_1$—($C_6$) unit having the formula:

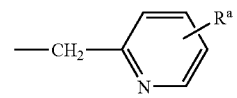

wherein $R^a$ is (are) the same as defined above. In addition, $C_1$-$C_{12}$ tethered $C_3$-$C_{20}$ cyclic hydrocarbyl units include $C_1$-$C_{12}$ alkylene-heterocyclic units, non-limiting examples of which include, aziridinylmethyl $C_1$—($C_2$) and oxazol-2-ylmethyl $C_1$—($C_3$).

For the purpose of the present invention fused ring units, as well as spirocyclic rings, bicyclic rings and the like, which comprise a single heteroatom not being a part of an aromatic ring, such as but not limited to 1,2,3,4-tetrahydroquinoline, 6,7-dihydro-5H-cyclopenta[b]pyridine and the like, will be considered to be encompassed with the definition of "heterocyclic ring."

When a fused ring unit contains heteroatoms in both a saturated and an aromatic ring, the aromatic ring will predominate and determine the type of category to which the ring is assigned. For example, 1,2,3,4-tetrahydro-[1,8]naphthyridine is, for the purpose of the present invention, encompassed under the term "heteroaryl unit."

The term "substituted" is used throughout the specification. The term "substituted" is defined herein as "a hydrocarbyl moiety, whether acyclic or cyclic, which has one or more hydrogen atoms replaced by a substituent or several substituents as defined herein below. The units, which substituted for hydrogen atoms are capable of replacing one hydrogen atom, two hydrogen atoms, or three hydrogen atoms of one carbon atom in a hydrocarbyl moiety or of a hydrocarbyl moiety at a time. Even more hydrogen atoms of a hydrocarbyl moiety can be changed at a time, such as 4, 5, 6, or even more. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aryl", (N,N-dimethyl-5-amino)octanyl is a substituted $C_8$ alkyl unit, 3-guanidinopropyl is a "substituted $C_3$ alkyl unit" and 2-carboxypyridinyl is a "substituted heteroaryl unit."

The following are non-limiting examples of categories and, examples herewith of units which can suitably and independently substitute for hydrogen atoms on a cyclic or acyclic hydrocarbyl unit, wherein $R^{30}$ may be selected from the group consisting of hydrogen, $C_1$-$C_{10}$ linear or branched alkyl, $C_2$-$C_{10}$ linear or branched alkenyl, $C_2$-$C_{10}$ linear or branched alkynyl, $C_3$-$C_{20}$ heterocyclic, $C_5$-$C_{20}$ heteroaryl and $C_6$-$C_{14}$ aryl.

i) —NHCOR$^{30}$; for example, —NHCOCH$_3$, —NHCOCH$_2$CH$_3$, —NHCOC$_6$H$_5$;
ii) —COR$^{30}$; for example, —COCH$_3$, —COCH$_2$CH$_3$, —COCH$_2$CH$_2$CH$_3$;
iii) —CO$_2$R$^{30}$; for example, —CO$_2$CH$_3$, —CO$_2$CH$_2$CH$_3$, —CO$_2$CH$_2$CH$_2$CH$_3$;
iv) —OCOR$^{30}$; for example, —OCOCH$_3$, —OCOCH$_2$CH$_3$, —OCOCH$_2$CH$_2$CH$_3$;
v) —C(=NH)NH$_2$;
vi) —NHC(=NH)NH$_2$;
vii) —N(R$^{30}$)$_2$; for example, —NH$_2$, —NHCH$_3$, —N(CH$_3$)$_2$, —NH(CH$_2$CH$_3$);
viii) —NHC$_6$H$_5$;
ix) =CHC$_6$H$_5$;
x) —CON(R$^{30}$)$_2$; for example, —CONH$_2$, —CONHCH$_3$, —CON(CH$_3$)$_2$;
xi) —CONHNH$_2$;
xii) —NHCN;
xiii) —OCN;
xiv) —CN;
xv) halogen: F, Cl, Br, and I;
xvi) —NHN(R$^{30}$)$_2$; for example, —NHNH$_2$, —NHNHCH$_3$, —NHN(CH$_3$)$_2$;
xvii) —OR$^3$; for example, —OH, —OCH$_3$, —OCH$_2$CH$_3$, —OCH$_2$CH$_2$CH$_3$;
xviii) —NO$_2$;
xix) —CH$_m$X$_n$; wherein X is halogen, the index m can be selected from 0, 1 and 2, the index n can be selected from 0, 1, 2 and 3, and m+n=3; for example, —CF$_3$, —CCl$_3$, —CBr$_3$;
xx) —SO$_2$R$^{30}$; for example, —SO$_2$CH$_3$, —SO$_2$CH$_2$CH$_3$, —SO$_2$C$_6$H$_5$;
xxi) —OSO$_2$R$^{30}$; for example, —OSO$_2$CH$_3$, —OSO$_2$CH$_2$CH$_3$, —OSO$_2$C$_6$H$_5$;
xxii) —OSO$_3$R$^{30}$; for example, —OSO$_3$CH$_3$, —OSO$_3$C$_6$H$_5$;
xxiii) —SO$_2$N(R$^{30}$)$_2$; for example, —SO$_2$NH$_2$; —SO$_2$NHCH$_3$; —SO$_2$NHC$_6$H$_5$;
xxiv) =O;
xxv) =NR$^{30}$; for example, =NH, =NCH$_3$, =NCH$_2$CH$_3$,
xxvi) $C_1$-$C_{20}$ acyclic hydrocarbyl;
xxvii) $C_3$-$C_{20}$ cyclic hydrocarbyl;
xxviii) two hydrogen atoms on adjacent carbon atoms are substituted by a single oxygen atom, thereby forming an epoxy unit; and
xxix) two hydrogen atoms on non-adjacent carbon atoms are substituted to form a $C_3$-$C_{20}$ cyclic hydrocarbyl.

Compounds

The present invention relates to 7-[2-(substituted or unsubstituted cyclohexyl-idene)-ethylidene]-spiro[4.5]decanes the core scaffolds having two isomeric orientations with the formulae:

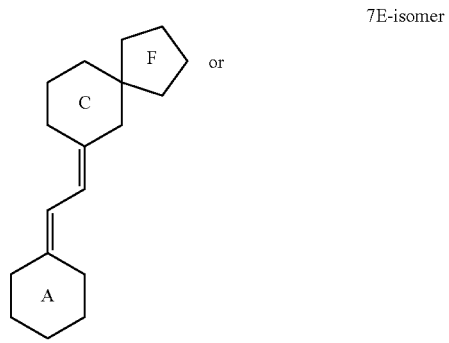

7E-isomer

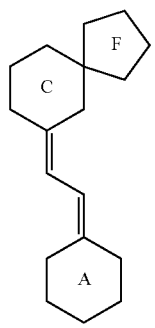

wherein the rings of said core scaffolds are designated "A", "C" and "F" as indicated and referred to as such herein.

The analogs of the present invention comprise an upper CF-Ring scaffold connected to a lower A-Ring scaffold as depicted herein below.

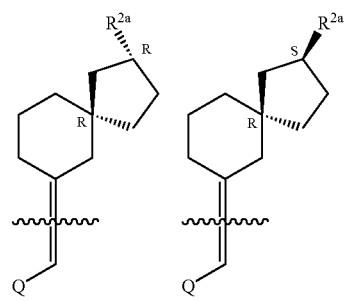

The present invention also utilizes the following numbering system when referring to the carbon atoms which comprise the core scaffold of the compounds of the present invention:

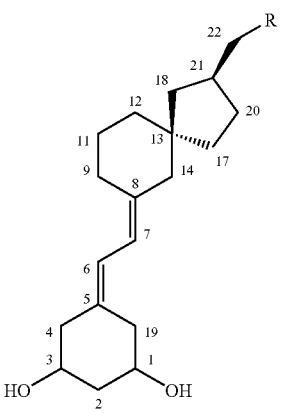

The upper CF-Ring scaffold can have the (S,S), (S,R), (R,R), and (R,S) stereochemistry at carbons 13, 20 and 21 as depicted herein below.

For compounds of the present invention wherein the F ring is mono-substituted, said compounds are named as shown in the following exemplary but non-limiting structural formula, utilizing the stereochemical assignments to delineate whether the substituent which is present is $R^{1a}$, $R^{1b}$, $R^{2a}$, or $R^{2b}$.

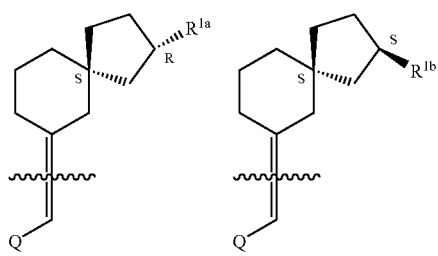

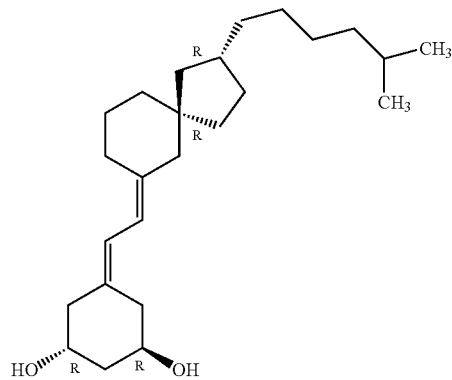

-continued

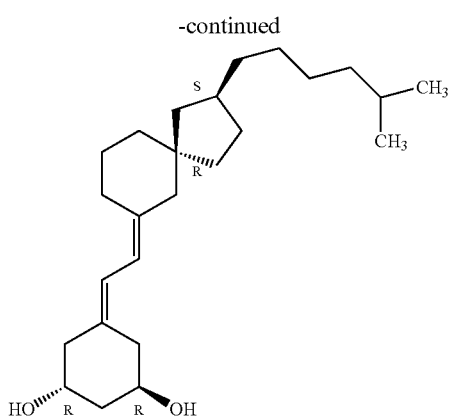

The compounds represented by the formulae above, are named (1R,3R)-5-{(E)-(2R,5R))-2-[2-(5-methylhexyl)-spiro[4.5]dec-7-ylidene]ethylidene}-cyclohexane-1,3-diol and (1R,3R)-5-{(E)-(2S,5R))-2-[2-(5-methylhexyl)-spiro[4.5]dec-7-ylidene]-ethylidene}-cyclohexane-1,3-diol respectively.

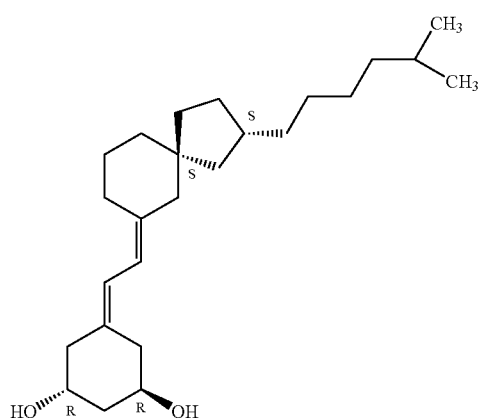

The compounds represented by the formulae above, are named (1R,3R)-5-{(E)-(2S,5S))-2-[2-(5-methylhexyl)-spiro[4.5]dec-7-ylidene]-ethylidene}-cyclohexane-1,3-diol and (1R,3R)-5-{(E)-(2R,5S))-2-[2-(5-methylhexyl)-spiro[4.5]dec-7-ylidene]-ethylidene}-cyclohexane-1,3-diol respectively.

The compounds of the present invention encompass both possible orientations as depicted by the following formulae wherein Q is the A ring system as described further herein below.

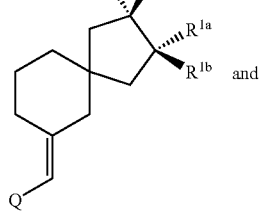

CF Rings Systems

The first category of CF Ring Systems relates to the (S,S) diastereomers having the formula:

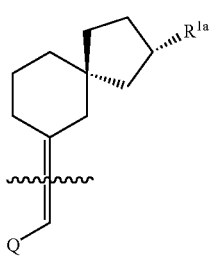

$R^{1a}$ is hydrogen or a $C_1$-$C_{20}$ substituted or unsubstituted, linear or branched hydrocarbyl unit.

The first aspect of $R^{1a}$ relates to unsubstituted $C_1$-$C_{10}$ linear or branched alkyl. Non-limiting examples of this first aspect of $R^{1a}$ include methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methylbutyl ($C_5$), 3-methylbutyl ($C_5$), 1,2-dimethylpropyl ($C_5$), 2,2-dimethylpropyl ($C_5$), n-hexyl ($C_6$), 1-methylpentyl ($C_6$), 2-methylpentyl ($C_6$), 3-methyl-pentyl ($C_6$), 4-methylpentyl ($C_6$), 1,1-dimethylbutyl ($C_6$), 1,2-dimethylbutyl ($C_6$), 1,3-dimethylbutyl ($C_6$), 2,2-dimethylbutyl ($C_6$), 2,3-dimethylbutyl ($C_6$), 3,3-dimethylbutyl ($C_6$), 1-ethylbutyl ($C_6$), 2-ethylbutyl ($C_6$), n-heptyl ($C_7$), 1-methylhexyl ($C_7$), 2-methyl-hexyl ($C_7$), 3-methylhexyl ($C_7$), 4-methylhexyl ($C_7$), 5-methylhexyl ($C_7$), 1,1-dimethyl-pentyl ($C_7$), 1,2-dimethylpentyl ($C_7$), 1,3-dimethylpentyl ($C_7$), 1,4-dimethylpentyl ($C_7$), 2,2-dimethylpentyl ($C_7$), 2,3-dimethylpentyl ($C_7$), 2,4-dimethylpentyl ($C_7$), 3,3-dimethyl-pentyl ($C_7$), 3,4-dimethylpentyl ($C_7$), and 4,4-dimethylpentyl ($C_7$).

The second aspect of $R^{1a}$ relates to substituted $C_1$-$C_4$ linear or branched alkyl wherein said substitution is preferably chosen from the group consisting of:
- i) —$OR^{30}$ wherein $R^{30}$ is as defined hereinabove; for example, —OH, —$OCH_3$, —$OCH_2CH_3$, —$OCH_2CH_2CH_3$;
- ii) halogen—fluoro, chloro, bromo, and iodo;
- iii) —$CH_mX_n$; wherein X is halogen, the index m is from 0 to 2, the index n is from 1 to 3, and m+n=3; for example, —$CH_2F$, —$CHF_2$, —$CF_3$, —$CH_2Cl$, —$CHCl_2$, —$CCl_3$, and —$CBr_3$; and
- iv) two hydrogens from adjacent carbon atoms are substituted by a single oxygen atom thereby forming an epoxy unit; for example but not limited to:

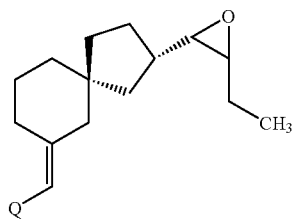

Non-limiting examples of this second aspect includes fluoromethyl, difluoromethyl, trifluoromethyl, hydroxymethyl, 2-hydroxyethyl, 2-hydroxy-2-methylpropyl, and 4-hydroxybutyl.

The third aspect of $R^{1a}$ relates to substituted $C_5$-$C_{20}$ linear or branched alkyl wherein said substitution is preferably chosen from the group consisting of:
- i) —$OR^{30}$ wherein $R^{30}$ is as defined hereinabove; for example, —OH, —$OCH_3$, —$OCH_2CH_3$, —$OCH_2CH_2CH_3$;
- ii) —$CH_mX_n$; wherein X is halogen, the index m is from 0 to 2, the index n is from 1 to 3, m+n=3; for example, —$CH_2F$, —$CHF_2$, —$CF_3$, —$CH_2Cl$, —$CHCl_2$, —$CCl_3$, and —$CBr_3$; and
- iii) two hydrogens from adjacent carbon atoms are substituted by a single oxygen atom thereby forming an epoxy unit; for example:

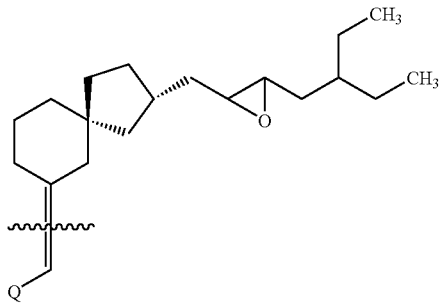

Non-limiting examples of this third aspect includes 1-hydroxy-4-methylpentan-1-yl ($C_6$); 2-hydroxy-4-methylpentan-1-yl ($C_6$); 3-hydroxy-4-methylpentan-1-yl ($C_6$); 4-hydroxy-4-methylpentan-1-yl ($C_6$); 1-hydroxy-5-methylhexan-2-yl ($C_7$); 2-hydroxy-5-methylhexan-2-yl ($C_7$); 3-hydroxy-5-methylhexan-2-yl ($C_7$); 4-hydroxy-5-methylhexan-2-yl ($C_7$); 5-hydroxy-5-methylhexan-2-yl ($C_7$); 1-hydroxy-6-methylheptan-2-yl ($C_8$); 2-hydroxy-6-methylheptan-2-yl ($C_8$); 3-hydroxy-6-methylheptan-2-yl ($C_8$); 4-hydroxy-6-methylheptan-2-yl ($C_8$); 5-hydroxy-6-methylheptan-2-yl ($C_8$); 1-hydroxy-1,5-dimethyl-hexan-1-yl; ($C_8$); 1-hydroxy-5,5-dimethyl-hexan-1-yl ($C_8$), 1-trifluoromethyl-4-methylpentan-1-yl ($C_6$); 2-trifluoro-methyl-4-methyl-pentan-1-yl ($C_6$); 3-trifluoromethyl-4-methylpentan-1-yl ($C_6$); 4-trifluoromethyl-4-methyl-pentan-1-yl ($C_6$); 1-trifluoromethyl-5-methylhexan-2-yl ($C_7$); 2-trifluoromethyl-5-methyl-hexan-2-yl ($C_7$); 3-trifluoromethyl-5-methylhexan-2-yl ($C_7$); 4-trifluoromethyl-5-methyl-hexan-2-yl ($C_7$); 5-trifluoromethyl-5-methylhexan-2-yl ($C_7$); 1-trifluoromethyl-6-methyl-heptan-2-yl ($C_8$); 2-trifluoro-methyl-6-methylheptan-2-yl ($C_8$); 3-trifluoromethyl-6-methylheptan-2-yl ($C_8$); 4-trifluoromethyl-6-methylheptan-2-yl ($C_8$); 5-trifluoromethyl-6-methylheptan-2-yl ($C_8$); and 1-trifluoromethyl-5,5-dimethylhexan-1-yl ($C_8$).

The fourth aspect of $R^{1a}$ relates to unsubstituted $C_2$-$C_{20}$ linear or branched alkenyl. Non-limiting examples of this fourth aspect include: 4-methylpent-2-enyl ($C_6$), 5-methylhex-2-enyl ($C_7$), 5-methylhex-3-enyl ($C_7$), 4-ethylhex-2-enyl ($C_8$), 6-methylhept-2-enyl ($C_8$), 6-methylhept-3-enyl ($C_8$), 6-methylhept-4-enyl ($C_8$), 7-methyloct-4-en-2-yl ($C_9$), 6-ethyloct-2-enyl ($C_{10}$), 6-ethyloct-3-enyl ($C_{10}$), and 6-ethyloct-4-enyl ($C_{10}$).

The fifth aspect of $R^{1a}$ relates to substituted $C_2$-$C_{20}$ linear or branched alkenyl. Non-limiting examples of this fifth aspect include: 4-hydroxy-4,4-bis-(trifluoro-methyl)but-2-enyl ($C_4$), 4-hydroxy-4-methylpent-2-enyl ($C_6$), 4-cyano-4-methylpent-2-enyl ($C_6$), 5-hydroxy-5-methylhex-2-enyl ($C_7$), 5-hydroxy-5-methylhex-3-enyl ($C_7$), 4-hydroxy-4-ethylhex-2-enyl ($C_8$), 6-hydroxy-6-methylhept-2-enyl ($C_8$), 6-hydroxy-6-methylhept-3-enyl ($C_8$), 6-hydroxy-6-methylhept-4-enyl ($C_8$), 7-hydroxy-7-methyloct-4-en-2-yl ($C_9$), 7-hydroxy-7-methyloct-3,5-dien-2-yl ($C_9$), 6-hydroxy-6-ethyloct-2-enyl ($C_{10}$), 6-hydroxy-6-ethyloct-3-enyl ($C_{10}$), 6-hydroxy-6-ethyloct-4-enyl ($C_{10}$), and 7-hydroxy-7-ethylnon-3,5-dien-2-yl ($C_{11}$), The sixth aspect of $R^{1a}$ relates $C_2$-$C_{20}$ linear or branched alkynyl. Non-limiting examples of this aspect include: pent-2-ynyl ($C_5$), hex-2-ynyl ($C_6$), hex-3-ynyl ($C_6$), hex-3-yn-2-yl ($C_6$), hex-4-yn-2-yl ($C_6$), 5-methylhex-3-ynyl ($C_7$), 6-methylhept-3-yn-2-yl ($C_8$), 5-ethylhept-3-ynyl ($C_9$), and 6-ethyloctyn-4-yn-2-yl ($C_{10}$).

The seventh aspect of $R^{1a}$ relates to substituted $C_2$-$C_{20}$ linear or branched alkynyl. Non-limiting examples of this seventh aspect include: 5-hydroxy-5-methylhex-3-ynyl ($C_7$), 4-(2-methyl-oxyranyl)-but-3-ynyl ($C_7$), 6-hydroxy-6-methylhept-3-yn-2-yl ($C_8$), 5-(2-methyl-oxyranyl)-pent-4-yn-2-yl ($C_8$), 5-hydroxy-5-ethylhept-3-ynyl ($C_9$), and 6-hydroxy-6-ethyloctyn-4-yn-2-yl ($C_{10}$).

The second category of CF Ring Systems relates to the (S,R) diastereomers having the formula:

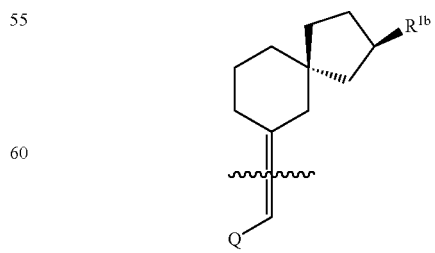

$R^{1b}$ is hydrogen or a $C_1$-$C_{20}$ substituted or unsubstituted, linear or branched hydrocarbyl unit.

The first aspect of $R^{1b}$ relates to unsubstituted $C_1$-$C_{10}$ linear or branched alkyl. Non-limiting examples of this first aspect of $R^{1b}$ include methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methylbutyl ($C_5$), 3-methylbutyl ($C_5$), 1,2-dimethylpropyl ($C_5$), 2,2-dimethylpropyl ($C_5$), n-hexyl ($C_6$), 1-methylpentyl ($C_6$), 2-methylpentyl ($C_6$), 3-methyl-pentyl ($C_6$), 4-methylpentyl ($C_6$), 1,1-dimethylbutyl ($C_6$), 1,2-dimethylbutyl ($C_6$), 1,3-dimethylbutyl ($C_6$), 2,2-dimethylbutyl ($C_6$), 2,3-dimethylbutyl ($C_6$), 3,3-dimethylbutyl ($C_6$), 1-ethylbutyl ($C_6$), 2-ethylbutyl ($C_6$), n-heptyl ($C_7$), 1-methylhexyl ($C_7$), 2-methyl-hexyl ($C_7$), 3-methylhexyl ($C_7$), 4-methylhexyl ($C_7$), 5-methylhexyl ($C_7$), 1,1-dimethyl-pentyl ($C_7$), 1,2-dimethylpentyl ($C_7$), 1,3-dimethylpentyl ($C_7$), 1,4-dimethylpentyl ($C_7$), 2,2-dimethylpentyl ($C_7$), 2,3-dimethylpentyl ($C_7$), 2,4-dimethylpentyl ($C_7$), 3,3-dimethyl-pentyl ($C_7$), 3,4-dimethylpentyl ($C_7$), and 4,4-dimethylpentyl ($C_7$).

The second aspect of $R^{1b}$ relates to substituted $C_1$-$C_4$ linear or branched alkyl wherein said substitution is preferably chosen from the group consisting of:

i) —$OR^{30}$ wherein $R^{30}$ is as defined hereinabove; for example, —OH, —$OCH_3$, —$OCH_2CH_3$, —$OCH_2CH_2CH_3$;

ii) halogen—fluoro, chloro, bromo, and iodo;

iii) —$CH_mX_n$; wherein X is halogen, the index m is from 0 to 2, the index n is from 1 to 3, m+n=3; for example, —$CH_2F$, —$CHF_2$, —$CF_3$, —$CH_2Cl$, —$CHCl_2$, —$CCl_3$, and —$CBr_3$; and iv) two hydrogens from adjacent carbon atoms are substituted by a single oxygen atom thereby forming an epoxy unit; for example but not limited to:

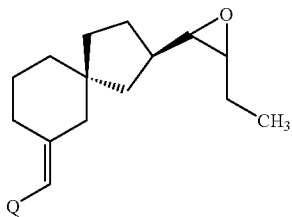

Non-limiting examples of this second aspect include fluoromethyl, difluoromethyl, trifluoromethyl, hydroxymethyl, 2-hydroxyethyl, 2-hydroxy-2-methylpropyl, and 4-hydroxybutyl;

The third aspect of $R^{1b}$ relates to substituted $C_5$-$C_{20}$ linear or branched alkyl wherein said substitution is preferably chosen from the group consisting of:

i) —$OR^{30}$ wherein $R^{30}$ is as defined hereinabove; for example, —OH, —$OCH_3$, —$OCH_2CH_3$, —$OCH_2CH_2CH_3$;

ii) —$CH_mX_n$; wherein X is halogen, the index m is from 0 to 2, the index n is from 1 to 3, m+n=3; for example, —$CH_2F$, —$CHF_2$, —$CF_3$, —$CH_2Cl$, —$CHCl_2$, —$CCl_3$, and —$CBr_3$; and iii) two hydrogens from adjacent carbon atoms are substituted by a single oxygen atom thereby forming an epoxy unit; for example but not limited to:

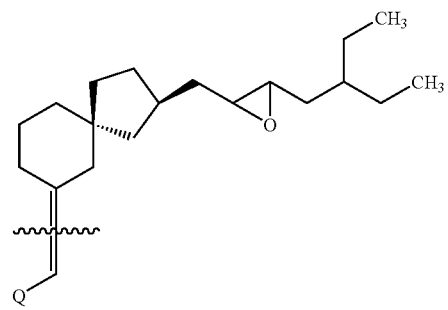

Non-limiting examples of this third aspect includes 1-hydroxy-4-methylpentan-1-yl ($C_6$); 2-hydroxy-4-methylpentan-1-yl ($C_6$); 3-hydroxy-4-methylpentan-1-yl ($C_6$); 4-hydroxy-4-methylpentan-1-yl ($C_6$); 1-hydroxy-5-methylhexan-2-yl ($C_7$); 2-hydroxy-5-methylhexan-2-yl ($C_7$); 3-hydroxy-5-methylhexan-2-yl ($C_7$); 4-hydroxy-5-methylhexan-2-yl ($C_7$); 5-hydroxy-5-methylhexan-2-yl ($C_7$); 1-hydroxy-6-methylheptan-2-yl ($C_8$); 2-hydroxy-6-methylheptan-2-yl ($C_8$); 3-hydroxy-6-methylheptan-2-yl ($C_8$); 4-hydroxy-6-methylheptan-2-yl ($C_8$); 5-hydroxy-6-methylheptan-2-yl ($C_8$); 1-hydroxy-5,5-dimethyl-hexan-1-yl ($C_8$), 1-trifluoromethyl-4-methylpentan-1-yl ($C_6$); 2-trifluoro-methyl-4-methyl-pentan-1-yl ($C_6$); 3-trifluoromethyl-4-methylpentan-1-yl ($C_6$); 4-trifluoromethyl-4-methyl-pentan-1-yl ($C_6$); 1-trifluoromethyl-5-methylhexan-2-yl ($C_7$); 2-trifluoromethyl-5-methylhexan-2-yl ($C_7$); 3-trifluoromethyl-5-methylhexan-2-yl ($C_7$); 4-trifluoromethyl-5-methyl-hexan-2-yl ($C_7$); 5-trifluoromethyl-5-methylhexan-2-yl ($C_7$); 1-trifluoromethyl-6-methylheptan-2-yl ($C_8$); 2-trifluoro-methyl-6-methylheptan-2-yl ($C_8$); 3-trifluoromethyl-6-methylheptan-2-yl ($C_8$); 4-trifluoromethyl-6-methylheptan-2-yl ($C_8$); 5-trifluoromethyl-6-methylheptan-2-yl ($C_8$); and 1-trifluoromethyl-5,5-dimethylhexan-1-yl ($C_8$).

The fourth aspect of $R^{1b}$ relates to unsubstituted $C_2$-$C_{20}$ linear or branched alkenyl. Non-limiting examples of this fourth aspect include 4-methylpent-2-enyl ($C_6$), 5-methylhex-2-enyl ($C_7$), 5-methylhex-3-enyl ($C_7$), 4-ethylhex-2-enyl ($C_8$), 6-methylhept-2-enyl ($C_8$), 6-methylhept-3-enyl ($C_8$), 6-methylhept-4-enyl ($C_8$), 7-methyloct-4-en-2-yl ($C_9$), 6-ethyloct-2-enyl ($C_{10}$), 6-ethyloct-3-enyl ($C_{10}$), and 6-ethyloct-4-enyl ($C_{10}$).

The fifth aspect of $R^{1b}$ relates to substituted $C_2$-$C_{20}$ linear or branched alkenyl. Non-limiting examples of this fifth aspect include: 4-hydroxy-4,4-bis-(trifluoro-methyl)but-2-enyl ($C_4$), 4-hydroxy-4-methylpent-2-enyl ($C_6$), 4-cyano-4-methylpent-2-enyl ($C_6$), 5-hydroxy-5-methylhex-2-enyl ($C_7$), 5-hydroxy-5-methylhex-3-enyl ($C_7$), 4-hydroxy-4-ethylhex-2-enyl ($C_8$), 6-hydroxy-6-methylhept-2-enyl ($C_8$), 6-hydroxy-6-methylhept-3-enyl ($C_8$), 6-hydroxy-6-methylhept-4-enyl ($C_8$), 7-hydroxy-7-methyloct-4-en-2-yl ($C_9$), 7-hydroxy-7-methyloct-3,5-dien-2-yl ($C_9$, 6-hydroxy-6-ethyloct-2-enyl ($C_{10}$), 6-hydroxy-6-ethyloct-3-enyl ($C_{10}$), 6-hydroxy-6-ethyloct-4-enyl ($C_{10}$), and 7-hydroxy-7-ethyl-non-3,5-dien-2-yl ($C_{11}$), The sixth aspect of $R^{1b}$ relates to unsubstituted $C_2$-$C_{20}$ linear or branched alkynyl. Non-limiting examples of this sixth aspect include: pent-2-ynyl ($C_5$), hex-2-ynyl ($C_6$), hex-3-ynyl ($C_6$), hex-3-yn-2-yl ($C_6$), hex-4-yn-2-yl ($C_6$), 5-methylhex-3-ynyl ($C_7$), 6-methylhept-3-yn-2-yl ($C_8$), 5-ethylhept-3-ynyl ($C_9$), and 6-ethyloctyn-4-yn-2-yl ($C_{10}$).

The seventh aspect of $R^{1b}$ relates to substituted $C_2$-$C_{20}$ linear or branched alkynyl. Non-limiting examples of this seventh aspect include: 5-hydroxy-5-methylhex-3-ynyl ($C_7$), 4-(2-methyl-oxyranyl)-but-3-ynyl ($C_7$), 6-hydroxy-6-methylhept-3-yn-2-yl ($C_8$), 5-(2-methyl-oxyranyl)-pent-4-yn-2-yl ($C_8$), 5-hydroxy-5-ethylhept-3-ynyl ($C_9$), and 6-hydroxy-6-ethyloctyn-4-yn-2-yl ($C_{10}$).

The third category of CF Ring Systems relates to the (R, R) diastereomers having the formula:

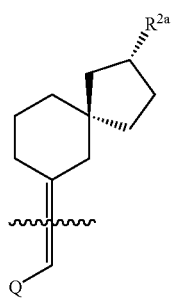

$R^{2a}$ is hydrogen or a $C_1$-$C_{20}$ substituted or unsubstituted, linear or branched hydrocarbyl unit.

The first aspect of $R^{2a}$ relates to unsubstituted $C_1$-$C_{10}$ linear or branched alkyl. Non-limiting examples of this first aspect of $R^{2a}$ include methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methylbutyl ($C_5$), 3-methylbutyl ($C_5$), 1,2-dimethylpropyl ($C_5$), 2,2-dimethylpropyl ($C_5$), n-hexyl ($C_6$), 1-methylpentyl ($C_6$), 2-methylpentyl ($C_6$), 3-methyl-pentyl ($C_6$), 4-methylpentyl ($C_6$), 1,1-dimethylbutyl ($C_6$), 1,2-dimethylbutyl ($C_6$), 1,3-dimethylbutyl ($C_6$), 2,2-dimethylbutyl ($C_6$), 2,3-dimethylbutyl ($C_6$), 3,3-dimethylbutyl ($C_6$), 1-ethylbutyl ($C_6$), 2-ethylbutyl ($C_6$), h-heptyl ($C_7$), 1-methylhexyl ($C_7$), 2-methyl-hexyl ($C_7$), 3-methylhexyl ($C_7$), 4-methylhexyl ($C_7$), 5-methylhexyl ($C_7$), 1,1-dimethyl-pentyl ($C_7$), 1,2-dimethylpentyl ($C_7$), 1,3-dimethylpentyl ($C_7$), 1,4-dimethylpentyl ($C_7$), 2,2-dimethylpentyl ($C_7$), 2,3-dimethylpentyl ($C_7$), 2,4-dimethylpentyl ($C_7$), 3,3-dimethyl-pentyl ($C_7$), 3,4-dimethylpentyl ($C_7$), and 4,4-dimethylpentyl ($C_7$).

The second aspect of $R^{2a}$ relates to substituted $C_1$-$C_4$ linear or branched alkyl wherein said substitution is preferably chosen from the group consisting of:

i) —$OR^{30}$ wherein $R^{30}$ is as defined hereinabove; for example, —OH, —$OCH_3$, —$OCH_2CH_3$, —$OCH_2CH_2CH_3$;

ii) halogen—fluoro, chloro, bromo, and iodo;

iii) —$CH_mX_n$; wherein X is halogen, the index m is from 0 to 2, the index n is from 1 to 3, m+n=3; for example, —$CH_2F$, —$CHF_2$, —$CF_3$, —$CH_2Cl$, —$CHCl_2$, —$CCl_3$, and —$CBr_3$; and iv) two hydrogens from adjacent carbon atoms are substituted by a single oxygen atom thereby forming an epoxy unit; for example but not limited to:

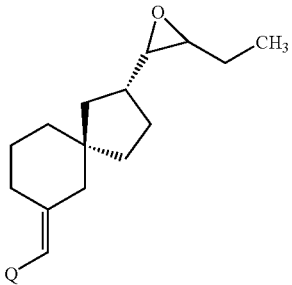

Non-limiting examples of this second aspect include fluoromethyl, difluoromethyl, trifluoromethyl, hydroxymethyl, 2-hydroxyethyl, 2-hydroxy-2-methylpropyl, and 4-hydroxybutyl.

The third aspect of $R^{2a}$ relates to substituted $C_5$-$C_{20}$ linear or branched alkyl wherein said substitution is preferably chosen from the group consisting of:

i) —$OR^{30}$ wherein $R^{30}$ is as defined hereinabove; for example, —OH, —$OCH_3$, —$OCH_2CH_3$, —$OCH_2CH_2CH_3$;

ii) —$CH_mX_n$; wherein X is halogen, the index m is from 0 to 2, the index n is from 1 to 3, m+n=3; for example, —$CH_2F$, —$CHF_2$, —$CF_3$, —$CH_2Cl$, —$CHCl_2$, —$CCl_3$, and —$CBr_3$; and iii) two hydrogens from adjacent carbon atoms are substituted by a single oxygen atom thereby forming an epoxy unit; for example but not limited to:

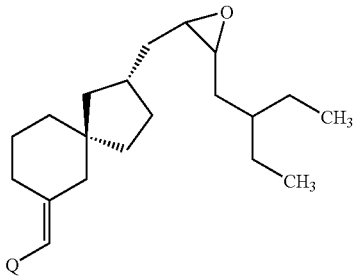

Non-limiting examples of this third aspect include 1-hydroxy-4-methylpentan-1-yl ($C_6$); 2-hydroxy-4-methylpentan-1-yl ($C_6$); 3-hydroxy-4-methylpentan-1-yl ($C_6$); 4-hydroxy-4-methylpentan-1-yl ($C_6$); 1-hydroxy-5-methylhexan-2-yl ($C_7$); 2-hydroxy-5-methylhexan-2-yl ($C_7$); 3-hydroxy-5-methylhexan-2-yl ($C_7$); 4-hydroxy-5-methylhexan-2-yl ($C_7$); 5-hydroxy-5-methylhexan-2-yl ($C_7$); 1-hydroxy-6-methylheptan-2-yl ($C_8$); 2-hydroxy-6-methylheptan-2-yl ($C_8$); 3-hydroxy-6-methylheptan-2-yl ($C_8$); 4-hydroxy-6-methylheptan-2-yl ($C_8$); 5-hydroxy-6-methylheptan-2-yl ($C_8$); 1-hydroxy-5,5-dimethyl-hexan-1-yl ($C_8$), 1-trifluoromethyl-4-methylpentan-1-yl ($C_6$); 2-trifluoro-methyl-4-methyl-pentan-1-yl ($C_6$); 3-trifluoromethyl-4-methylpentan-1-yl ($C_6$); 4-trifluoromethyl-4-methyl-pentan-1-yl ($C_6$); 1-trifluoromethyl-5-methylhexan-2-yl ($C_7$); 2-trifluoromethyl-5-methylhexan-2-yl ($C_7$); 3-trifluoromethyl-5-methyl-hexan-2-yl ($C_7$); 4-trifluoromethyl-5-methyl-hexan-2-yl ($C_7$); 5-trifluoromethyl-5-methylhexan-2-yl ($C_7$); 1-trifluoromethyl-6-methyl-heptan-2-yl ($C_8$); 2-trifluoro-methyl-6-methylheptan-2-yl ($C_8$); 3-trifluoromethyl-6-methylheptan-2-yl ($C_8$); 4-trifluoromethyl-6-methylheptan-2-yl ($C_8$); 5-trifluoromethyl-6-methylheptan-2-yl ($C_8$); and 1-trifluoromethyl-5,5-dimethylhexan-1-yl ($C_8$).

The fourth aspect of $R^{2a}$ relates to unsubstituted $C_2$-$C_{20}$ linear or branched alkenyl. Non limiting examples of this fourth aspect include 4-methylpent-2-enyl ($C_6$), 5-methylhex-2-enyl ($C_7$), 5-methylhex-3-enyl ($C_7$), 4-ethylhex-2-enyl ($C_8$), 6-methylhept-2-enyl ($C_8$), 6-methylhept-3-enyl ($C_8$), 6-methylhept-4-enyl ($C_8$), 7-methyloct-4-en-2-yl ($C_9$), 6-ethyloct-2-enyl ($C_{10}$), 6-ethyloct-3-enyl ($C_{10}$), and 6-ethyloct-4-enyl ($C_{10}$).

The fifth aspect of $R^{2a}$ relates to substituted $C_2$-$C_{20}$ linear or branched alkenyl.

Non-limiting examples of this fifth aspect include: 4-hydroxy-4,4-bis-(trifluoro-methyl)but-2-enyl ($C_4$), 4-hydroxy-4-methylpent-2-enyl ($C_6$), 4-cyano-4-methylpent-2-enyl ($C_6$), 5-hydroxy-5-methylhex-2-enyl ($C_7$), 5-hydroxy-5-methylhex-3-enyl ($C_7$), 4-hydroxy-4-ethylhex-2-enyl ($C_8$), 6-hydroxy-6-methylhept-2-enyl ($C_8$), 6-hydroxy-6-methylhept-3-enyl ($C_8$), 6-hydroxy-6-methylhept-4-enyl ($C_8$), 7-hydroxy-7-methyloct-4-en-2-yl ($C_9$), 7-hydroxy-7-methyloct-3,5-dien-2-yl ($C_9$), 6-hydroxy-6-ethyloct-2-enyl ($C_{10}$), 6-hydroxy-6-ethyloct-3-enyl ($C_{10}$), 6-hydroxy-6-ethyloct-4-enyl ($C_{10}$), and 7-hydroxy-7-ethylnon-3,5-dien-2-yl ($C_{11}$), The sixth aspect of $R^{2a}$ relates to unsubstituted $C_2$-$C_{20}$ linear or branched alkynyl. Non-limiting examples of this sixth aspect include: pent-2-ynyl ($C_5$), hex-2-ynyl ($C_6$), hex-3-ynyl ($C_6$), hex-3-yn-2-yl ($C_6$), hex-4-yn-2-yl ($C_6$), 5-methylhex-3-ynyl ($C_7$), 6-methylhept-3-yn-2-yl ($C_8$), 5-ethylhept-3-ynyl ($C_9$), and 6-ethyloctyn-4-yn-2-yl ($C_{10}$).

The seventh aspect of $R^{2a}$ relates to substituted $C_2$-$C_{20}$ linear or branched alkynyl. Non-limiting examples of this seventh aspect include: 5-hydroxy-5-methylhex-3-ynyl ($C_7$), 4-(2-methyl-oxyranyl)-but-3-ynyl ($C_7$), 6-hydroxy-6-methylhept-3-yn-2-yl ($C_8$), 5-(2-methyl-oxyranyl)-pent-4-yn-2-yl ($C_8$), 5-hydroxy-5-ethylhept-3-ynyl ($C_9$), and 6-hydroxy-6-ethyloctyn-4-yn-2-yl ($C_{10}$)

The fourth category of CF Ring Systems relates to the (R,S) diastereomers having the formula:

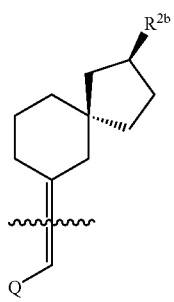

$R^{2b}$ is a $C_1$-$C_{20}$ substituted or unsubstituted, linear or branched hydrocarbyl units.

The first aspect of $R^{2b}$ relates to unsubstituted $C_1$-$C_{10}$ linear or branched alkyl. Non-limiting examples of this first aspect of $R^{2b}$ include methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methylbutyl ($C_5$), 3-methylbutyl ($C_5$), 1,2-dimethylpropyl ($C_5$), 2,2-dimethylpropyl ($C_5$), n-hexyl ($C_6$), 1-methylpentyl ($C_6$), 2-methylpentyl ($C_6$), 3-methyl-pentyl ($C_6$), 4-methylpentyl ($C_6$), 1,1-dimethylbutyl ($C_6$), 1,2-dimethylbutyl ($C_6$), 1,3-dimethylbutyl ($C_6$), 2,2-dimethylbutyl ($C_6$), 2,3-dimethylbutyl ($C_6$), 3,3-dimethylbutyl ($C_6$), 1-ethylbutyl ($C_6$), 2-ethylbutyl ($C_6$), n-heptyl ($C_7$), 1-methylhexyl ($C_7$), 2-methyl-hexyl ($C_7$), 3-methylhexyl ($C_7$), 4-methylhexyl ($C_7$), 5-methylhexyl ($C_7$), 1,1-dimethyl-pentyl ($C_7$), 1,2-dimethylpentyl ($C_7$), 1,3-dimethylpentyl ($C_7$), 1,4-dimethylpentyl ($C_7$), 2,2-dimethylpentyl ($C_7$), 2,3-dimethylpentyl ($C_7$), 2,4-dimethylpentyl ($C_7$), 3,3-dimethylpentyl ($C_7$), 3,4-dimethylpentyl ($C_7$), and 4,4-dimethylpentyl ($C_7$).

The second aspect of $R^{2b}$ relates to substituted $C_1$-$C_4$ linear or branched alkyl wherein said substitution is preferably chosen from the group consisting of:
i) —$OR^{30}$ wherein $R^{30}$ is as defined hereinabove; for example, —OH, —$OCH_3$, —$OCH_2CH_3$, —$OCH_2CH_2CH_3$;
ii) halogen—fluoro, chloro, bromo, and iodo;
iii) —$CH_mX_n$; wherein X is halogen, the index m is from 0 to 2, the index n is from 1 to 3, m+n=3; for example, —$CH_2F$, —$CHF_2$, —$CF_3$, —$CH_2Cl$, —$CHCl_2$, —$CCl_3$, and —$CBr_3$; and
iv) two hydrogens from adjacent carbon atoms are substituted by a single oxygen atom thereby forming an epoxy unit; for example but not limited to:

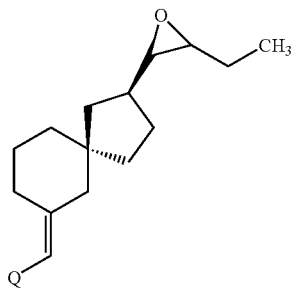

Non-limiting examples of this second aspect includes fluoromethyl, difluoromethyl, trifluoromethyl, hydroxymethyl, 2-hydroxyethyl, 2-hydroxy-2-methylpropyl, and 4-hydroxybutyl.

The third aspect of $R^{2b}$ relates to substituted $C_5$-$C_{20}$ linear or branched alkyl wherein said substitution is preferably chosen from the group consisting of:
i) —$OR^{30}$ wherein $R^{30}$ is as defined hereinabove; for example, —OH, —$OCH_3$, —$OCH_2CH_3$, —$OCH_2CH_2CH_3$;
ii) —$CH_mX_n$; wherein X is halogen, the index m is from 0 to 2, the index n is from 1 to 3, m+n=3; for example, —$CH_2F$, —$CHF_2$, —$CF_3$, —$CH_2Cl$, —$CHCl_2$, —$CCl_3$, and —$CBr_3$; and
iii) two hydrogens from adjacent carbon atoms are substituted by a single oxygen atom thereby forming an epoxy unit; for example but not limited to:

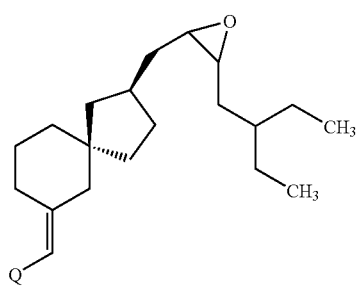

Non-limiting examples of this third aspect include 1-hydroxy-4-methylpentan-1-yl ($C_6$); 2-hydroxy-4-methylpentan-1-yl ($C_6$); 3-hydroxy-4-methylpentan-1-yl ($C_6$); 4-hydroxy-4-methylpentan-1-yl ($C_6$); 1-hydroxy-5-methylhexan-2-yl ($C_7$); 2-hydroxy-5-methylhexan-2-yl ($C_7$); 3-hydroxy-5-methylhexan-2-yl ($C_7$); 4-hydroxy-5-methylhexan-2-yl ($C_7$); 5-hydroxy-5-methylhexan-2-yl ($C_7$); 1-hydroxy-6-methylheptan-2-yl ($C_8$); 2-hydroxy-6-methylheptan-2-yl ($C_8$); 3-hydroxy-6-methylheptan-2-yl ($C_8$); 4-hydroxy-6-methylheptan-2-yl ($C_8$); 5-hydroxy-6-methylheptan-2-yl ($C_8$); 1-hydroxy-5,5-dimethyl-hexan-1-yl ($C_8$), 1-trifluoromethyl-4-methylpentan-1-yl ($C_6$); 2-trifluoro-methyl-4-methyl-pentan-1-yl ($C_6$); 3-trifluoromethyl-4-methylpentan-1-yl ($C_6$); 4-trifluoromethyl-4-methyl-pentan-1-yl ($C_6$); 1-trifluoromethyl-5-methylhexan-2-yl ($C_7$); 2-trifluoromethyl-5-methylhexan-2-yl ($C_7$); 3-trifluoromethyl-5-methylhexan-2-yl ($C_7$); 4-trifluoromethyl-5-methyl-hexan-2-yl ($C_7$); 5-trifluoromethyl-5-methylhexan-2-yl ($C_7$); 1,4-trifluoromethyl-6-methyl-heptan-2-yl ($C_8$); 2-trifluoro-methyl-6-methylheptan-2-yl ($C_8$); 3-trifluoromethyl-6-methylheptan-2-yl ($C_8$); 4-trifluoromethyl-6-methyl lheptan-2-yl ($C_8$); 5-trifluoromethyl-6-methylheptan-2-yl ($C_8$); and 4-trifluoromethyl-5,5-dimethylhexan-1-yl ($C_8$).

The fourth aspect of $R^{2b}$ relates to unsubstituted $C_2$-$C_{20}$ linear or branched alkenyl. Non-limiting examples of this fourth aspect include 4-methylpent-2-enyl ($C_6$), 5-methylhex-2-enyl ($C_7$), 5-methylhex-3-enyl ($C_7$), 4-ethylhex-2-enyl ($C_8$), 6-methylhept-2-enyl ($C_8$), 6-methylhept-3-enyl ($C_8$), 6-methylhept-4-enyl ($C_8$), 7-methyloct-4-en-2-yl ($C_9$), 6-ethyloct-2-ehyl ($C_{10}$), 6-ethyloct-3-enyl ($C_{10}$), and 6-ethyloct-4-enyl ($C_{10}$).

The fifth aspect of $R^{2b}$ relates to substituted $C_2$-$C_{20}$ linear or branched alkenyl. Non-limiting examples of this fifth aspect include: 4-hydroxy-4,4-bis-(trifluoro-methyl)but-2-enyl ($C_4$), 4-hydroxy-4-methylpent-2-enyl ($C_6$), 4-cyano-4-methylpent-2-enyl ($C_6$), 5-hydroxy-5-methylhex-2-enyl ($C_7$), 5-hydroxy-5-methylhex-3-enyl ($C_7$), 4-hydroxy-4-ethylhex-2-enyl ($C_8$), 6-hydroxy-6-methylhept-2-enyl ($C_8$), 6-hydroxy-6-methylhept-3-enyl ($C_8$), 6-hydroxy-6-methylhept-4-enyl ($C_8$), 7-hydroxy-7-methyloct-4-en-2-yl ($C_9$) 7-hydroxy-7-methyloct-3,5-dien-2-yl ($C_9$), 6-hydroxy-6-ethyloct-2-enyl ($C_{10}$), 6-hydroxy-6-ethyloct-3-enyl ($C_{10}$), 6-hydroxy-6-ethyloct-4-enyl ($C_{10}$), and 7-hydroxy-7-ethylnon-3,5-dien-2-yl ($C_{11}$), The sixth aspect of $R^{2b}$ relates to unsubstituted $C_2$-$C_{20}$ linear or branched alkynyl. Non-limiting examples of this sixth aspect include: pent-2-ynyl ($C_5$), hex-2-ynyl ($C_6$), hex-3-ynyl ($C_6$), hex-3-yn-2-yl ($C_6$), hex-4-yn-2-yl ($C_6$), 5-methylhex-3-ynyl ($C_7$), 6-methylhept-3-yn-2-yl ($C_8$), 5-ethylhept-3-ynyl ($C_9$), and 6-ethyloctyn-4-yn-2-yl ($C_{10}$).

The seventh aspect of $R^{2b}$ relates to substituted $C_2$-$C_{20}$ linear or branched alkynyl. Non-limiting examples of this seventh aspect include: 5-hydroxy-5-methylhex-3-ynyl ($C_7$), 4-(2-methyl-oxyranyl)-but-3-ynyl ($C_7$), 6-hydroxy-6-methylhept-3-yn-2-yl ($C_8$), 5-(2-methyl-oxyranyl)-pent-4-yn-2-yl ($C_8$), 5-hydroxy-5-ethylhept-3-ynyl ($C_9$), and 6-hydroxy-6-ethyloctyn-4-yn-2-yl ($C_{10}$).

A non-limiting example of a further category of compounds according to the present invention relates to compounds wherein a carbon atom 20 or 21 of the F-Ring has both hydrogen atoms replaced with substituents, for example, both $R^{2a}$ and $R^{2b}$ units are non-hydrogen atom units such as shown in the following exemplary but not limiting structural formula:

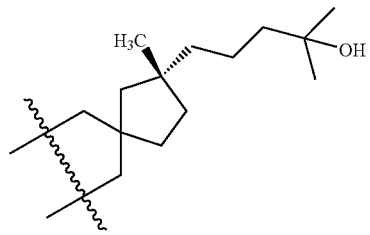

The following are non-limiting categories of the of spiro[4.5]decane units which comprise the compounds of the present invention.

A first category of spiro[4.5]decane units are units having the formula:

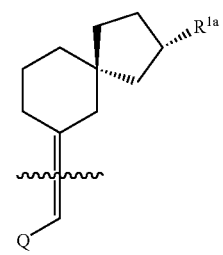

wherein $R^{1b}$, $R^{2a}$ and $R^{2b}$ are each hydrogen and wherein $R^{1a}$ is the same as defined herein above.

A second category of spiro[4.5]decane units are units having the formula:

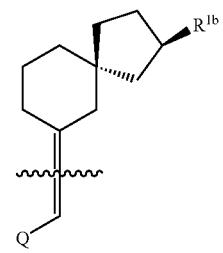

wherein $R^{1a}$, $R^{2a}$ and $R^{2b}$ are each hydrogen and wherein $R^{1b}$ is the same as defined herein above.

A third category of spiro[4.5]decane units are units having the formula:

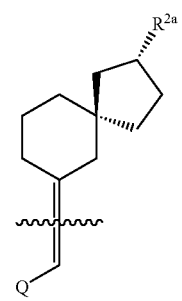

wherein $R^{1a}$, $R^{1b}$ and $R^{2b}$ are each hydrogen and wherein $R^{2a}$ is the same as defined herein above.

A fourth category of spiro[4.5]decane units are units having the formula:

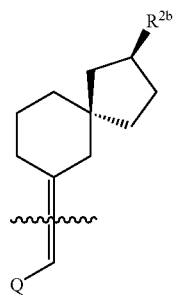

wherein $R^{1a}$, $R^{1b}$ and $R^{2a}$ are each hydrogen and wherein $R^{2b}$ is the same as defined herein above. However, other categories of the present invention relating to spiro[4.5]decane units are encompassed within the present definition.

The following are non-limiting categories of the of Q units which comprise the compounds of the present invention. For the purposes of the present definitions Q units have the formula:

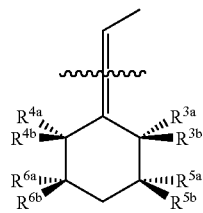

however, for brevity only one isomer is illustrated.

A first category of Q units have the formula:

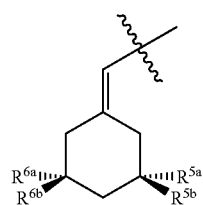

wherein $R^{3a}$, $R^{3b}$, $R^{4a}$, and $R^{4b}$ are each hydrogen; and wherein $R^{5a}$, $R^{5b}$, $R^{6a}$ and $R^{6b}$ are each independently selected from the group consisting of hydrogen, hydroxyl and hydroxyl-protecting groups.

A first aspect of the first category of Q units are rings having the formula:

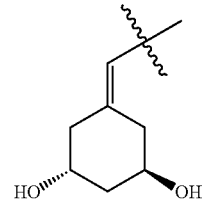

wherein $R^{5b}$ and $R^{6a}$ are each hydroxyl or a hydroxyl-protecting group and wherein $R^{5a}$ and $R^{6b}$ are each hydrogen.

A second aspect of the first category of Q units are rings having the formula:

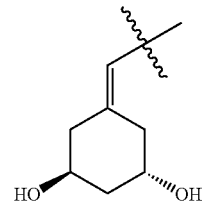

wherein $R^{5a}$ and $R^{6b}$ are each hydroxyl or a hydroxyl-protecting group and wherein $R^{5b}$ and $R^{6a}$ are each hydrogen.

A third aspect of the first category of Q units are rings having the formula:

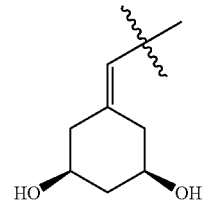

wherein $R^{5b}$ and $R^{6b}$ are each hydroxyl or a hydroxyl-protecting group and wherein $R^{5a}$ and $R^{6a}$ are each hydrogen.

A fourth aspect of the first category of Q units are rings having the formula:

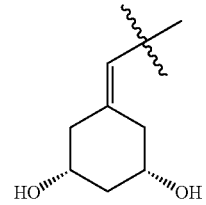

wherein $R^{5a}$ and $R^{6a}$ are each hydroxyl or a hydroxyl-protecting group and wherein $R^{5b}$ and $R^{6b}$ are each hydrogen.

A second category of Q units have the formula:

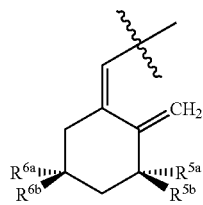

wherein $R^{3a}$ and $R^{3b}$ are taken together to form an exocyclic methylene unit; $R^{4a}$ and $R^{4b}$ are each hydrogen; and $R^{5a}$, $R^{5b}$, $R^{6a}$ and $R^{6b}$ are each independently hydrogen or hydroxyl or a hydroxyl-protecting group.

A first aspect of the second category of Q units are rings having the formula:

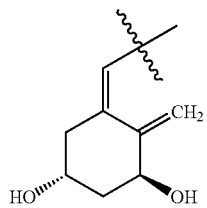

wherein $R^{5b}$ and $R^{6a}$ are each hydroxyl or a hydroxyl-protecting group and $R^{5a}$ and $R^{6b}$ are each hydrogen.

A second aspect of the second category of Q units are rings having the formula:

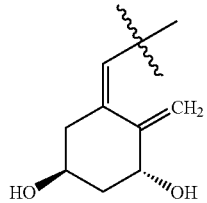

wherein $R^{5a}$ and $R^{6b}$ are each hydroxyl or a hydroxyl-protecting group and $R^{5b}$ and $R^{6a}$ are each hydrogen.

A third aspect of the second category of Q units are rings having the formula:

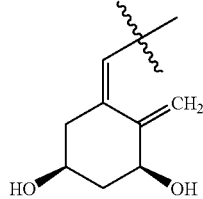

wherein $R^{5b}$ and $R^{6b}$ are each hydroxyl or a hydroxyl-protecting group and $R^{5a}$ and $R^{6a}$ are each hydrogen.

A fourth aspect of the second category of Q units are rings having the formula:

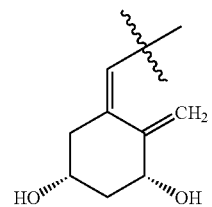

wherein $R^{5a}$ and $R^{6a}$ are each hydroxyl or a hydroxyl-protecting group and $R^{5b}$ and $R^{6b}$ are each hydrogen.

A third category of Q units have the formula:

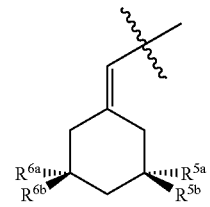

wherein $R^{3a}$, $R^{3b}$, $R^{4a}$, and $R^{4b}$ are each hydrogen; one of $R^{5a}$, $R^{5b}$, $R^{6a}$ or $R^{6b}$ is hydroxyl or a hydroxyl-protecting group and the balance of $R^{5a}$, $R^{5b}$, $R^{6a}$ or $R^{6b}$ are hydrogen.

Non-limiting aspects of a third category of Q units includes units having the formula:

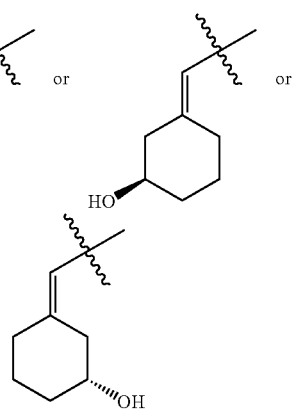

A fourth category of Q units have the formula:

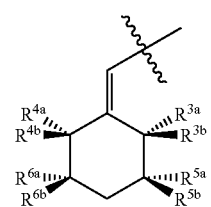

wherein:
a) an exocyclic methylene is present in the Q unit such that:
i) $R^{3a}$ and $R^{3b}$ are taken together to form an exocyclic methylene unit and $R^{4a}$ and $R^{4b}$ are each hydrogen; or
ii) $R^{4a}$ and $R^{4b}$ are taken together to form an exocyclic methylene unit and $R^{3a}$ and $R^{3b}$ are each hydrogen; and
b) one of $R^{5a}$, $R^{5b}$, $R^{6a}$ or $R^{6b}$ is hydroxyl or a hydroxyl-protecting group and the balance of $R^{5a}$, $R^{5b}$, $R^{6a}$ or $R^{6b}$ are hydrogen.

Non-limiting aspects of a fourth category of Q units includes units having the formula:

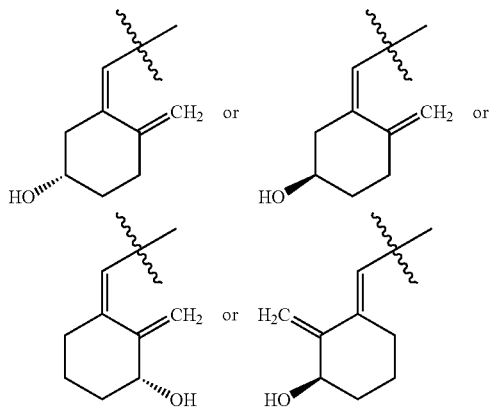

A fifth category (not shown in any of the previous formulae) of Q units which may be comprised in the compounds of this invention includes, on carbon 2 of said compound (according to the scaffold numbering system described herein above), one or two substituents R and/or R', wherein R and R' are each independently selected from the group consisting of substituted and unsubstituted $C_{1-7}$ alkyl. Preferably within this category, R and/or R' is methyl or ethyl, and R and/or R' is optionally substituted with one or more functional atoms or groups selected from the group consisting of fluoro, chloro, hydroxy, sulfhydryl and amino. More preferably carbon 2 is mono-substituted, i.e. only has one substituent R being most preferably methyl or ethyl. Specific examples of this fifth category are not illustrated hereunder, however their synthesis is similar to that of compounds of the four other categories, starting from precursors having the suitable substituents R and/or R', which can be made according to the teachings of De Luca and co-workers.

However, other categories of the present invention relating Q units may be encompassed within the present definitions.

All of the above definitions apply equally well for the corresponding isomer, for example, the categories defining Q having the formula:

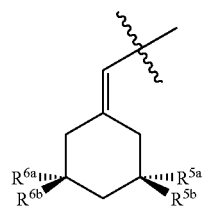

also define the categories of the isomer.

For a purpose of convenience, the compounds of the present invention are arranged herein into different categories This arrangement into categories does not imply any ranking among the corresponding compounds, such as an increased or decreased medicinal importance or efficacy for any of the pharmaceutical compositions described herein and/or for any of the methods of preventing or treating disorders described herein.

Schemes I and II and Examples 1 and 2 herein below outline the synthesis and identification of intermediates which result in the formation of exemplary but non-limiting (S,S) and (S,R) upper CF-Ring scaffolds.

The present invention also relates to a number of intermediates, most of them having a specific stereochemistry, and which are useful in the preparation of the final vitamin D analogues of the different categories stated herein above. The preparation and the detailed formulae of a first set of these intermediates are shown in the following scheme I comprising a sequence of eleven process steps for making the pure (+) and (−) isomers of 1,4-dioxa-dispiro[4.1.5.3]pentadec-8-ene. Each step will now be illustrated in details, based on specific starting compounds, reactive agents, catalysts, solvents, temperature ranges and the like, but the skilled person will understand that the specific materials and conditions disclosed herein may be replaced with similar or equivalent materials and conditions without significantly altering the resulting product of the relevant step, except perhaps for the reaction yield or, in the case of a stereoselective reaction, the enantiomeric excess of the product shown.

Scheme I

Synthesis of the pure (+) and (−) isomers of 1,4-dioxa-dispiro[4.1.5.3]pentadec-8-ene starts, as a first step (a), with the halogenation, preferably the bromination, of 3-ethoxy-2-cyclohexenone, e.g. according to the procedure disclosed by Hara et al. in *J. Am. Chem. Soc.* (1999)121, 3072-3082:

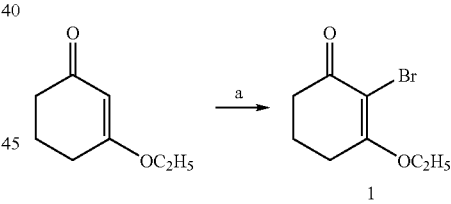

(preferred reagents and conditions for step (a): N-bromosuccinimide as a reagent, $CH_2Cl_2$ as a solvent; temperature range from about 0° C. to about 40° C.).

In a second step (b), the 2-bromo-3-ethoxy-cyclohex-2-enone resulting from step (a) is n-butylated for instance, but without limitation, by means of 1-chloro-4-methoxybutane (the latter may be prepared according to the procedures disclosed by Hara et al. in *J. Org. Chem.* (1975) 40, 2786-2791 and by De Buyck et al. in *Bull. Soc. Chim. Belg.* (1992) 101, 807-815) in the presence of an effective amount of an organometallic derivative such as a Grignard reagent. In a more specific embodiment in order to improve butylation yield, said step may additionally be performed in the presence of a stoechiometric amount of cerium trichloride. This specific embodiment is believed to result in the formation of an organocerium active species as shown in the scheme below, although said presumed active species was not isolated:

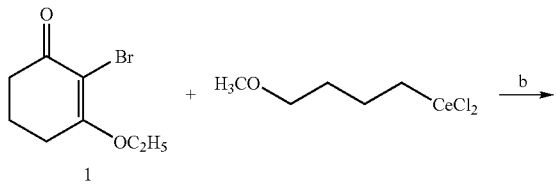

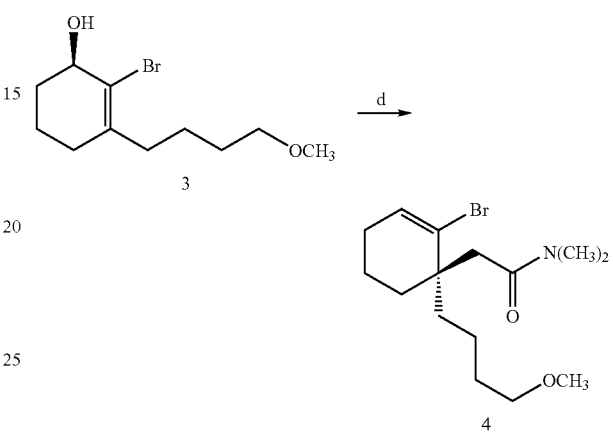

(preferred reagents and conditions for step (b): THF as a solvent; temperature range from about 0° C. to about 40° C. after refluxing to create the Grignard reagent; magnesium, 1-chloro-4-methoxybutane and cerium trichloride as active reagents).

In a third step (c), the 2-bromo-3-(4-methoxybutyl)-cyclohex-2-enone resulting from step (b) is stereoselectively reduced by means of an effective amount of a reducing agent in the presence of a catalytic amount of a suitable stereoselective reduction catalyst. Suitable reducing agents for this reduction step include, but are not limited to, borane, catecholborane and borohydride reagents. Suitable stereoselective reduction catalysts for this reduction step include, but are not limited to, substantially pure methyloxazaborolidinone isomers and metal complexes, either monometallic, homobimetallic or heterobimetallic, such as lithium aluminum hydrides or transition metal complexes, having one or more chiral ligands. The skilled person understands that this step is very important for the present invention since it determines the success of the whole synthetic route up to the desired following stereoisomeric intermediates and vitamin $D_3$ analogs. Therefore the skilled person, based on the general knowledge relating to reducing catalysts and agents, will make a careful selection of the reaction conditions in view of various considerations such as reaction yield, productivity and, mainly, enantiomeric excess of one stereoisomer of the resulting product with respect to the other stereoisomer.

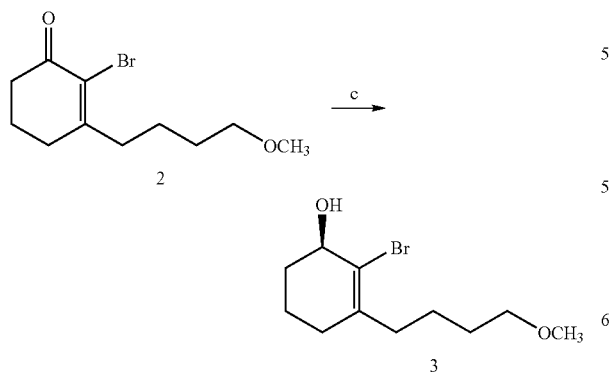

(preferred reagents and conditions for step (c) as shown above: (S)-methyloxazaborolidinone (or (R)-methyloxazaborolidinone as in scheme I') as a catalyst, catecholborane as a reducing agent, toluene as a solvent; temperature range from about −95° C. to about 25° C., more preferably from −78° C. to about 0° C.).

In a fourth step (d), the 2-bromo-3-(4-methoxybutyl)-cyclohex-2-enol stereoisomer resulting from step (c) is submitted to a 3,3-sigmatropic rearrangement by means of a dimethylamino-dimethylacetal (preferably in an at least stoechiometric amount), preferably in the presence of a suitable solvent:

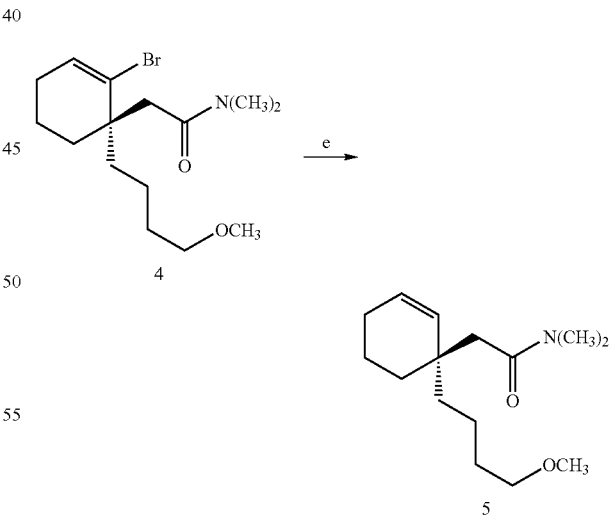

(preferred reagents and conditions for step (d): $(CH_3)_2N[CCH_3(OCH_3)_2]$ as a reagent, toluene as a solvent; temperature: reflux of the solvent).

In a fifth step (e), the 2-[2-bromo-1-(4-methoxybutyl)-cyclohex-2-enyl]-N,N-dimethylacetamide stereoisomer resulting from step (d) is reduced by means of a reducing agent such as a metal hydride, preferably in the presence of a suitable solvent and optionally in the presence of a free radical initiator:

(preferred reagents and conditions for step (e): $Bu_3SnH$ as the reducing agent, azobis-isobutyronitrile as a free radical initiator; THF a solvent; temperature: reflux of the solvent).

In a sixth step (f), the 2-[1-(4-methoxybutyl)-cyclohex-2-enyl]-N,N-dimethylacetamide stereoisomer resulting from step (e) is submitted to ether cleavage, preferably in the presence of a Lewis acid reagent, a nucleophile reagent and an effective amount of suitable catalyst such as a crown ether.

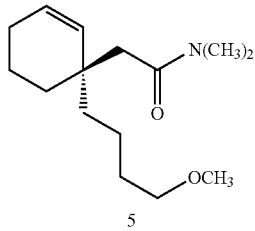

5

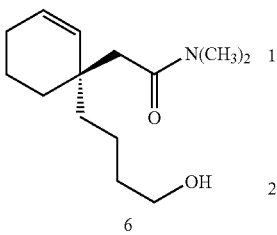

6

(preferred reagents and conditions for step (f): BBr$_3$ as a Lewis acid, NaI as a nucleophilic reagent, and 15-crown-5 as a catalyst, CH$_2$Cl$_2$ as a solvent; temperature range from about −40° C. to about −20° C.).

In a seventh step (g), the 2-[1-(4-hydroxybutyl)-cyclohex-2-enyl]-N,N-dimethylacetamide stereoisomer resulting from step (f) is oxidized in the presence of a suitable oxidation reagent, preferably a chromium (VI) compound, preferably at moderate temperature and in the presence of a suitable solvent:

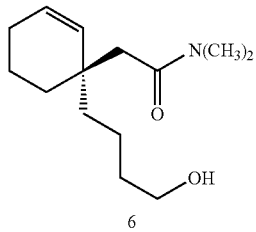

6

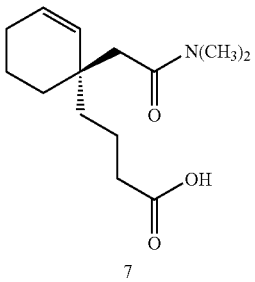

7

(preferred reagents and conditions for step (g): pyridinium dichromate as an oxidation reagent, DMF as a solvent; temperature range from about 10° C. to about 40° C.).

In an eighth step (h), the 4-(1-dimethylcarbamoylmethyl-cyclohex-2-enyl)-butyric acid stereoisomer resulting from step (g) is esterified, preferably in two sub-steps including first a strong base at elevated temperatures, and secondly the presence of an aliphatic alcohol optionally in the presence of an effective amount of an esterification catalyst:

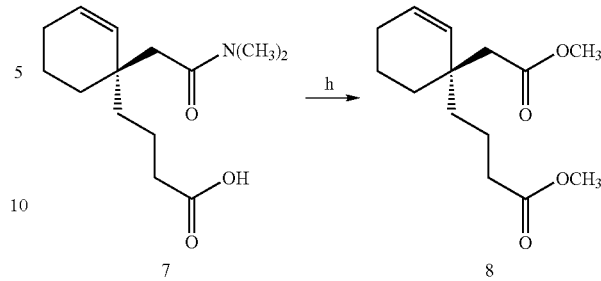

7                                      8

(preferred reagents and conditions for step (h): first (i) KOH, dioxane/water mixture as a solvent, temperature range from about 160° C. to about 240° C.; then (ii) diazomethane (CH$_2$N$_2$), MeOH).

In an ninth step (i), the 4-(1-dimethylcarbamoylmethyl-cyclohex-2-enyl)-butyric acid methyl ester stereoisomer resulting from step (h) is submitted to a Dieckmann condensation into a β-keto ester preferably in the presence of a strong base such as a sodium alkoxide or a lithium amide, and optionally in the presence of a suitable solvent:

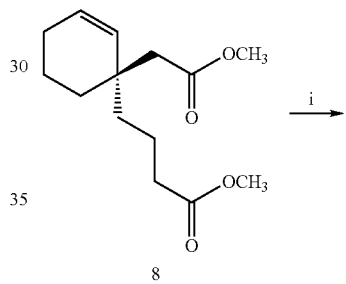

8

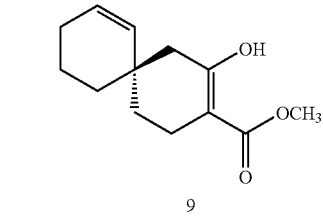

9

(preferred reagents and conditions for step (i): lithium diisopropylamide as a base, THF as a solvent; temperature range from about −80° C. to about 40° C.).

In a tenth step (j), the 2-hydroxy-spiro[5.5]undecan-2,7-diene-3-carboxylic acid methyl ester stereoisomer resulting from step (i) is submitted to oxidative decarboxylation, preferably in the presence of an oxidative agent:

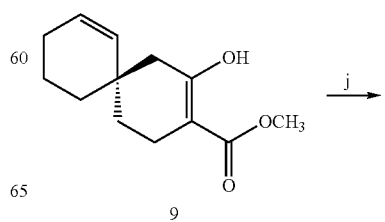

9

-continued

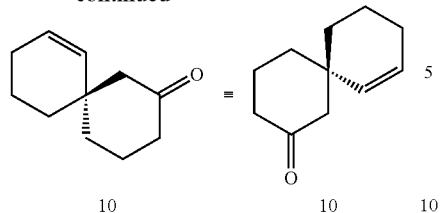

(preferred reagents and conditions for step (j): NaCl, water, and DMSO both as a solvent and an oxidative agent; temperature range from about 140° C. to about 180° C.).

In an eleventh step (k), the spiro[5.5]undec-7-en-2-one stereoisomer resulting from step (i) is submitted to ketalization by means of an aliphatic diol, optionally in the presence of an acidic catalyst:

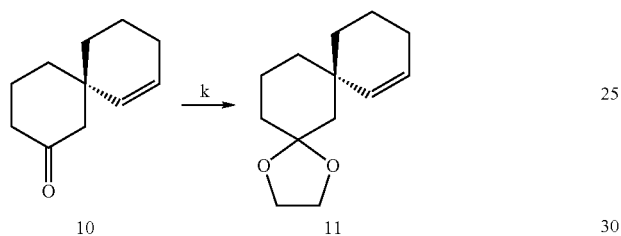

(preferred reagents and conditions for step (k): HOCH$_2$CH$_2$OH as a reagent, p-toluenesulfonic acid as a catalyst, toluene as a solvent; temperature at reflux of the solvent).

The skilled person understands that, alternatively in step (k), thioacetalization may be performed by means of HSCH$_2$CH$_2$SH as a reagent and that the resulting 1,4-dithia-dispiro[4.1.5.3]pentadec-8-ene stereoisomers and their derivatives, although not specifically shown in the above and following formulae, also form part of the intermediates of the present invention.

For the ease of understanding and the completion of the disclosure of other stereoisomers which are also available by this methodology, scheme I' hereunder provides a full depiction of a similar synthetic route starting from 2-bromo-3-(4-methoxybutyl)-cyclohex-2-enone but wherein the stereoselective catalyst is (R)-methyloxazaborolidinone.

Scheme I'

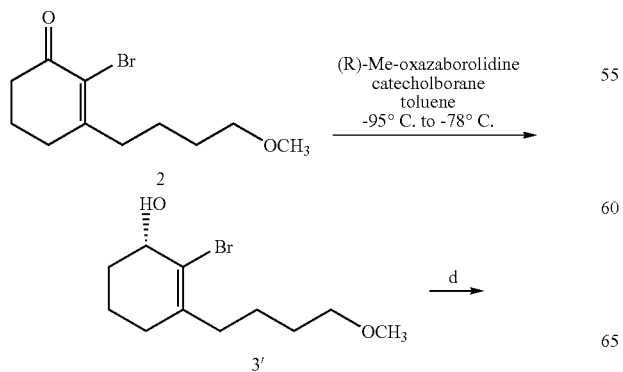

-continued

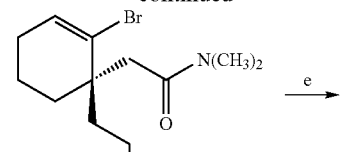
4'

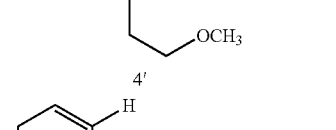
5'

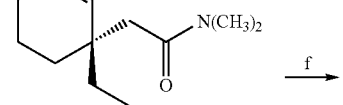
6'

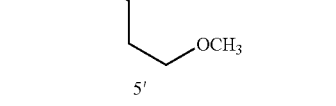
7'

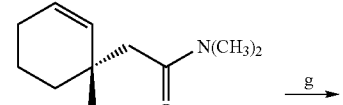
8'

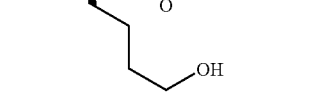
9'

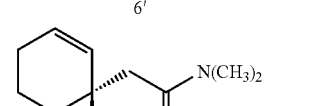
10'

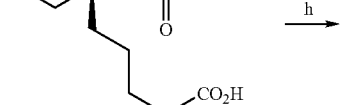
11'

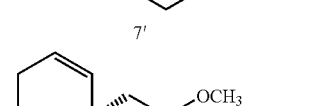
10'

EXAMPLE 1

Preparation of 1,4-dioxa-dispiro[4.1.5.3]pentadec-8-ene stereoisomers (11) and (11') and 1,4-dithia-dispiro[4.1.5.3]pentadec-8-ene stereoisomers The preparation of 1,4-dioxa-dispiro[4.1.5.3]pentadec-8-ene stereoisomers was effected via the principles of the eleven steps synthetic route described above, and more specifically as outlined hereunder.

a) Preparation of 2-bromo-3-ethoxy-cyclohex-2-enone (1)

To a solution of 3-ethoxy-2-cyclohexenone (70 g, 499 mmol) in $CH_2Cl_2$ (300 mL) as a solvent at 0° C. under argon atmosphere was added in portions N-bromosuccinimide (91 g, 511 mmol) over a period of 1 hour. The suspension was stirred at 0° C. for 1 hour and then at room temperature for 2 hours. The solvent was removed in vacuo and $CH_2Cl_2$ added. The solution was washed twice with a cold saturated $NaHCO_3$ solution and with cold $H_2O$, then dried over anhydrous $MgSO_4$, the solvent removed in vacuo and the resulting solid residue was triturated several times with $Et_2O$, the resulting solid dried in vacuo to afford 101 g (92% yield) of the desired product as white crystals which were characterized as follows:

$R_f$ ($Et_2O$) 0.33;
Ultraviolet (UV) absorption (MeOH) at 273 nm;
Infrared (IR) main absorption bands (KBr) at 2966, 2939, 1657, 1568, 1430, 1397, 1371, 1348, 1324, 1295, 1260, 1246, 1195, 1150, 1107, 1076, 1030, 959, 922, 850, 798, 614 and 470 $cm^{-1}$;
proton nuclear magnetic resonance ($^1H$ NMR) (500 MHz, $CDCl_3$): 4.21 (2 H, q, J=7.0 Hz), 2.69 (3 H, t, J=6.2 Hz), 2.55-2.52 (2 H, m), 2.07-2.02 (2 H, m), 1.43 (2 H, t, J=7.0 Hz) ppm;
carbon nuclear magnetic resonance ($^{13}C$ NMR) (50 MHz, $CDCl_3$): 191.0 (C), 172.8 (C), 103.0 (C), 65.2 ($CH_2$), 36.7 ($CH_2$), 27.2 ($CH_2$), 20.6 ($CH_2$) and 15.1 ($CH_3$) ppm;
mass spectrum MS m/z (%): 220/218 ($M^+$, 16/20), 192/190 (25/25), 164/162 (75/100), 149 (12), 111 (15), 67 (21) and 55 (51).

b) Preparation of 2-bromo-3-(4-methoxy-butyl)-cyclohex-2-enone (2)

To magnesium turnings (9.84 g, 405 mmol) in dry THF (42 mL) as a solvent were added a few crystals of iodine and a few drops of $CH_2Br_2$. A solution of 1-chloro-4-methoxybutane (46.8 g, 382 mmol) in dry THF (90 mL) was added dropwise at a rate sufficient to maintain gentle reflux. The reaction mixture was then refluxed for 1 hour and then cooled to room temperature. The resulting Grignard reagent was then added dropwise to a suspension of $CeCl_3$ (94.2 g, 382 mmol) in dry THF (750 mL) at 0° C. After stirring at room temperature for 2 hours, a solution of 2-bromo-3-ethoxy-cyclohex-2-enone (1) (60 g, 274 mmol) in dry THF (300 mL) was added dropwise at 0° C. The reaction mixture was stirred an additional 2 hours at room temperature and then quenched by adding a saturated $NH_4Cl$ solution (1000 mL). The mixture was further acidified to approximately pH 1 by the addition. of a 5% HCl solution and stirring was continued for an additional 2 hours. The organic layer was separated, the aqueous layer extracted with $Et_2O$ and the combined organic layers were dried over anhydrous $MgSO_4$. The solvent was removed in vacuo and the residue purified over silica (using a isooctane/EtOAc 7:3 mixture as an eluent) to afford 65.5 g (92% yield) of the desired product as a light-yellow oil which was characterized as follows:

$R_f$ (isooctane/EtOAc, 7:3) 0.30;
UV (MeOH) absorption at 254 nm;
IR (KBr film): 2929, 2865, 2828, 1682, 1595, 1455, 1427, 1385, 1337, 1313, 1272, 1175, 1117, 982 and 795 $cm^{-1}$;
$^1H$ NMR (500 MHz, $CDCl_3$): 3.38 (2 H, t, J=5.9 Hz), 3.31 (3 H, s), 2.56-2.53 (2 H, m), 2.50-2.47 (4 H, m), 1.99-1.94 (2 H, m), 1.65-1.56 (4 H, m) ppm;
$^{13}C$ NMR (50 MHz, $CDCl_3$): 191.2 (C), 163.7. (C), 122.6 (C), 72.1 ($CH_2$), 58.6 ($CH_3$), 38.9 ($CH_2$), 37.8 ($CH_2$), 32.3 ($CH_2$), 29.4 ($CH_2$), 23.5 ($CH_2$) and 21.9 ($CH_2$) ppm; and
MS m/z (%): 230/228 ($M^+$—MeOH, <1/1), 200/188 (4/4), 181 (3), 149 (20), 131 (7), 121 (12), 107 (16), 93 (29), 91 (24), 79 (60), 77 (40), 65 (20), 51 (29) and 45 (100).

c) Preparation of 2-bromo-3-(4-methoxybutyl)-cyclohex-2-enol stereoisomers (3) and (3')

To a solution of 2-bromo-3-(4-methoxy-butyl)-cyclohex-2-enone (2) (32.0 g, 123 mmol) in dry toluene (480 mL) at −95° C. was added (S)-methyl-oxazaborolidi-none (for making isomer 3) or(R)-methyl-oxazaborolidinone (for making isomer 3") (1 M solution in toluene; 25 mL, 25 mmol). Catecholborane (1 M solution in toluene; 160 mL, 160 mmol) was added dropwise at −95° C. over a period of 10 hours and the reaction mixture stirred at −78° C. overnight. A 1 M NaOH solution (500 mL) was added and the temperature allowed to rise to room temperature. The organic layer was separated and the aqueous layer extracted with $Et_2O$. The combined organic layers were washed with a 1 M NaOH solution and dried over anhydrous $MgSO_4$. The solvent was removed in vacuo, and the resulting residue purified over silica (isooctane/EtOAc, 8:2) to afford 31.5 g (97% yield) of the desired product as a colorless oil which was characterized as follows:

$R_f$ (n-pentane/$Et_2O$, 7:3) 0.33;
optical rotation at room temperature: +71.6 (c=1.53, $CHCl_3$) for isomer (3); and −70.0 (c=1.13, $CHCl_3$) for isomer (3');.
IR (KBr film): 3418, 2935, 2864, 2828, 1645, 1455, 1387, 1337, 1264, 1165, 1118, 1078, 990, 970, 939, 813 and 733 $cm^{-1}$;
$^1H$ NMR (500 MHz, $CDCl_3$): 3.38 (2 H, t, J=6.4 Hz), 3.32 (3 H, s), 2.38 (1 H, d, J=3.8 Hz), 2.20 (2 H, dd, J=7.8, 7.8 Hz), 2.14 (2 H, ABt, J=17.3, 5.0 Hz), 2.07 (1 H, ABdd, J=17.3, 8.3, 5.6 Hz), 1.87-1.83 (2 H, m), 1.79-1.71 (1 H, m), 1.65-1.55 (3 H, m) and 1.51-1.45 (2 H, m) ppm;
$^{13}C$ NMR (50 MHz, $CDCl_3$): 140.5 (C), 122.9 (C), 72.5 ($CH_2$), 71.0 (CH), 58.5 ($CH_3$), 36.9 ($CH_2$), 32.0 ($CH_2$), 31.3 ($CH_2$), 29.3 ($CH_2$), 23.6 ($CH_2$), 18.3 ($CH_2$) ppm;
MS m/z (%): 246/244 ($M^+$—$H_2O$, <1/1), 214/212 (3/3), 165 (10), 133 (42), 123 (19), 105 (25), 91 (77), 79 (38), 67 (26), 55,(28), 53 (26), 45 (100) and 41 (33); and
elemental analysis: calculated for $C_{11}H_{19}BrO_2$: C, 50.20; H, 7.28; found: C, 50.17; H, 7.17.

d) preparation of 2-[2-bromo-1-(4-methoxybutyl)-cyclohexy-2-enyl]-N,N-dimethyl-acetamide stereoisomers (4) and (4')

To a solution of the relevant 2-bromo-3-(4-methoxybutyl)-cyclohex-2-enol isomer (3) or (3') (24.5 g, 93.1 mmol) in dry toluene (400 mL) was added N,N-dimethylacetamide dimethyl acetal (27.2 mL, 186.2 mmol). The reaction mixture was brought to reflux for 8 hours removing the generated MeOH by azeotropic distillation. The solvent was removed in vacuo and the residue purified over silica (using cyclohexane/EtOAc 1:1 as the eluent) to afford 29.4 g (95% yield) of the desired product as a light-yellow oil which was characterized as follows:

$R_f$ (isooctane/EtOAc, 1:1) 0.28;

optical rotation at room temperature: −41.4 (c=1.67, $CHCl_3$) for isomer (4); and +38.2 (c=0.96, $CHCl_3$) for isomer (4');

IR (KBr film): 2934, 2865, 1644, 1490, 1456, 1393, 1258, 1179, 1149, 1118, 968, 891, 861, 813 and 761 $cm^{-1}$;

$^1H$ NMR (500 MHz, $CDCl_3$): 6.13 (1 H, dd, J=4.2, 4.2 Hz), 3.38 (1 H, ABt, J=9.3, 6.5 Hz), 3.36 (1 H, ABt, J=9.3, 6.6 Hz), 3.31 (3 H, s), 3.06 (3 H, s), 2.92 (3 H, s), 2.59 (1 H, AB, J=14.9 Hz), 2.44 (1 H, AB, J=14.9 Hz), 2.32 (1 H, m), 2.09-1.98 (2 H, m), 1.77-1.71 (1 H, m), 1.67-1.52 (6 H, m) and 1.39-1.26 (2 H, m) ppm;

$^{13}C$ NMR (125 MHz, $CDCl_3$): 170.7 (C), 133.0 (C), 132.0 (CH), 72.6 ($CH_2$), 58.4 ($CH_3$), 43.8 (C), 39.7 ($CH_2$), 38.2 ($CH_2$), 38.0 ($CH_3$), 35.4 ($CH_3$), 30.7 ($CH_2$), 30.0 ($CH_2$), 27.8 ($CH_2$), 20.5 ($CH_2$), 18.6 ($CH_2$) ppm;

MS m/z (%): 252 ($M^+$- Br, 3), 91 (8), 87 (3), 72 (14) and 45 (100); and elemental analysis: calculated for $C_{15}H_{26}BrNO_2$: C, 54.22; H, 7.89; N, 4.22; found: C, 54.04; H, 8.05; N, 4.22.

e) Preparation of 2-[1-(4-methoxybutyl)-cyclohex-2-enyl]-N,N-dimethyl-acetamide stereoisomers (5) and (5')

To a solution of the relevant 2-[2-bromo-1-(4-methoxybutyl)-cyclohexy-2-enyl]-N,N-dimethyl-acetamide isomer (4) or (4') (37.0 g, 111 mmol) in THF (600 mL) was added tributyltin hydride (n-$Bu_3SnH$) (35.3 mL, 133. mmol) followed by azobisisobutyronitrile (1.8 g, 11.1 mmol). The reaction mixture was brought to reflux for 4 hours and the solvent removed in vacuo. The resulting residue was purified over silica (gradient elution: cyclohexane/EtOAc, 6:4 to EtOAc 100%) to afford 25.9 g (92% yield) of the desired product as a light-yellow oil which was characterized as follows:

$R_f$ (isooctane/EtOAc, 1:1) 0.24;

optical rotation at room temperature: −24.0 (c=1.59, $CHCl_3$) for isomer (5); and +22.9 (c=1.07, $CHCl_3$) for isomer (5');

IR (KBr film): 3013, 2931, 2864, 1637, 1490, 1449, 1384, 1261, 1114, 1061, 955 and 732 $cm^{-1}$;

$^1H$ NMR (500 MHz, $CDCl_3$): 5.62 (1 H, ABt, J=10.2, 3.7 Hz), 5.50 (1 H, AB, J=10.2 Hz), 3.32 (2 H, t, J=6.6 Hz), 3.26 (3 H, s), 2.96 (3 H, s), 2.87 (3 H, s), 2.40 (1 H, AB, J=14.2 Hz), 2.19 (1 H, AB, J=14.2 Hz), 1.93-1.84 (2 H, m), 1.63-1.43 (8 H, m) and 1.32-1.20 (2 H, m) ppm;

$^{13}C$ NMR (50 MHz, CDCl3): 171.3 (C), 134.3 (CH), 126.3 (CH), 72.6 ($CH_2$), 58.2 ($CH_3$), 40.9 ($CH_2$), 39.5 ($CH_2$), 38.1 ($CH_3$), 37.1 (C), 35.1 ($CH_3$), 32.5 ($CH_2$), 30.0 ($CH_2$), 24.7 ($CH_2$), 20.3 ($CH_2$) and 18.8 (CH2) ppm;

MS m/z (%): 253 ($M^+$, 5), 238 (10), 210 (2), 166 (12), 87 (59), 72 (47) and 45 (100);

elemental analysis: calculated for $C_{15}H_{27}NO_2$: C, 71.10; H, 10.74; N, 5.53; found: C, 70.97; H, 10.91; N, 5.45.

f) Preparation of 2-[1-(4-hydroxybutyl)-cyclohex-2-enyl]-N,N-dimethyl-acetamide stereoisomers (6) and (6')

To a solution of the relevant 2-[1-(4-methoxybutyl)-cyclohex-2-enyl]-N,N-dimethyl-acetamide isomer (5) or (5') (51.0 g, 201 mmol), NaI (60 g, 400 mmol) and 15-crown-5 (55 g, 250 mmol) in $CH_2Cl_2$ (1000 mL) at −30 ° C. was added dropwise $BBr_3$ (1 M solution in $CH_2Cl_2$; 241 mL, 241 mmol). The reaction mixture was stirred at −30° C. for 1 hour then a saturated $NaHCO_3$ solution (1000 mL) was added. The organic layer was separated and the aqueous layer extracted with $CH_2Cl_2$. The combined organic layers were washed with a saturated $Na_2SO_3$ solution and dried over anhydrous $MgSO_4$. The solvent was removed in vacuo and the residue purified over silica (gradient elution: $Et_2O$ 100% to $Et_2O$/MeOH, 95:5) to afford 39.9 g (83% yield) of the desired product as a viscous oil which was characterized as follows:

$R_f$ (EtOAc) 0.25;

optical rotation at room temperature: −21.4 (c=1.03, $CHCl_3$) for isomer (6); and +20.2 (c=0.99, $CHCl_3$) for isomer (6');

IR (KBr film): 3409, 3012, 2932, 2863, 1626, 1498, 1457, 1398, 1261, 1146, 1060, 923 and 730 $cm^{-1}$;

$^1H$ NMR (500 MHz, $CDCl_3$): 5.65 (1 H, ABt, J=10.2, 3.7 Hz), 5.48 (1 H, AB, J=10.2 Hz), 3.68-3.59 (2 H, m), 3.00 (3 H, s), 2.91 (3 H, s), 2.79 (1 H, br s), 2.47 (1 H, AB, J=13.9 Hz), 2.24 (1 H, AB, J=13.9 Hz), 1.98-1.89 (2 H, m) and 1.67-1.31 (10 H, m) ppm;

$^{13}C$ NMR (50 MHz, $CDCl_3$): 171.8 (C), 134.6 (CH), 126.8 (CH), 61.5 ($CH_2$), 40.3 ($CH_2$), 38.5 ($CH_3$), 38.3 ($CH_2$), 37.4 (C), 35.5 ($CH_3$), 35.4 ($CH_2$), 32.4 ($CH_2$), 25.0 ($CH_2$), 19.2 ($CH_2$) and 18.9 ($CH_2$) ppm;

MS m/z (%): 239 ($M^+$, 3), 196 (2), 166 (12), 121 (2), 87 (100), 79 (35), 72 (90) and 45 (25); and elemental analysis: calculated for $C_{14}H_{25}NO_2$: C, 70.25; H, 10.53; N, 5.85; found: C, 70.10; H, 10.49; N, 5.71.

g) Preparation of 4-(1-dimethylcarbamoylmethyl-cyclohex-2-enyl)-butyric acid stereoisomers (7) and (7')

To a solution of the relevant 2-[1-(4-hydroxybutyl)-cyclohex-2-enyl]-N,N-dimethyl-acetamide isomer (6) or (6') (13.7 g, 57.1 mmol) in DMF (200 mL) was added pyridinium dichromate (65.3 g, 241.0 mmol) and the mixture stirred at room temperature for 24 hours. The reaction mixture was poured into $H_2O$ (200 mL) and extracted with EtOAc (5×). The combined organic layers were washed with a saturated NaCl solution and dried over anhydrous $MgSO_4$. The solvent was removed in vacuo, the residual DMF was removed by vacuum distillation (Kugelrohr-type) to afford 13.3 g of the desired product which was used without further purification.

h) Preparation of 4-(1-methoxycarbonylmethyl-cyclohex-2-enyl)-butyric acid methyl ester stereoisomers (8) and (8')

The 4-(1-dimethylcarbamoylmethyl-cyclohex-2-enyl)-butyric acid isomer (7) or (7') from the previous step (13.3 g, 52.0 mmol; viscous oil) was dissolved in 1,4-dioxane (75 mL), KOH (1 M solution in $H_2O$; 225 mL) was added and the reaction mixture was heated at 200° C. (autoclave) for 4 hours. The reaction mixture was allowed to cool and then acidified using a 37% HCl solution. The aqueous layer was then repeatedly extracted with $CH_2Cl_2$. The combined organic layers were dried over anhydrous $MgSO_4$ and the solvent removed in vacuo. The resulting residue was dissolved in MeOH (200 mL) and a solution of $CH_2N_2$ in $Et_2O$ added at 0° C. with vigorous stirring until a yellow color persists. Excess $CH_2N_2$ was destroyed by the addition of silica gel, the mixture filtered, and the filtrate dried over anhydrous $MgSO_4$. The solvent was removed in vacuo and the resulting residue purified over silica (isooctane/EtOAc, 9:1) to afford 11.3 g (77% yield over 2 steps) of the desired product as a colorless oil which was characterized as follows:

$R_f$ (n-pentane/$Et_2O$, 8:2) 0.42;

optical rotation at room temperature: −1.7 (c=1.25, $CHCl_3$) for isomer (8); and +1.4 (c=1.4, $CHCl_3$) for isomer (8');

IR (KBr film): 3011, 2933, 2867, 1737, 1436, 1356, 1256, 1194, 1163, 1096, 1014, 882 and 732 $cm^{-1}$;

$^1$H NMR (500 MHz, $CDCl_3$): 5.70 (1 H, A̲Bt, J=10.2, 3.7 Hz), 5.49 (1 H, AB̲t, J=10.2, 1.9 Hz), 3.66 (3 H, s), 3.64 (3 H, s), 2.34 (1 H, AB, J=13.6 Hz), 2.31 (1 H, AB, J=13.6 Hz), 2.28 (2 H, t, J=7.5 Hz), 2.01-1.88 (2 H, m) and 1.65-1.38 (8 H, m) ppm;

$^{13}$C NMR (50 MHz, $CDCl_3$): 174.1 (C), 172.3 (C), 133.4 (CH), 127.5 (CH), 51.5 ($CH_3$), 51.3 ($CH_3$), 43.9 ($CH_2$), 39.2 ($CH_2$), 36.8 (C), 34.5 ($CH_2$), 32.3 ($CH_2$), 24.8 ($CH_2$), 19.5 ($CH_2$) and 18.8 ($CH_2$) ppm;

MS m/z (%): 254 ($M^+$, <1), 223 (5), 222 (9), 190 (5), 181 (26), 180 (42), 153 (37), 149 (44), 121 (43), 107 (44), 93 (97), 79 (100), 59 (64) and 42 (35); and elemental analysis: calculated for $C_{14}H_{22}O_4$: C, 66.12; H, 8.72; found: C, 66.24; H, 8.79.

(i) Preparation of 2-hydroxy-spiro[5.5]undecan-2,7-diene-3-carboxylic acid methyl ester stereoisomers (9) and (9')

To a solution of the relevant 4-(1-methoxycarbonylmethyl-cyclohex-2-enyl)-butyric acid methyl ester isomer (8) or (8') (31.0 g, 122 mmol) in dry THF (580 mL) at −78° C. was added dropwise i-$Pr_2NLi$ (2 M solution in n-heptane; 122 mL, 244 mmol). The reaction mixture was allowed to warm to room temperature and stirred for 2 hours. A saturated $NH_4Cl$ solution (700 mL) was added and the aqueous layer repeatedly extracted with $Et_2O$. The combined organic layers were dried over anhydrous $MgSO_4$ and the solvents removed in vacuo. The resulting residue was purified over silica (n-pentane/$Et_2O$, 95:5) to afford 24.7 g (91% yield) of the desired product as white crystals which were characterized as follows:

melting point: 46° C.;

$R_f$ (n-pentane/$Et_2O$, 95:5) 0.50;

optical rotation at room temperature: −19.1 (c=1.05, $CHCl_3$) for isomer (9); and +17.4 (c=1.15, $CHCl_3$) for isomer (9');

UV (MeOH) 255 nm;

IR (KBr): 3061, 2994, 2949, 2924, 2856, 1665, 1623, 1444, 1414, 1380, 1333, 1294, 1282, 1261, 1212, 1179, 1132, 1087, 1048, 1024, 986, 960, 926, 905, 813 and 733 $cm^{-1}$;

$^1$H NMR (500 MHz, $CDCl_3$): 12.1 (1 H, s), 5.68 (1 H, dt, J=10.1, 3.7 Hz), 5.45 (1 H, dt, J=10.1, 2.0 Hz), 3.76 (3 H, s), 2.32-2.22 (2 H, m), 2.16 (1 H, A̲Bm, J=18.3 Hz), 2.12 (1 H, AB̲m, J=18.3 Hz), 2.00-1.94 (2 H, m), 1.73-1.50 (4 H, m) and 1.44-1.38 (2 H, m) ppm;

$^{13}$C NMR (75 MHz, $CDCl_3$): 172.8 (C), 170.8 (C), 134.0 (CH), 127.1 (CH), 96.5 (CH), 51.4 ($CH_3$), 40.8 ($CH_2$), 34.1 ($CH_2$), 33.4 ($CH_2$), 25.4 ($CH_2$), 19.3 ($CH_2$) and 18.7 ($CH_2$) ppm;

MS m/z (%) 222 ($M^+$, 4), 194 (14), 128 (15), 107 (14), 94 (68), 79 (100), 77 (36), 65 (20), 55 (36) and 41 (45); and elemental analysis: calculated for $C_{13}H_{18}O_3$: C, 70.24; H, 8.16; found: C, 70.15; H, 8.18.

j) Preparation of spiro[5.5]undec-7-en-2-one stereoisomers (10) and (10')

To a solution of the relevant 2-hydroxy-spiro[5.5]undecan-2,7-diene-3-carboxylic acid methyl ester isomer (9) or (9') (19.0 g, 85.0 mmol) in DMSO (66 mL) was added NaCl (5.5 g, 93.5 mmol) and $H_2O$ (4.6 mL, 255 mmol). The reaction mixture was heated at 160° C. for 6 hours then cooled and poured into $H_2O$ (100 mL). The aqueous layer was extracted with $Et_2O$ (5×) and the combined organic layers dried over anhydrous $MgSO_4$. The solvent was removed in vacuo and the resulting residue purified over silica (n-pentane/$Et_2O$, 95:5) to afford 13.3 g (95% yield) of the desired product as a colorless oil which was characterized as follows:

$R_f$ (n-pentane/$Et_2O$, 9:1) 0.36;

optical rotation at room temperature: −67.0 (c=1.49, $CHCl_3$) for isomer (10); and +68.9 (c=1.02, $CHCl_3$) for isomer (10');

IR (KBr film): 3014, 2932, 2873, 1713, 1446, 1422, 1345, 1312, 1287, 1227, 1204, 1064, 1009, 923, 887, 730 and 529 $cm^{-1}$;

$^1$H NMR (500 MHz, $CDCl_3$): 5.64 (1 H, A̲Bt, J=10.1, 3.7 Hz), 5.42 (1 H, AB̲(fs)), J=10.1 Hz), 2.32-2.26 (2 H, m), 2.21 (1 H, A̲B, J=13.9 Hz), 2.21 (1 H, AB̲, J=13.9 Hz), 1.95-1.82 (4 H, m), 1.72 (1 H, m), 1.63-1.52 (3 H, m) and 1.51-1.40 (2 H, m) ppm;

$^{13}$C NMR (50 MHz, $CDCl_3$): 211.6 (C), 133.7 (CH), 126.9 (CH), 52.8 ($CH_2$), 40.9 ($CH_2$), 39.4 (C), 36.9 ($CH_2$), 33.4 ($CH_2$), 24.9 ($CH_2$), 21.6 ($CH_2$) and 18.3 ($CH_2$) ppm;

MS m/z (%): 164 ($M^+$, 61), 146 (8), 136 (11), 131 (17), 121 (39), 107 (89), 91 (41), 79 (100), 67 (17), 55 (18) and 42 (33); and elemental analysis: calculated for $C_{11}H_{16}O$: C, 80.44; H, 9.82; found: C, 80.33; H, 9.95.

k) Preparation of 1,4-dioxa-dispiro[4.1.5.3]pentadec-8-ene stereoisomers (11) and (11')

To a solution of the relevant spiro[5.5]undec-7-en-2-one isomer (10) or (10') (10 g, 61 mmol) in toluene (150 mL) was added HO($CH_2$)$_2$OH (10 mL, 179 mmol) and p-toluenesulfonic acid $H_2O$ (0.57 g, 3 mmol). The reaction mixture was brought to reflux and the $H_2O$ generated was removed by azeotropic distillation (using a Dean-Stark separator). The reaction mixture was then cooled and washed with a saturated $NaHCO_3$ solution. The aqueous phase was extracted with $Et_2O$ and the combined organic layers dried over anhydrous $Na_2SO_4$. The solvent was removed in vacuo and the resulting residue purified over silica (isooctane/EtOAc, 95:5) to afford 12.1 g (95% yield) of the desired product which was characterized as follows:

$R_f$ (isooctane/EtOAc, 95:5) 0.34;

optical rotation at room temperature: −25.8 (c=1.41, $CHCl_3$) for isomer (11); and +25.2 (c=1.03, $CHCl_3$) for isomer (11');

IR (KBr film): 2933, 2871, 2837, 1643, 1147, 1360, 1317, 1283, 1241, 1219, 1178, 1156, 1074, 1051, 1013, 947, 926, 888, 854, 821 and 732 $cm^{-1}$;

$^1$H NMR (500 MHz, $CDCl_3$): 5.67 (1 H, A̲B, J=10.2 Hz), 5.59 (1 H, AB̲t, J=10.2, 3.6 Hz), 3.94-3.89 (4 H, m), 1.96-1.92 (2 H, m), 1.68-1.50 (10 H, m) and 1.40-1.30 (2 H, m) ppm;

$^{13}$C NMR (50 MHz, CDCl$_3$): 136.2 (CH), 125.6 (CH), 109.3 (C), 64.1 (CH$_2$), 63.9 (CH$_2$), 45.4 (CH$_2$), 37.3 (CH$_2$), 35.8 (C), 35.0 (CH$_2$), 25.5 (CH$_2$), 19.5 (CH$_2$) and 18.9 (CH$_2$) ppm; and MS m/z (%): 208 (M$^+$, 12), 193 (14), 165 (70), 125 (17), 99 (100), 86 (62), 79 (38) and 41 (32).

As mentioned herein above, the corresponding 1,4-dithia-dispiro[4.1.5.3]pentadec-8-ene stereoisomers are also accessible in step (k) while using HS(CH$_2$)$_2$SH as an alternative reactant.

Compounds which are comprised in category I of the present invention include, but are not limited to, the E-isomers of 5-[2-(2-R$^{1b}$-substituted-spiro[4.5]dec-7-ylidene)-ethylidene]-cyclohexane-1,3-diols having the following structural formula:

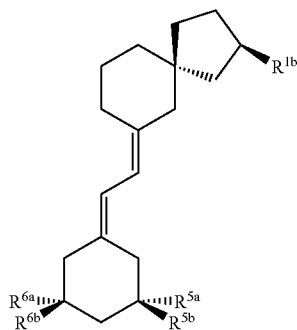

wherein the R$^{1b}$ substitutions at carbon-20 are outlined herein below in Table 1.

TABLE 1

| No. | R$^{1b}$ | R$^{5a}$ | R$^{5b}$ | R$^{6a}$ | R$^{6b}$ |
|---|---|---|---|---|---|
| 1 | 4-hydroxy-4-methylpentyl | H | OH | OH | H |
| 2 | 5-hydroxy-5-methylhex-2-yl | H | OH | OH | H |
| 3 | 6-hydroxy-6-methylhept-2-yl | H | OH | OH | H |
| 4 | 5-hydroxy-6-methylhept-2-yl | H | OH | OH | H |
| 5 | 1-hydroxy-5,5-dimethylhexyl | H | OH | OH | H |
| 6 | 7-hydroxy-7-methyloct-4-en-2-yl | H | OH | OH | H |
| 7 | 7-hydroxy-7-ethylnon-4-en-2-yl | H | OH | OH | H |
| 8 | 7-hydroxy-7-ethylnon-4-en-2-yl | H | OH | OH | H |
| 9 | 7-hydroxy-7-ethylnon-3,5-dien-2-yl | H | OH | OH | H |
| 10 | 5-hydroxy-5-methylhex-3-ynyl | H | OH | OH | H |
| 11 | 4-(2-methyl-oxyranyl)-but-3-ynyl | H | OH | OH | H |
| 12 | 6-hydroxy-6-methylhept-3-yn-2-yl | H | OH | OH | H |
| 13 | 5-(2-methyloxyranyl)-pent-4-yn-2-yl | H | OH | OH | H |
| 14 | 5-hydroxy-5-ethylhept-3-ynyl | H | OH | OH | H |
| 15 | 6-hydroxy-6-ethyloctyn-4-yn-2-yl | H | OH | OH | H |
| 16 | 4-hydroxy-4-methylpentyl | OH | H | OH | H |
| 17 | 5-hydroxy-5-methylhex-2-yl | OH | H | OH | H |
| 18 | 6-hydroxy-6-methylhept-2-yl | OH | H | OH | H |
| 19 | 5-hydroxy-6-methylhept-2-yl | OH | H | OH | H |
| 20 | 1-hydroxy-5,5-dimethylhexyl | OH | H | OH | H |
| 21 | 7-hydroxy-7-methyloct-4-en-2-yl | OH | H | OH | H |
| 22 | 7-hydroxy-7-ethylnon-4-en-2-yl | OH | H | OH | H |
| 23 | 7-hydroxy-7-ethylnon-4-en-2-yl | OH | H | OH | H |
| 24 | 7-hydroxy-7-ethylnon-3,5-dien-2-yl | OH | H | OH | H |
| 25 | 5-hydroxy-5-methylhex-3-ynyl | OH | H | OH | H |
| 26 | 4-(2-methyl-oxyranyl)-but-3-ynyl | OH | H | OH | H |
| 27 | 6-hydroxy-6-methylhept-3-yn-2-yl | OH | H | OH | H |
| 28 | 5-(2-methyloxyranyl)-pent-4-yn-2-yl | OH | H | OH | H |
| 29 | 5-hydroxy-5-ethylhept-3-ynyl | OH | H | OH | H |
| 30 | 6-hydroxy-6-ethyloctyn-4-yn-2-yl | OH | H | OH | H |
| 31 | 4-hydroxy-4-methylpentyl | H | OH | OH | H |
| 32 | 5-hydroxy-5-methylhex-2-yl | H | OH | OH | H |
| 33 | 6-hydroxy-6-methylhept-2-yl | H | OH | OH | H |
| 34 | 5-hydroxy-6-methylhept-2-yl | H | OH | OH | H |
| 35 | 1-hydroxy-5,5-dimethylhexyl | H | OH | OH | H |
| 36 | 7-hydroxy-7-methyloct-4-en-2-yl | H | OH | OH | H |
| 37 | 7-hydroxy-7-ethylnon-4-en-2-yl | H | OH | OH | H |
| 38 | 7-hydroxy-7-ethylnon-4-en-2-yl | H | OH | OH | H |
| 39 | 7-hydroxy-7-ethylnon-3,5-dien-2-yl | H | OH | OH | H |
| 40 | 5-hydroxy-5-methylhex-3-ynyl | H | OH | OH | H |
| 41 | 4-(2-methyl-oxyranyl)-but-3-ynyl | H | OH | OH | H |
| 42 | 6-hydroxy-6-methylhept-3-yn-2-yl | H | OH | OH | H |
| 43 | 5-(2-methyloxyranyl)-pent-4-yn-2-yl | H | OH | OH | H |
| 44 | 5-hydroxy-5-ethylhept-3-ynyl | H | OH | OH | H |
| 45 | 6-hydroxy-6-ethyloctyn-4-yn-2-yl | H | OH | OH | H |
| 46 | 4-hydroxy-4-methylpentyl | OH | H | H | OH |
| 47 | 5-hydroxy-5-methylhex-2-yl | OH | H | H | OH |
| 48 | 6-hydroxy-6-methylhept-2-yl | OH | H | H | OH |
| 49 | 5-hydroxy-6-methylhept-2-yl | OH | H | H | OH |
| 50 | 1-hydroxy-5,5-dimethylhexyl | OH | H | H | OH |
| 51 | 7-hydroxy-7-methyloct-4-en-2-yl | OH | H | H | OH |
| 52 | 7-hydroxy-7-ethylnon-4-en-2-yl | OH | H | H | OH |
| 53 | 7-hydroxy-7-ethylnon-4-en-2-yl | OH | H | H | OH |
| 54 | 7-hydroxy-7-ethylnon-3,5-dien-2-yl | OH | H | H | OH |
| 55 | 5-hydroxy-5-methylhex-3-ynyl | OH | H | H | OH |
| 56 | 4-(2-methyl-oxyranyl)-but-3-ynyl | OH | H | H | OH |
| 57 | 6-hydroxy-6-methylhept-3-yn-2-yl | OH | H | H | OH |
| 58 | 5-(2-methyloxyranyl)-pent-4-yn-2-yl | OH | H | H | OH |
| 59 | 5-hydroxy-5-ethylhept-3-ynyl | OH | H | H | OH |
| 60 | 6-hydroxy-6-ethyloctyn-4-yn-2-yl | OH | H | H | OH |

Other compounds which comprise Category I of the present invention have the structural formula:

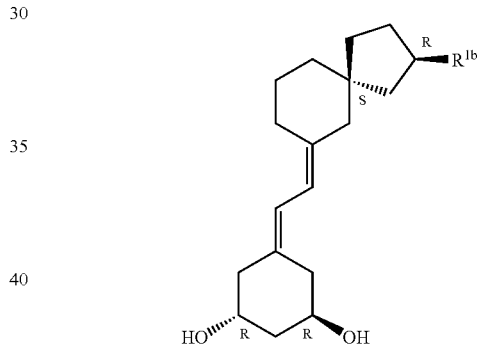

having the assigned (S,R) stereochemistry in the CF-Ring system. Non-limiting examples of R$^{1b}$ are found in Table 2 herein below.

TABLE 2

| No. | R$^{1b}$ |
|---|---|
| 1 | n-hexyl |
| 2 | 1-methylpentyl |
| 3 | 2-methylpentyl |
| 4 | 3-methyl-pentyl |
| 5 | 4-methylpentyl |
| 6 | 1,1-dimethylbutyl |
| 7 | 1,2-dimethylbutyl |
| 8 | 1,3-dimethylbutyl |
| 9 | 2,2-dimethylbutyl |
| 10 | 2,3-dimethylbutyl |
| 11 | 3,3-dimethylbutyl |
| 12 | 1-ethylbutyl |
| 13 | 2-ethylbutyl |
| 14 | n-heptyl |
| 15 | 1-methylhexyl |
| 16 | 2-methyl-hexyl |
| 17 | 3-methylhexyl |
| 18 | 4-methylhexyl |

TABLE 2-continued

| No. | $R^{1b}$ |
|---|---|
| 19 | 5-methylhexyl |
| 20 | 1,1-dimethyl-pentyl |
| 21 | 1,2-dimethylpentyl |
| 22 | 1,3-dimethylpentyl |
| 23 | 1,4-dimethylpentyl |
| 24 | 2,2-dimethylpentyl |
| 25 | 2,3-dimethylpentyl |
| 26 | 4,4-dimethylpentyl |
| 27 | 1-hydroxy-4-methylpentan-1-yl |
| 28 | 2-hydroxy-4-methylpentan-1-yl |
| 29 | 3-hydroxy-4-methylpentan-1-yl |
| 30 | 4-hydroxy-4-methylpentan-1-yl |
| 31 | 1-hydroxy-5-methylhexan-2-yl |
| 32 | 2-hydroxy-5-methylhexan-2-yl |
| 33 | 3-hydroxy-5-methylhexan-2-yl |
| 34 | 4-hydroxy-5-methylhexan-2-yl |
| 35 | 5-hydroxy-5-methylhexan-2-yl |
| 36 | 1-hydroxy-6-methylheptan-2-yl |
| 37 | 2-hydroxy-6-methylheptan-2-yl |
| 38 | 3-hydroxy-6-methylheptan-2-yl |
| 39 | 4-hydroxy-6-methylheptan-2-yl |
| 40 | 5-hydroxy-6-methylheptan-2-yl |
| 41 | 6-hydroxy-6-methylheptan-2-yl |
| 42 | 1-hydroxy-1,5-dimethyl-hexan-1-yl |
| 43 | 1-hydroxy-5,5-dimethyl-hexan-1-yl |
| 44 | 4-methylpent-2-enyl |
| 45 | 5-methylhex-2-enyl |
| 46 | 5-methylhex-3-enyl |
| 47 | 4-ethylhex-2-enyl |
| 48 | 6-methylhept-2-enyl |
| 49 | 6-methylhept-3-enyl |
| 50 | 6-methylhept-4-enyl |
| 51 | 7-methyloct-4-en-2-yl |
| 52 | 6-ethyloct-2-enyl |
| 53 | 6-ethyloct-3-enyl |
| 54 | 6-ethyloct-4-enyl |
| 55 | 4-hydroxy-4-methylpent-2-enyl |
| 56 | 4-cyano-4-methylpent-2-enyl |
| 57 | 5-hydroxy-5-methylhex-2-enyl |
| 58 | 5-hydroxy-5-methylhex-3-enyl |
| 59 | 4-hydroxy-4-ethylhex-2-enyl |
| 60 | 6-hydroxy-6-methylhept-2-enyl |
| 61 | 6-hydroxy-6-methylhept-3-enyl |
| 62 | 6-hydroxy-6-methylhept-4-enyl |
| 63 | 7-hydroxy-7-methyloct-4-en-2-yl |
| 64 | 7-hydroxy-7-methyloct-3,5-dien-2-yl |
| 65 | 6-hydroxy-6-ethyloct-2-enyl |
| 66 | 6-hydroxy-6-ethyloct-3-enyl |
| 67 | 6-hydroxy-6-ethyloct-4-enyl |
| 68 | 7-hydroxy-7-ethylnon-3,5-dien-2-yl |
| 69 | pent-2-ynyl |
| 70 | hex-2-yn-2-yl |
| 71 | hex-3-yn-2-yl |
| 72 | hex-4-yn-2-yl |
| 73 | 5-methylhex-3-ynyl |
| 74 | 6-methylhept-3-yn-2-yl |
| 75 | 5-ethylhept-3-ynyl |
| 76 | 6-ethyloctyn-4-yn-2-yl |
| 77 | 5-hydroxy-5-methylhex-3-ynyl |
| 78 | 4-(2-methyl-oxyranyl)-but-3-ynyl |
| 79 | 6-hydroxy-6-methylhept-3-yn-2-yl |
| 80 | 5-(2-methyl-oxyranyl)-pent-4-yn-2-yl |
| 81 | 5-hydroxy-5-ethylhept-3-ynyl |
| 82 | 6-hydroxy-6-ethyloctyn-4-yn-2-yl |

Scheme II below outlines a sequence of eight process steps for the preparation of intermediates and precursors containing the $R^{1a}$ and/or $R^{1b}$ substituents of the F ring which are comprised in the compounds of the above categories of the present invention. In the example below, intermediate 14a is used to prepare compounds which are comprised in categories I and II of the present invention, whereas intermediate 14b is used to prepare compounds which are comprised in categories III and IV of the present invention. Each step of scheme II will now be illustrated in details, based on specific starting compounds, reactive agents, catalysts, solvents, temperature ranges and the like, but the skilled person will understand that the specific materials and conditions disclosed herein may be replaced with similar or equivalent materials and conditions without significantly altering the resulting product of the relevant step. In particular the steps of scheme II are illustrated below starting from 1,4-dioxa-dispiro intermediates, but the skilled person understands that a similar sequence of reactions can be performed successfully while starting from the corresponding 1,4-dithia-dispiro intermediates.

Scheme II

In a first step (a), the relevant 1,4-dioxa-dispiro[4.1.5.3]pentadec-8-ene stereoisomer (11) or alternatively the corresponding 1,4-dithia-dispiro[4.1.5.3]pentadec-8-ene stereoisomer (not shown in the scheme) obtained in the eleventh and last step of scheme (I) is submitted to oxidative cleavage by any suitable method, for instance by ozonolysis at low temperature and optionally in the presence of a catalyst. More specifically, said step may be performed in two sub-steps, first including complex formation in the presence of ozone and a solvent, and secondly with use of trimethylphosphite as a reducing agent:

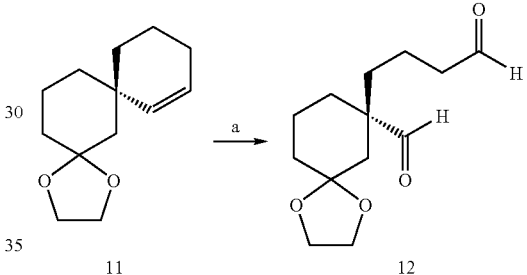

(preferred reagents and conditions for step (a): first (i) $O_3$, methanol as a solvent; temperature about −90° C. to −70° C., more specifically −78° C.; then (ii) $P(OCH_3)_3$; temperature ranging from about −78° C. to about −25° C.).

In a second step (b), the 7-(4-oxo-butyl)-1,4-dioxaspiro[4.5]decane-7-carbaldehyde stereoisomer (respectively the 7-(4-oxo-butyl)-1,4-dithiaspiro[4.5]decane-7-carbaldehyde stereoisomer, not shown in the scheme) resulting from step (a) is submitted to an aldol condensation preferably in the presence of a suitable solvent and preferably in the presence of an effective amount of a suitable basic catalyst such as, but not limited to, a triflate reagent:

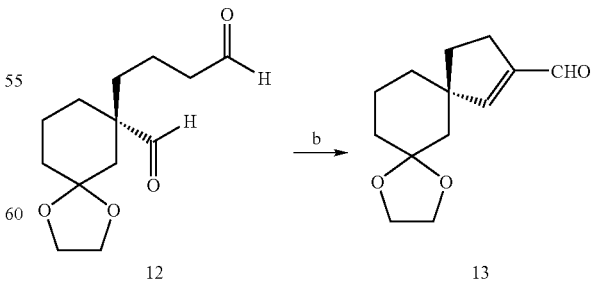

(preferred reagents and conditions for step (b): $(PhCH_2)_2NH_2^+CF_3CO_2^-$ as a catalyst, THF as a solvent; temperature ranging from about 10° C. to about 40° C.).

In a third step (c), the 1,4-dioxa-dispiro[4.1.4.3]tetradec-8-ene-9-carbaldehyde stereoisomer (respectively the 1,4-dioxa-dispiro[4.1.4.3]tetradec-8-ene-9-carbaldehyde stereoisomer, not shown in the scheme) resulting from step (b) is reduced in the presence of a suitable reducing agent such as, but not limited to, hydrogen and in the presence of a suitable solvent and optionally in the presence of an effective amount of a suitable catalyst such as platinum supported onto a carrier:

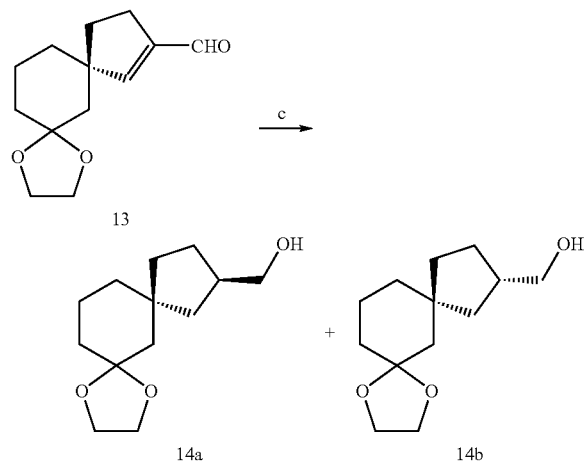

(preferred reagents and conditions for step (c) are: $H_2$ as a reducing agent, Pt/C as a catalyst; ethyl acetate as a solvent; temperature ranging from about 10° C. to about 40° C.).

In a fourth step (d), one (1,4-dioxa-dispiro[4.1.4.3]tetradec-9-yl) methanol stereoisomer (respectively one (1,4-dithia-dispiro[4.1.4.3]tetradec-9-yl) methanol stereoisomer) resulting from step (c) is activated for nucleophilic displacement, e.g. sulfonated in the presence of a sulfonating agent and a solvent and optionally in the presence of an effective amount of a suitable catalyst:

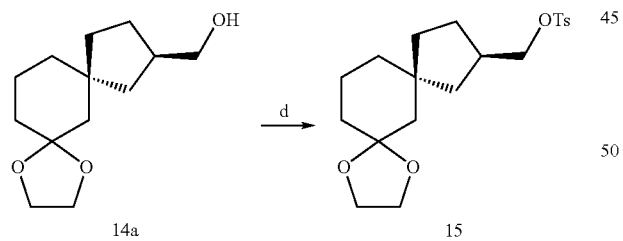

(preferred reagents and conditions for step (d): toluenesulfonyl or methanesulfonyl chloride as a sulfonating agent, dimethylaminopyridine (DMAP) as a catalyst, pyridine as a solvent; temperature ranging from about 10° C. to about 40° C.).

In a fifth step (e), the toluene-4-sulfonic acid 1,4-dioxa-dispiro[4.1.4.3]tetradec-9-ylmethyl ester stereoisomer (respectively the toluene-4-sulfonic acid 1,4-dithia-dispiro[4.1.4.3]tetradec-9-ylmethyl ester stereoisomer) resulting from step (d) is submitted to a halo-de-sulfonyloxy-substitution somewhat similar to a Finkelstein reaction, preferably in the presence of a suitable solvent:

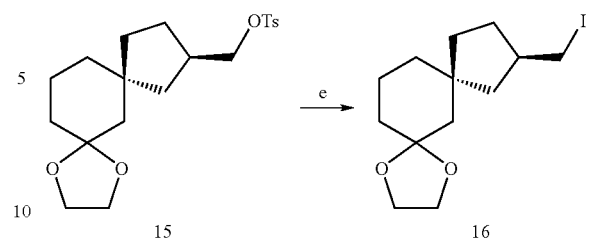

(preferred reagents and conditions for step (e): NaI, $NaHCO_3$, $CH_3CN$ as a solvent; reflux temperature of the solvent; substitution may also be effected with a bromide or a chloride instead of an iodide).

In a sixth step (f), the 9-iodomethyl-1,4-dioxa-dispiro[4.1.4.3]tetradec-9-yl methyl ester stereoisomer (respectively the 9-iodomethyl-1,4-dithia-dispiro[4.1.4.3] tetradec-9-yl methyl ester stereoisomer) resulting from step (e) is submitted to a 1,4-addition reaction by means of an α,β-ethylenically unsaturated carboxylic acid ester such as, but not limited to, a $C_1$-$C_8$ alkyl acrylate or $C_1$-$C_8$ alkyl methacrylate, preferably in the presence of a suitable solvent and optionally in the presence of a suitable catalyst:

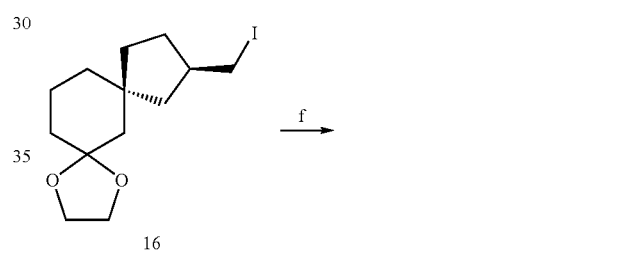

(preferred reagents and conditions for step (f): $CH_2$=$CHCO_2C_2H_5$, Zn and $NiCl_2.6H_2O$ as catalyst components, pyridine as a solvent; temperature ranging from about 10° C. to about 40° C.).

In a seventh step (g), the 4-(1,4-dioxa-dispiro[4.1.4.3]tetradec-9-yl)-butyric acid ethyl ester stereoisomer (respectively the 4-(1,4-dithia-dispiro[4.1.4.3]tetradec-9-yl)-butyric acid ethyl ester stereoisomer) resulting from step (f) is alkylated, e.g. by reaction with a suitable organometallic species, preferably a Grignard reagent, preferably in the presence of a suitable solvent:

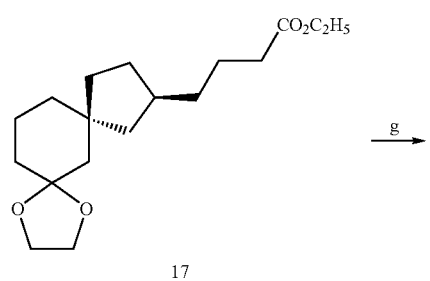

17

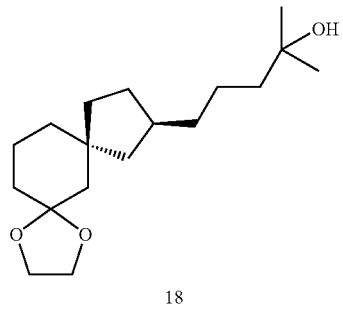

18

(preferred reagents and conditions for step (g): CH$_3$MgBr as a Grignard reagent, THF as a solvent; temperature ranging from about 0° C. to about 40° C.).

In an eighth step (h), the 5-(1,4-dioxa-dispiro[4.1.4.3]tetradec-9-yl)-2-methyl pentanol stereoisomer (respectively the 5-(1,4-dithia-dispiro[4.1.4.3]tetradec-9-yl)-2-methyl pentanol stereoisomer) resulting from step (f) is hydrolysed, preferably under acidic conditions and in the presence of an aqueous solvent:

(preferred reagents and conditions for step (h): p-toluenesulfonic acid as an acidic catalyst, acetone/water as a solvent medium; temperature ranging from about 0° C. to about 40° C.).

For the ease of understanding and the completion of the disclosure of other stereoisomers which are also available by this methodology, scheme II' hereunder provides a full depiction of a similar synthetic route starting from the other 1,4-dioxa-dispiro[4.1.5.3]pentadec-8-ene stereoisomer (11') leading to compounds of categories V, VI, VII and VIII. The skilled person understands that a similar sequence of reactions can also be performed successfully while starting from the corresponding 1,4-dithia-dispiro intermediates.

Scheme II'

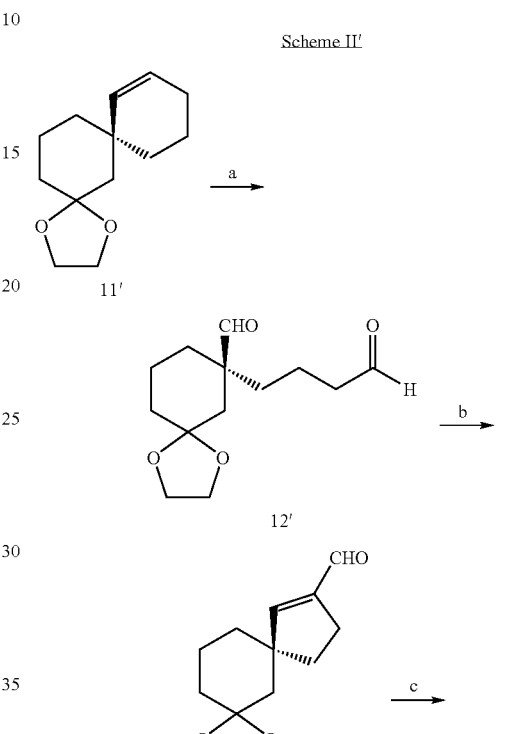

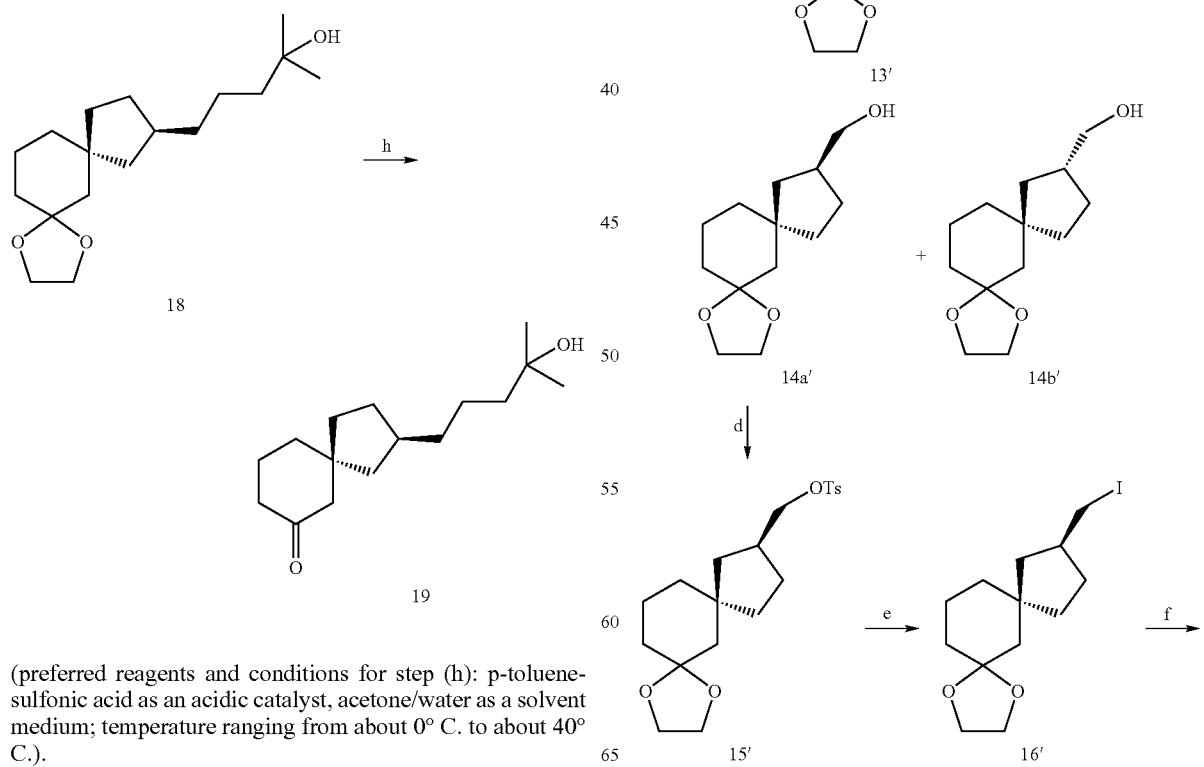

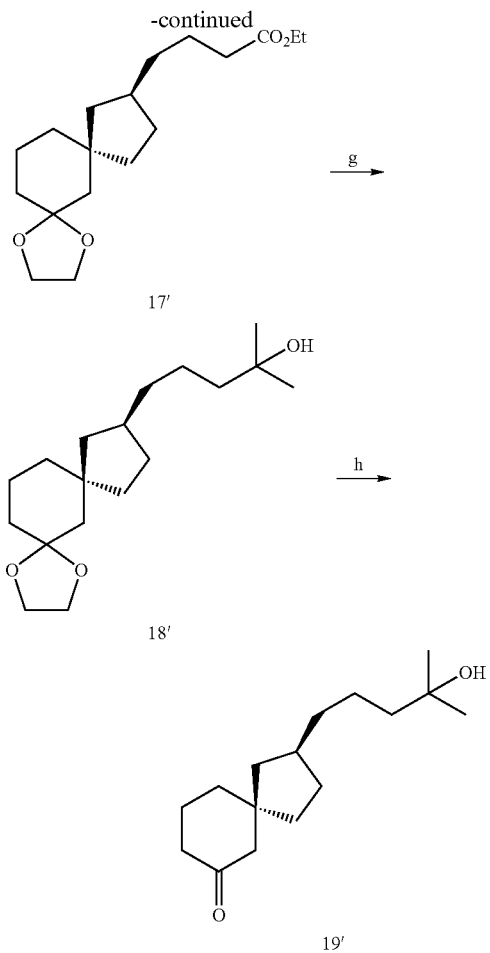

EXAMPLE 2

Preparation of 2-(4-hydroxy-4-methylpentyl)-spiro[4.5]decan-7-one (19) and 2-(4-hydroxy-4-methylpentyl)-spiro[4.5]decan-7-thione The preparation of 2-(4-hydroxy-4-methylpentyl)-spiro[4.5]decan-7-one was effected via the principles of the eight steps synthetic route described above, and more especially as outlined hereunder.

a) Preparation of 7-(4-oxo-butyl)-1,4-dioxaspiro[4.5]decane-7-carbaldehyde (12)

Ozone gas was bubbled into a solution of 1,4-dioxa-dispiro[4.1.5.3]pentadec-8-ene, 11, (3.0 g, 14.4 mmol) in MeOH (30 mL) at −78° C. Once the reaction was completed as determined by thin layer chromatography (TLC), argon gas was bubbled through the reaction solution for 10 minutes after which phosphorous acid trimethyl ester (3 mL, 25.4 mmol) is added. The temperature was allowed to rise to −40° C. and stirring was continued for an additional 30 minutes. The solvent was then removed under reduced pressure to afford the desired product which was used without further purification in the next step.

b) Preparation of 1,4-dioxa-dispiro[4.1.4.3]tetradec-8-ene-9-carbaldehyde (13)

To the 7-(4-oxo-butyl)-1,4-dioxaspiro[4.5]decane-7-carbaldehyde, 12, obtained in the previous step, was added dibenzylammonium trifluoroacetate (0.4 M solution in THF; 12 mL, 4.8 mmol). The resulting mixture was stirred at room temperature for 3 hours after which the solvent was removed in vacuo. The resulting residue was purified over silica (cyclohexane/EtOAc, 8:2 mixture) to provide 2.3 g (72% yield) of the desired product as a colorless oil which was characterized as follows:

$R_f$ (isooctane/EtOAc, 7:3) 0.33;

optical rotation at room temperature: −7.6 (c=1.13, CHCl$_3$) for isomer (13); and +7.3 (c=0.89, CHCl$_3$) for isomer (13');

UV (MeOH) absorption at 239 nm;

IR (KBr film): 2939, 2889, 1681, 1618, 1475, 1448, 1363, 1313, 1243, 1213, 1168, 1110, 1063, 1050, 948, 827 and 712 cm$^{-1}$;

$^1$H NMR (500 MHz, CDCl$_3$): 9.75 (1 H, s), 7.00 (1 H, s), 3.91-3.90.(4 H, m), 2.49-2.46 (2 H, m), 1.87 (1 H, ABt, J=13.2, 7.4 Hz), 1.81 (1 H, ABt, J=13.0, 7.0 Hz), 1.74-1.53 (7 H, m) and 1.40 (1 H, m) ppm;

$^{13}$C NMR (75 MHz, CDCl$_3$): 190.9 (CH), 160.0 (CH), 145.1 (C), 108.7 (C), 64.3 (CH$_2$), 64.2 (CH$_2$), 51.1 (C), 44.2 (CH$_2$), 37.4 (CH$_2$), 35.8 (CH$_2$), 34.6 (CH$_2$), 26.5 (CH$_2$) and 20.9 (CH$_2$) ppm; and MS m/z (%): 222 (M$^+$, 9), 195 (19), 179 (25), 151 (9), 131 (6), 107 (11), 99 (100), 86 (70), 79 (31), 77 (34) and 55 (33).

c) Preparation of (1,4-dioxa-dispiro[4.1.4.3]tetradec-9-yl)methanol isomers (14a) and (14b)

A mixture of 1,4-dioxa-dispiro[4.1.4.3]tetradec-8-ene-9-carbaldehyde (13) (500 mg, 2.5 mmol) and Pt (5 weight-% on activated carbon; 488 mg, 0.125 mmol) in EtOAc (10 mL) was placed under H$_2$ (1 atm) and vigorously stirred at room temperature for 36 hours. The mixture was then filtered through Celite and the filtrate was concentrated in vacuo to afford an oil which was purified over silica (eluent: isooctane/EtOAc mixtures, elution gradient from 7:3 to 1:1) to afford a 1:1 mixture of epimeric alcohols (450 mg, 88%). The epimeric alcohols were separated by HPLC over silica (toluene/EtOAc, 8:2). Characterization of the isomer (14a) was as follows:

$R_f$ (isooctane/EtOAc, 1:1) 0.30;

optical rotation at room temperature: +4.4 (c=1.39, CHCl$_3$);

IR (KBr film): 3420, 2934, 2868, 1447, 1363, 1323, 1279, 1238, 1172, 1111, 1088, 1068, 1044, 946, 896, 856 and 826 cm$^{-1}$;

$^1$H NMR (500 MHz, CDCl$_3$): 3.89 (4 H, s), 3.49 (1 H, ABd, J=10.4, 6.6 Hz), 3.48 (1 H, ABd, J=10.4, 6.9 Hz), 2.17 (1 H, m), 1.79-1.71 (3 H, m), 1.59-1.47 (8 H, m), 1.34-1.26 (3 H, m) and 1.07 (1 H, dd, J=13.1, 9.5 Hz) ppm;

$^{13}$C NMR (75 MHz, CDCl$_3$): 109.5 (C), 67.9 (CH$_2$), 64.1 (CH$_2$), 64.0 (CH$_2$), 46.1 (CH$_2$), 43.9 (C), 42.1 (CH$_2$), 40.7 (CH), 38.3 (CH$_2$), 36.1 (CH), 35.0 (CH$_2$), 27.3 (CH$_2$) and 20.8 (CH$_2$) ppm;

MS m/z (%): 226 (M$^+$, <1), 195 (3), 183 (73), 165 (3), 121 (4), 113 (9), 99 (100), 86 (26), 79 (10), 67 (7), 55 (14) and 41 (12); and elemental analysis: calculated for C$_{13}$H$_{22}$O$_3$: C, 68.99; H, 9.80; found: C, 68.81; H, 9.90.

Additionally, characterization of the isomer (14b) was as follows:

$R_f$ (isooctane/EtOAc, 1:1) 0.31;

optical rotation at room temperature: +6.2 (c=0.96, $CHCl_3$);

IR (KBr film): 3415, 2934, 2867, 1445, 1361, 1318, 1278, 1239, 1171, 1104, 1055, 1040, 948, 856, 829 cm$^{-1}$;

$^1$H NMR (500 MHz, $CDCl_3$): 3.92-3.90 (4 H, m), 3.55-3.49 (2 H, m), 2.25-2.15 (1 H, m), 1.91 (1 H, dd, J=13.0, 8.5 Hz), 1.83-1.76 (1 H, m), 1.62-1.55 (7 H, m), 1.52-1.47 (1 H, m), 1.37-1.28 (4 H, m), and 1.04 (1 H, dd, J=13.0, 8.8 Hz) ppm;

$^{13}$C NMR/DEPT (75 MHz, $CDCl_3$): 109.5 (C), 68.0 ($CH_2$), 64.1 ($CH_2$), 64.0 ($CH_2$), 44.9 ($CH_2$), 64.3 ($CH_2$), 43.8 (C), 41.7 ($CH_2$), 41.3 (CH), 38.8 ($CH_2$), 38.1 ($CH_2$), 35.0 ($CH_2$), 27.8 ($CH_2$), and 21.1 ($CH_2$) ppm;

MS m/z (%): 226 (M$^+$, 3), 195 (9), 183 (99), 165 (3), 121 (4), 113 (9) (100), 86 (23), 79 (10), 67 (8), 55 (23), 41 (16); and elemental analysis: calculated for $C_{13}H_{22}O_3$: C, 68.99; H, 9.80. Found: C, 68.85; H, 9.84.

d) Preparation of toluene-4-sulfonic acid 1,4-dioxa-dispiro[4.1.4.3]tetradec-9-ylmethyl ester (15)

To a solution of (1,4-dioxa-dispiro[4.1.4.3]tetradec-9-yl) methanol (14a) (1.20 g, 5.3 mmol) in dry pyridine (12 mL) at 0° C. was added 4-dimethylamino-pyridine (catalytic amount) and p-toluenesulfonyl chloride (2.04 g, 10.6 mmol). The reaction mixture was stirred at room temperature for 24 hours and then poured into a 2 M HCl solution (50 mL). The aqueous solution was extracted with $CH_2Cl_2$ and the combined organic layers were washed with a 2 M HCl solution and then with a saturated $K_2CO_3$ solution. After drying over anhydrous $MgSO_4$, the solvent was removed in vacuo to afford the desired product as a colorless oil which was used without further purification in the next step.

e) Preparation of 9-iodomethyl-1,4-dioxa-dispiro [4.1.4.3]tetradec-9-ylmethyl ester (16)

Toluene-4-sulfonic acid 1,4-dioxa-dispiro[4.1.4.3]tetradec-9-ylmethyl ester (15) obtained in the previous step was dissolved in $CH_3CN$ (20 mL). To this solution were added NaI (2.39 g, 15.9 mmol) and $NaHCO_3$ (catalytic amount) and the reaction mixture was then refluxed for 5 hours. The mixture was allowed to cool to room temperature and the solvent was removed in vacuo. The resulting residue was dissolved in $CH_2Cl_2$ (40 mL) and the solution was washed with $H_2O$ and dried over anhydrous $MgSO_4$. The solvent was removed in vacuo and the resulting residue was purified over silica (isooctane/EtOAc, 9:1) to afford 1.48 g (83% yield) of the desired iodide isomer (16) which was characterized as follows:

$R_f$ (isooctane/EtOAc, 95:5) 0.30;

optical rotation at room temperature: +7.7 (c=1.03, $CHCl_3$);

UV (MeOH) absorption at 253 nm;

IR (KBr film): 2934, 2867, 1445, 1425, 1362, 1278, 1182, 1169, 1107, 1077, 1044, 946, 913, 853, 830 and 743 cm$^{-1}$;

$^1$H NMR (500 MHz, $CDCl_3$): 3.94-3.90 (4 H, m), 3.22 (1 H, ABd, J=9.3, 6.5 Hz), 3.16 (1 H, ABd, J=9.3, 7.2 Hz), 2.30-2.21 (1 H, m), 1.91-1.82 (2 H, m), 1.66-1.52 (8 H, m), 1.34-1.25 (3 H, m) and 1.12 (1 H, dd, J=13.1, 10.0 Hz) ppm;

$^{13}$C NMR (125 MHz, $CDCl_3$): 109.3 (C), 64.0 ($CH_2$), 46.4 ($CH_2$), 46.2 ($CH_2$), 44.4 (C), 41.1 (CH), 38.3 ($CH_2$), 36.4 ($CH_2$), 34.9 ($CH_2$), 31.7 ($CH_2$), 20.6 ($CH_2$) and 14.7 ($CH_2$) ppm; and MS m/z (%): 293 (66), 209 (96), 147 (9), 99 (100), 86 (35), 79 (17), 55 (31) and 41 (26).

f) Preparation of 4-(1,4-dioxa-dispiro[4.1.4.3]tetradec-9-yl)-butyric acid ethyl ester (17)

To a suspension of zinc powder (680 mg, 10.4 mmol) in dry pyridine (15 mL) was added ethyl acrylate (1.13 mL, 10.4 mmole) followed by $NiCl_2.6H_2O$ (593 mg, 2.5 mmol) and the reaction mixture was stirred at 65° C. for 2 hours. The mixture was allowed to cool to room temperature and 9-iodomethyl-1,4-dioxa-dispiro[4.1.4.3]tetradec-9-yl methyl ester (16) (700 mg, 2.08 mmol) dissolved dry pyridine (8 mL) was added dropwise and the reaction mixture stirred at room temperature for 3 hours. The mixture was poured into EtOAc (30 mL) and the resulting precipitate removed by filtration through a bed of Celite. The filtrate was collected and washed two times with a 1 M HCl solution, then saturated $NaHCO_3$, and dried over anhydrous $MgSO_4$. The solvent was removed in vacuo and the resulting residue was purified over silica (isooctane/EtOAc, 9:1) to afford 530 mg (82% yield) of the desired isomer (17) as a colorless oil which was characterized as follows:

$R_f$ (isooctane/EtOAc, 9:1) 0.23;

optical rotation at room temperature: +11.0 (c=1.00, $CHCl_3$);

IR (KBr film): 2933, 2867, 1736, 1446, 1368, 1243, 1175, 1110, 1072, 1046, 943, 857, 828 and 685 cm$^{-1}$;

$^1$H NMR (500 MHz, $CDCl_3$): 4.11 (2 H, q, J=7.1 Hz), 3.91 (4 H, s), 2.27 (1 H, t, J=7.6 Hz), 1.92-1.83 (1 H, m), 1.81-1.73 (2 H, m), 1.64-1.53 (9 H, m), 1.47-1.41 (1 H, m), 1.33-1.28 (4 H, m), 1.25 (3 H, t, J=7.1 Hz), 1.19-1.12 (1 H, m) and 0.96 (1 H, dd, J=12.8, 10.2 Hz) ppm;

$^{13}$C NMR (75 MHz, $CDCl_3$): 173.9 (C), 109.6 (C), 64.0 ($CH_2$), 60.1 ($CH_2$), 46.1 ($CH_2$), 46.2 ($CH_2$), 43.6 (C), 38.3 ($CH_2$), 38.2 (CH), 38.3 ($CH_2$), 36.7 ($CH_2$), 36.2 ($CH_2$), 35.1 ($CH_2$), 31.0 ($CH_2$), 24.1 ($CH_2$), 20.8 ($CH_2$) and 14.3 ($CH_2$) ppm;

MS m/z (%): 310 (M$^+$, 2), 267 (62), 248 (3), 195 (9), 167 (3), 151 (4), 113 (9), 99 (100), 86 (26), 55 (26) and 41 (16); and elemental analysis: calculated for $C_{18}H_{30}O_4$: C, 69.64; H, 9.74; found: C, 69.80; H, 9.87.

g) Preparation of 5-(1,4-dioxa-dispiro[4.1.4.3]tetradec-9-yl)-2-methyl-pentan-2-ol (18)

To a solution of 4-(1,4-dioxa-dispiro[4.1.4.3]tetradec-9-yl)-butyric acid ethyl ester (17) (530 mg, 1.71 mmol) in dry THF (25 mL) at 0° C. was added dropwise methyl-magnesium bromide (3 M solution in $Et_2O$; 2.83 mL, 8.5 mmol) and the reaction mixture was stirred at room temperature for 3 hours. The reaction was quenched by adding a saturated $NH_4Cl$ solution (30 mL), the aqueous layer was then separated and repeatedly extracted with $Et_2O$. The combined organic layers were dried over anhydrous $MgSO_4$ and the solvents removed in vacuo. The resulting residue was purified over silica (isooctane/EtOAc, 8:2) to afford 451 mg (89% yield) of the desired alcohol isomer (18) which was characterized as follows:

$R_f$ (cyclohexane/EtOAc, 8:2) 0.26;

optical rotation at room temperature: +11.2 (c=1.06, $CHCl_3$);

IR (KBr film): 3440, 2932, 2866, 2843, 1446, 1362, 1336, 1278, 1173, 1111, 1082, 1067, 1047, 1005, 945, 909, 856 and 826 cm$^{-1}$;

$^1$H NMR (500 MHz, CDCl$_3$): 3.91 (4 H, s), 1.93-1.84 (1 H, m), 1.81-1.72 (2 H, m), 1.59-1.54 (8 H, m), 1.47-1.41 (3 H, m), 1.36-1.26 (6 H, m), 1.20 (6 H, s), 1.18-1.14 (1 H, m) and 0.99 (1 H, dd, J=12.7, 10.3 Hz) ppm;

$^{13}$C NMR (75 MHz, CDCl$_3$): 109.6 (C), 71.1 (C), 64.1 (CH$_2$), 46.5 (CH$_2$), 46.4 (CH$_2$), 44.3 (CH$_2$), 43.6 (C), 38.5 (CH), 38.3 (CH$_2$), 37.3 (CH$_2$), 36.9 (CH$_2$), 35.1 (CH$_2$), 31.2 (CH$_2$), 29.3 (CH$_3$), 23.5 (CH$_2$) and 20.8 (CH$_2$) ppm; and MS m/z (%): 296 (M$^+$, 2), 281 (2), 253 (44), 195 (4), 113 (10), 107 (16), 99 (100), 86 (21), 55 (27) and 41 (21).

h) Preparation of 2-(4-hydroxy-4-methylpentyl)-spiro[4.5]decan-7-one (19)

To a solution of 5-(1,4-dioxa-dispiro[4.1.4.3]tetradec-9-yl)-2-methyl-pentan-2-ol (18) (420 mg, 1.42 mmol) in acetone (9 mL) was added H$_2$O (catalytic amount) and p-toluenesulfonic acid (catalytic amount). The reaction mixture was stirred at room temperature overnight and then dried over anhydrous MgSO$_4$. The solution was filtered through silica and the filtrate concentrated under reduced pressure. The resulting residue was purified over silica (isooctane/EtOAc, 7:3) to afford 312 mg (86% yield) of the desired ketone isomer as a colorless oil which was characterized as follows:

R$_f$ (isooctane/EtOAc, 4:6) 0.46;

optical rotation at room temperature: +13.7 (c=0.81, CHCl$_3$) for isomer (19a); and −14.4 (c=0.99, CHCl$_3$) for isomer;

IR (KBr film): 3434, 2935, 2861, 1704, 1462, 1444, 1422, 1376, 1312, 1286, 1227, 1155, 1077, 938 and 909 cm$^{-1}$;

$^1$H NMR (500 MHz, CDCl$_3$): 2.30-2.22 (4 H, m), 1.94-1.77 (4 H, m), 1.74 (1 H, dd, J=12.9, 7.7 Hz), 1.64 (2 H, t, J=6.0 Hz), 1.48 (1 H, ddd, J=12.7, 8.5, 4.0 Hz), 1.46-1.39 (3 H, m), 1.36-1.30 (4 H, m), 1.25-1.21 (2 H, m), 1.20 (6 H, s) and 0.97 (1 H, dd, J=12.9, 9.8 Hz) ppm;

$^{13}$C NMR (75 MHz, CDCl$_3$): 212.1 (C), 71.0 (C), 54.8 (CH$_2$), 47.2 (C), 45.4 (CH$_2$), 44.1 (CH$_2$), 41.2 (CH$_2$), 39.3 (CH), 37.9 (CH$_2$), 37.0 (CH$_2$), 31.6 (CH$_2$), 29.3 (CH$_3$), 23.5 (CH$_2$) and 23.4 (CH$_2$) ppm; and MS m/z (%): 237 (9), 234 (3), 201 (4), 194 (21), 165 (17), 161 (14), 151 (23), 123 (46), 110 (69), 93 (26), 67 (24), 59 (100), 55 (34), 43 (34) and 41(38).

As mentioned herein above, the corresponding 2-(4-hydroxy-4-methylpentyl)-spiro[4.5]decan-7-thione is also accessible in step (h) when starting from 7-(4-oxo-butyl)-1,4-dithiaspiro[4.5]decane-7-carbaldehyde.

Scheme III is an exemplary scheme of a procedure which can be used for coupling a R$^{1b}$ containing spiro[4.5]-decan-7-yl unit with a Q unit, both being as defined herein above. The synthesis of the Q-unit was performed as known in the art. In the last step of this scheme, an intermediate such as 22a is used as a precursor for producing compounds comprised in category I of the present invention whereas an intermediate such as 22b is an exemplary precursor useful for producing compounds encompassed within category II of the present invention. The following scheme includes a sequence of three steps for making the vitamin D analogue compounds of this invention. Each step will now be illustrated in details, based on specific starting compounds, reactive agents, catalysts, solvents, temperature ranges and the like, but the skilled person will understand that the specific materials, conditions and number of process steps disclosed herein may be replaced with similar or equivalent materials and conditions without significantly altering the resulting product of the relevant step or the final resulting product, except may be for the yield thereof. In particular, scheme III illustrates a procedure starting from 2-(4-hydroxy-4-methylpentyl)-spiro[4.5]decan-7-one obtained in the last step of scheme II, but the skilled person understands that a similar sequence of steps can be performed successfully while starting from the corresponding 2-(4-hydroxy-4-methylpentyl)-spiro[4.5]decan-7-thione.

Scheme III

In a first step (a), the hydroxyl group is protected by means of a suitable O-protecting group. Conventional O-protecting groups for protecting hydroxyls are well known in the art and include silyl, acyl, lower alkyl or alkenyl mono-carbonyl, alkoxycarbonyl, alkylcarbonyl, lower alkoxycarbonylalkylcarbonyl, and arylcarbonyl groups. Exemplary O-protecting groups include, but are not limited to, alkoxycarbonyls (e.g. methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl and the like), alkoxyalkoxycarbonyls (e.g. methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl and the like), haloalkoxycarbonyls (e.g. 2-chloroethoxycarbonyl, 2-chloroethoxycarbonyl, 2,2,2-trichloroethoxycarbonyl and the like), unsaturated alkoxycarbonyls (e.g., allyloxycarbonyl, propargyloxycarbonyl, 2-butenoxycarbonyl, 3-methyl-2-butenoxycarbonyl and the like), substituted benzyloxycarbonyls (e.g. benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl and the like) and substituted phenoxycarbonyls (e.g. phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl and the like. A broader review of such groups may be found e.g. in Greene et al., Protective Groups in Organic Synthesis, 2$^{nd}$ ed., John Wiley & Sons, Inc., New York, (1991).

Exemplary lower alkyl monocarbonyl groups which may be present in such O-protecting groups include, but are not limited to, acetyl, propionyl, butyryl, isobutyryl and the like. Exemplary lower alkenyl monocarbonyl groups which may be present in such are O-protecting groups include, but are not limited to, acryloxy, methacryloxy and the like. Exemplary lower alkoxycarbonyl-alkylcarbonyl groups include, but are not limited to, methoxycarbonyl-methylcarbonyl, ethoxycarbonyl-methylcarbonyl, ethoxycarbonyl-ethylcarbonyl and the like. Exemplary arylcarbonyl groups include, but are not limited to, benzoyl, p-methoxybenzoyl, 3,4,5-trimethoxy benzoyl, p-chlorobenzoyl, 2,4-dichlorobenzoyl, 3,5-dichlorobenzoyl, diphenylacetyl, 1-naphthaleneacetyl, 2-naphthaleneacetyl and the like. Exemplary silyl groups may be represented by the formula —SiR'R"R"', wherein each of R', R" and R"' is independently selected from the group consisting of C$_{1-7}$ alkyl, C$_{2-7}$ alkenyl, C$_{3-10}$ cycloalkyl and aryl.

Conventional O-protecting groups, as set forth above, may be positioned during this first step by using standard procedures well known in the art.

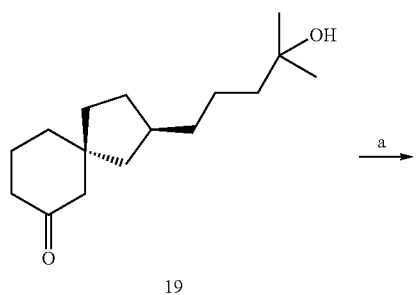

19

(preferred reagents and conditions for step (a): trimethylsilylimidazole (TMSimidazole) ether as a protecting group-containing reagent, THF as a solvent; temperature ranging from about 10' C. to about 40° C.).

In a second step (b), the 2-(4-methyl-4-trimethylsilanyloxy-pentyl)-spiro[4.5]decan-7-one from step (a) is submitted to a Horner-Wittig reaction involving a phosphine oxide corresponding to the A-ring scaffold of the desired vitamin $D_3$ analog and wherein hydroxy groups are protected with conventional O-protecting groups (such as described hereinabove), optionally in the presence of an effective amount of a suitable catalyst (preferably an organometallic species-derived from an alkaline metal such as, but not limited to, an alkyllithium) and optionally in the presence of a suitable solvent such as an ether:

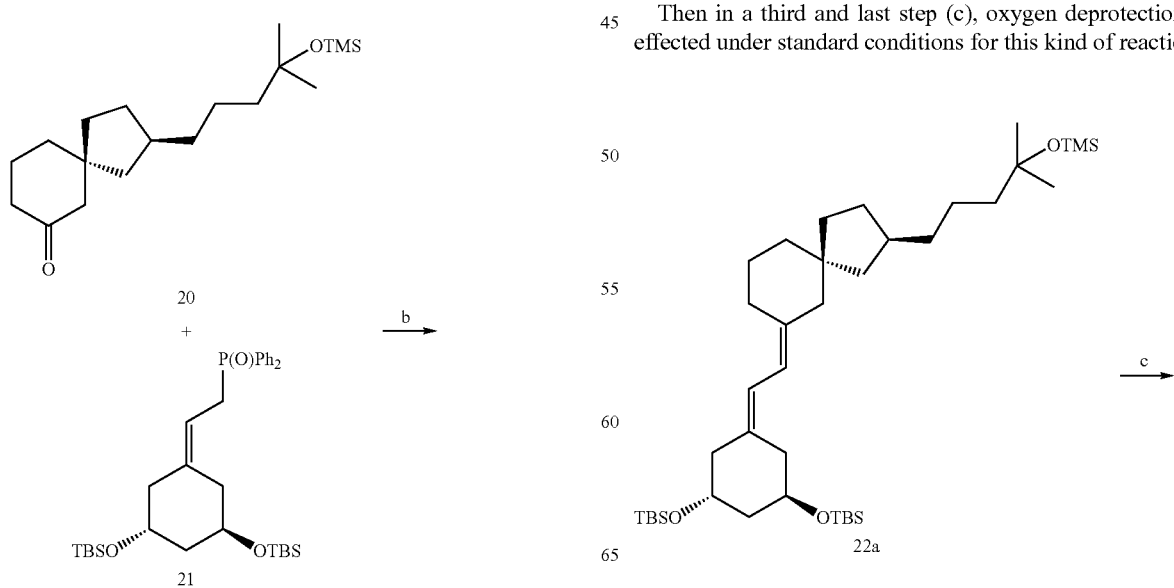

-continued

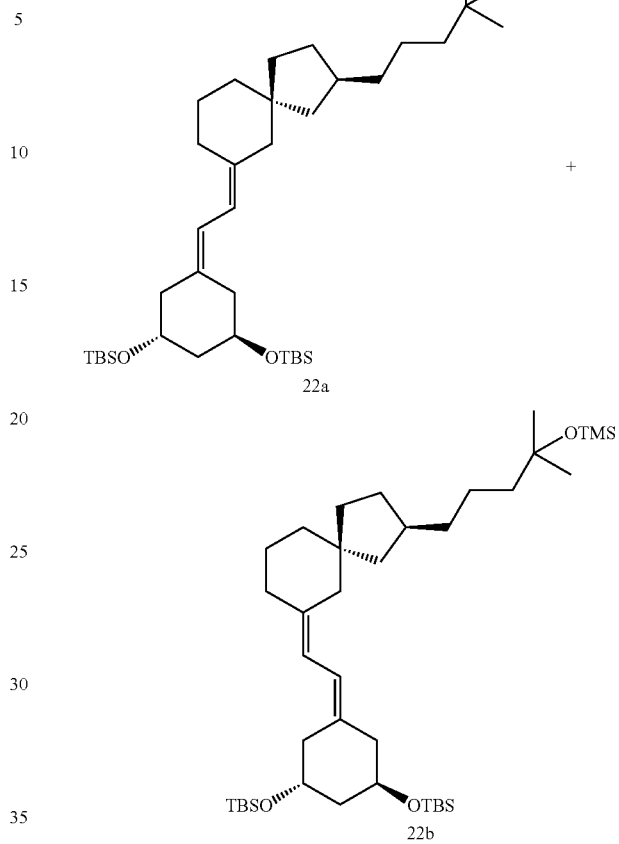

(preferred reagents and conditions for step (b) are: 5-[2-(diphenyl-phosphinoyl)-ethylidene]-bis-(tert-butyl-dimethyl-silanyloxy)-cyclohexane as a phosphine oxide reagent, n-BuLi as a catalyst, THF as a solvent; temperature ranging from about −90° C. to about −60° C.).

Then in a third and last step (c), oxygen deprotection is effected under standard conditions for this kind of reaction:

-continued

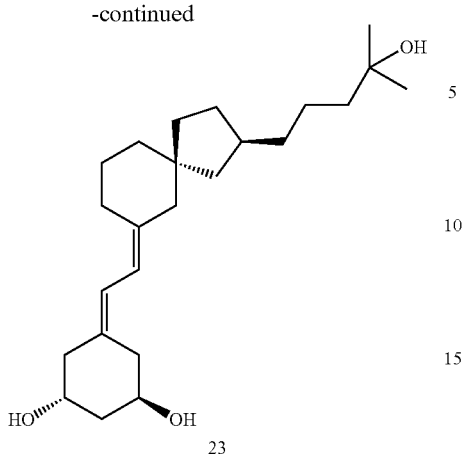

23

(preferred reagents and conditions include: (c) tetrabutylammonium fluoride as a reagent; THF as a solvent; temperature ranging from about 10° C. to about 40° C.).

For the ease of understanding and the completion of the disclosure of other stereoisomers which are also available by this methodology, scheme III' hereunder provides a full depiction of a similar synthetic route starting from the other stereoisomer (19'). The skilled person understands that a similar sequence of reactions can be performed successfully while starting from the corresponding 2-(4-hydroxy-4-methylpentyl)-spiro[4.5]decan-7-thione.

Scheme III'

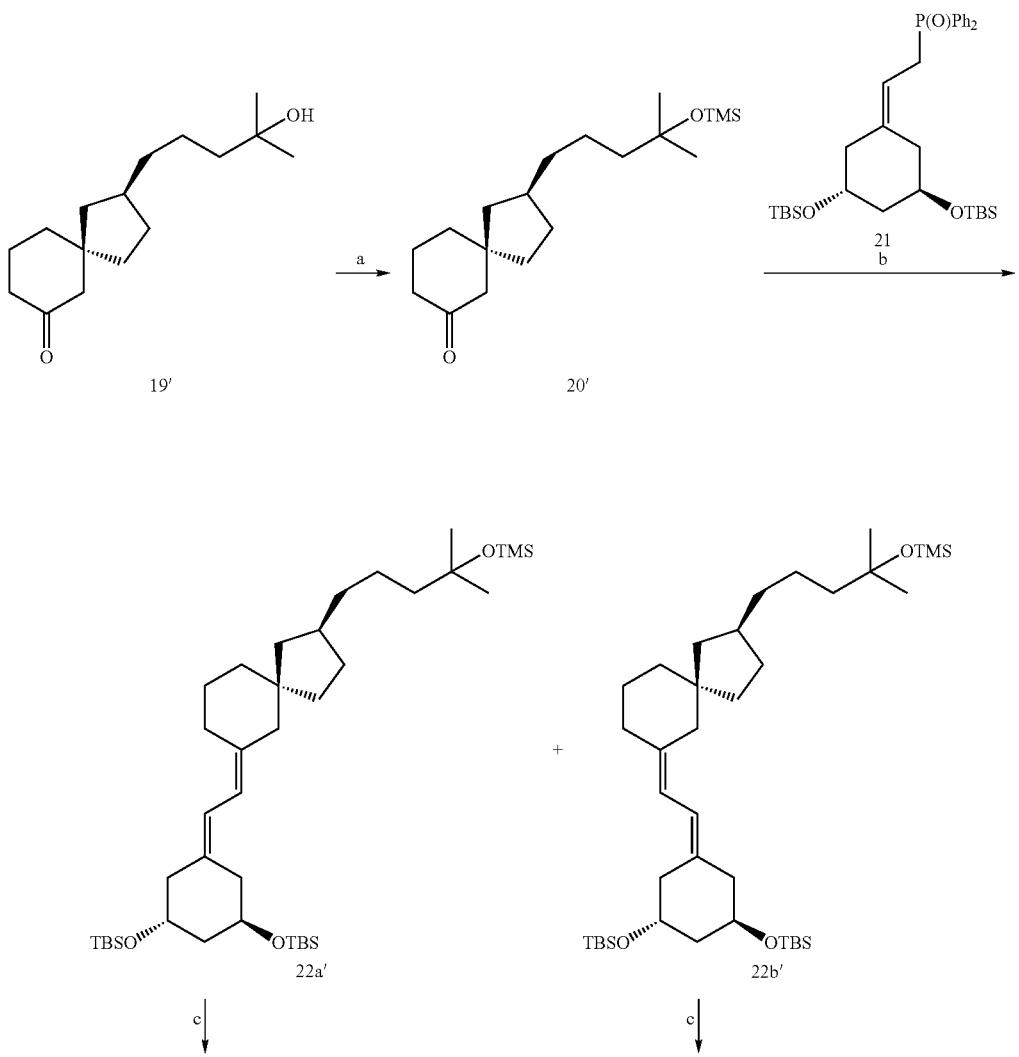

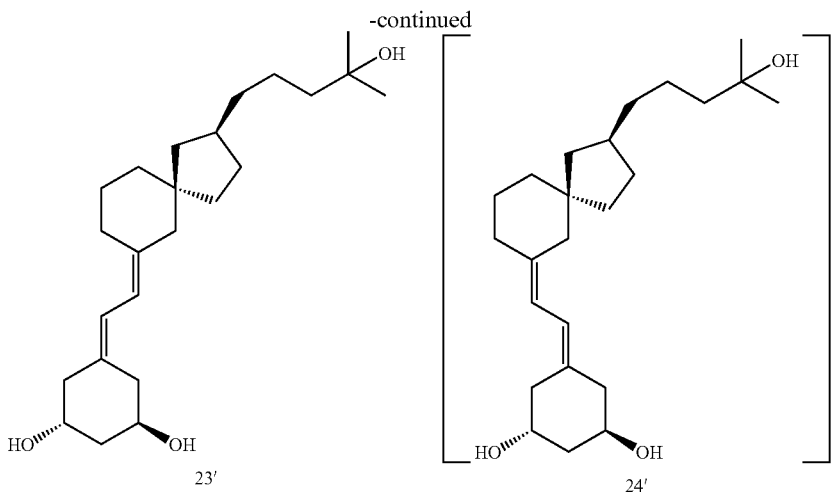

EXAMPLE 3

Preparation of (1R,3R)-5-{2-[(2R,5S)-2-(4-hydroxy-4-methyl-pentyl)spiro[4.5]dec-(7E)-ylidenel]-ethylidene}-cyclo-hexane-1,3-diol (23)

a) preparation of 2-(4-methyl-4-trimethylsilanyloxy-pentyl)-spiro[4.5]decan-7-one (20)

To a solution of a 2-(4-hydroxy-4-methylpentyl)-spiro [4.5]decan-7-one (19a) (50 mg, 0.198 mmol) in dry THF (1 mL) was added 1-(trimethylsilyl)-imidazole (0.146 mL, 0.99 mmol). The reaction mixture was stirred at room temperature for 4 hours and the solvent was then removed in vacuo. The resulting residue was purified over silica (petroleum ether/ EtOAc, 95:5) to afford the desired product which was used directly for the next reaction step.

b) Preparation of 7-{2-[3,5-bis-(tert-butyl-dimethyl-silanyloxy)-cyclohexylidene]-ethylidene}-2-(4-methyl-4-trimethylsilanyloxy-penty)-spiro[4.5]decane (22)

To a solution of 5-[2-(diphenyl-phosphinoyl)-ethylidene]-bis-(tert-butyl-dimethyl-silanyloxy)-cyclohexane (21) (which may be obtained according to the procedure disclosed by Perlman et al. in *Tetrahedron Lett.* (1991) 32, 7663-7666), (225 mg, 0.40 mmol) in dry THF (4 mL) at −78 ° C. was added dropwise n-BuLi (2.5 M solution in n-hexane; 0.167 mL, 0.417 mmol) and the reaction mixture was stirred at −78° C. for 1 hour. A solution of 2-(4-methyl-4-trimethylsilanyloxy-pentyl)-spiro[4.5]decan-7-one (20) obtained in the above step (a), in dry THF (3.5 mL) was added dropwise and the reaction mixture was stirred at −78° C. for 4 hours. The temperature was allowed to rise to room temperature and the solvent removed in vacuo. The resulting residue was purified over silica (petroleum ether/EtOAc, 95:5) to afford the desired product as a mixture of isomers which was used without further purification.

c) Preparation of (1R,3R)-5-{2-[(2S,5R)-2-(4-hydroxy-4-methyl-pentyl)-spiro[4.5]dec-(7E)-ylidene]-ethylidene}-cyclohexane-1,3-diol (23)

To the intermediate (22) obtained in step (b) was added n-Bu$_4$NF (1 M solution in THF; 1.98 mL, 1.98 mmol), and the reaction mixture was stirred at room temperature for about 16 hours. Deprotection according to this procedure, followed by purified over silica (CH$_2$Cl$_2$/Me$_2$CO, 7:3) afforded with a 95% yield a 3:1 mixture of the 7E-isomer and the 7Z-isomer of the desired vitamin D$_3$ analog. The 7E-isomer was then separated from the 7Z-isomer by HPLC and characterized as follows:

R$_f$(CH$_2$Cl$_2$/Me$_2$CO, 6:4) 0.37;

UV (MeOH): absorption at 259, 249 and 242 nm;

IR (KBr film): 3364, 2930, 2857,1617, 1444, 1364, 1212, 1151, 1049, 976, 938, 908, 864, 812 and 733 cm$^{-1}$;

$^1$H NMR (500 MHz, CDCl$_3$): 6.23 (1 H, A̲B, J=11.3 Hz), 5.93 (1 H, AB̲, J=11.3 Hz), 4.11-4.02 (2 H, m), 2.68 (1 H, dd, J=13.2, 3.8 Hz), 2.47 (1 H, dd, J=13.3, 3.6 Hz), 2.28-2.16 (4 H, m), 2.00 (2 H, s), 1.93-1.71 (5 H, m), 1.57 (1 H, dd, J=12.9, 7.9 Hz), 1.53-1.43 (8 H, m), 1.36-1.26 (6 H, m), 1.21 (6 H, s), 1.21-1.13 (1 H, m), and 0.94 (1 H, dd, J=12.9, 9.4 Hz) ppm;

$^{13}$C NMR (75 MHz, CDCl$_3$): 142.0 (C), 131.4 (C), 123.8 (CH), 117.9 (CH), 71.2 (C), 67.5 (CH), 67.1 (CH), 50.7 (CH$_2$), 45.1 (C), 44.8 (CH$_2$), 44.7 (CH$_2$), 44.2 (CH$_2$), 42.2 (CH$_2$), 39.4 (CH), 39.0 (CH$_2$), 38.2 (CH$_2$), 37.2 (CH$_2$), 31.8 (CH$_2$), 29.3 (CH$_3$), 29.2 (CH$_3$), 28.7 (CH$_2$), 24.4 (CH$_2$) and 23.4 (CH$_2$) ppm; and MS m/z (%): 376 (M$^+$, 2), 358 (24), 340 (26), 325 (5), 261 (5), 243 (5), 217 (8), 177 (26), 163 (14), 145 (24), 133 (19), 119 (28), 105 (32), 93 (66), 91 (61), 79 (60), 67 (56), 59 (100), 55 (61), 43 (86) and 41 (71).

Compounds which are comprised in category II of the present invention include, but are not limited to, the Z-isomers of 5-[2-(2-R$^{1a}$-substituted-spiro[4.5]dec-7-ylidene)-ethylidene]-cyclohexane-1,3-diols having the following general formula:

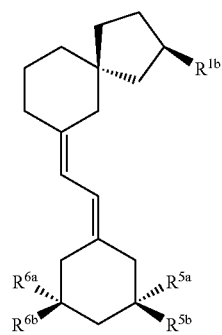

wherein the $R^{1b}$ substitutions at carbon 20 are outlined herein below in Table 3.

TABLE 3

| No. | $R^{1b}$ | $R^{5a}$ | $R^{5b}$ | $R^{6a}$ | $R^{6b}$ |
|---|---|---|---|---|---|
| 61 | 4-hydroxy-4-methylpentyl | H | OH | OH | H |
| 62 | 5-hydroxy-5-methylhex-2-yl | H | OH | OH | H |
| 63 | 6-hydroxy-6-methylhept-2-yl | H | OH | OH | H |
| 64 | 5-hydroxy-6-methylhept-2-yl | H | OH | OH | H |
| 65 | 1-hydroxy-5,5-dimethylhexyl | H | OH | OH | H |
| 66 | 7-hydroxy-7-methyloct-4-en-2-yl | H | OH | OH | H |
| 67 | 7-hydroxy-7-ethylnon-4-en-2-yl | H | OH | OH | H |
| 68 | 7-hydroxy-7-ethylnon-4-en-2-yl | H | OH | OH | H |
| 69 | 7-hydroxy-7-ethylnon-3,5-dien-2-yl | H | OH | OH | H |
| 70 | 5-hydroxy-5-methylhex-3-ynyl | H | OH | OH | H |
| 71 | 4-(2-methyl-oxyranyl)-but-3-ynyl | H | OH | OH | H |
| 72 | 6-hydroxy-6-methylhept-3-yn-2-yl | H | OH | OH | H |
| 73 | 5-(2-methyloxyranyl)-pent-4-yn-2-yl | H | OH | OH | H |
| 74 | 5-hydroxy-5-ethylhept-3-ynyl | H | OH | OH | H |
| 75 | 6-hydroxy-6-ethyloctyn-4-yn-2-yl | H | OH | OH | H |
| 76 | 4-hydroxy-4-methylpentyl | OH | H | OH | H |
| 77 | 5-hydroxy-5-methylhex-2-yl | OH | H | OH | H |
| 78 | 6-hydroxy-6-methylhept-2-yl | OH | H | OH | H |
| 79 | 5-hydroxy-6-methylhept-2-yl | OH | H | OH | H |
| 80 | 1-hydroxy-5,5-dimethylhexyl | OH | H | OH | H |
| 81 | 7-hydroxy-7-methyloct-4-en-2-yl | OH | H | OH | H |
| 82 | 7-hydroxy-7-ethylnon-4-en-2-yl | OH | H | OH | H |
| 83 | 7-hydroxy-7-ethylnon-4-en-2-yl | OH | H | OH | H |
| 84 | 7-hydroxy-7-ethylnon-3,5-dien-2-yl | OH | H | OH | H |
| 85 | 5-hydroxy-5-methylhex-3-ynyl | OH | H | OH | H |
| 86 | 4-(2-methyl-oxyranyl)-but-3-ynyl | OH | H | OH | H |
| 87 | 6-hydroxy-6-methylhept-3-yn-2-yl | OH | H | OH | H |
| 88 | 5-(2-methyloxyranyl)-pent-4-yn-2-yl | OH | H | OH | H |
| 89 | 5-hydroxy-5-ethylhept-3-ynyl | OH | H | OH | H |
| 90 | 6-hydroxy-6-ethyloctyn-4-yn-2-yl | OH | H | OH | H |
| 91 | 4-hydroxy-4-methylpentyl | H | OH | OH | H |
| 92 | 5-hydroxy-5-methylhex-2-yl | H | OH | OH | H |
| 93 | 6-hydroxy-6-methylhept-2-yl | H | OH | OH | H |
| 94 | 5-hydroxy-6-methylhept-2-yl | H | OH | OH | H |
| 95 | 1-hydroxy-5,5-dimethylhexyl | H | OH | OH | H |
| 96 | 7-hydroxy-7-methyloct-4-en-2-yl | H | OH | OH | H |
| 97 | 7-hydroxy-7-ethylnon-4-en-2-yl | H | OH | OH | H |
| 98 | 7-hydroxy-7-ethylnon-4-en-2-yl | H | OH | OH | H |
| 99 | 7-hydroxy-7-ethylnon-3,5-dien-2-yl | H | OH | OH | H |
| 100 | 5-hydroxy-5-methylhex-3-ynyl | H | OH | OH | H |
| 101 | 4-(2-methyl-oxyranyl)-but-3-ynyl | H | OH | OH | H |
| 102 | 6-hydroxy-6-methylhept-3-yn-2-yl | H | OH | OH | H |
| 103 | 5-(2-methyloxyranyl)-pent-4-yn-2-yl | H | OH | OH | H |
| 104 | 5-hydroxy-5-ethylhept-3-ynyl | H | OH | OH | H |
| 105 | 6-hydroxy-6-ethyloctyn-4-yn-2-yl | H | OH | OH | H |
| 106 | 4-hydroxy-4-methylpentyl | OH | H | H | OH |
| 107 | 5-hydroxy-5-methylhex-2-yl | OH | H | H | OH |
| 108 | 6-hydroxy-6-methylhept-2-yl | OH | H | H | OH |
| 109 | 5-hydroxy-6-methylhept-2-yl | OH | H | H | OH |
| 110 | 1-hydroxy-5,5-dimethylhexyl | OH | H | H | OH |
| 111 | 7-hydroxy-7-methyloct-4-en-2-yl | OH | H | H | OH |
| 112 | 7-hydroxy-7-ethylnon-4-en-2-yl | OH | H | H | OH |
| 113 | 7-hydroxy-7-ethylnon-4-en-2-yl | OH | H | H | OH |
| 114 | 7-hydroxy-7-ethylnon-3,5-dien-2-yl | OH | H | H | OH |

TABLE 3-continued

| No. | $R^{1b}$ | $R^{5a}$ | $R^{5b}$ | $R^{6a}$ | $R^{6b}$ |
|---|---|---|---|---|---|
| 115 | 5-hydroxy-5-methylhex-3-ynyl | OH | H | H | OH |
| 116 | 4-(2-methyl-oxyranyl)-but-3-ynyl | OH | H | H | OH |
| 117 | 6-hydroxy-6-methylhept-3-yn-2-yl | OH | H | H | OH |
| 118 | 5-(2-methyloxyranyl)-pent-4-yn-2-yl | OH | H | H | OH |
| 119 | 5-hydroxy-5-ethylhept-3-ynyl | OH | H | H | OH |
| 120 | 6-hydroxy-6-ethyloctyn-4-yn-2-yl | OH | H | H | OH |

Compounds which are comprised in category II of the present invention also be conveniently prepared as a mixture of isomers with the sponding E-isomer (compound of category I) and then isolated by preparative HPLC. The following non-limiting exemplary compound can be prepared according to Scheme III herein above and isolated as part of the purification of compound 23.

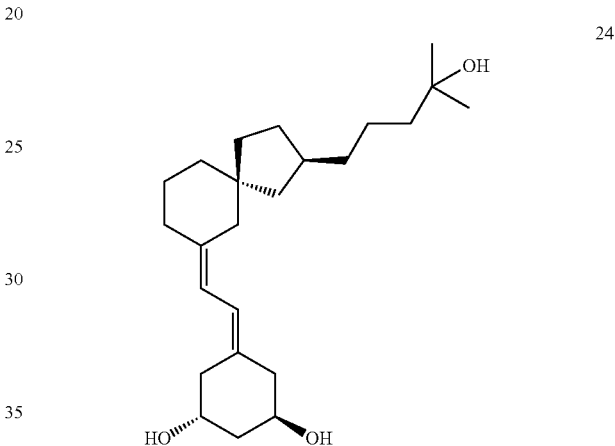

Characterization of (1R,3R)-5-{2-[(2S, 5R)-2-(4-hydroxy-4-methylpentyl)-spiro[4.5]dec-(7Z)-ylidene]-ethylidene}-cyclo-hexane-1,3-diol (24) is as follows:

$R_f$ ($CH_2Cl_2/Me_2CO$, 6:4) 0.37;

UV (MeOH) absorption bands at 259, 249 and 242 nm;

IR (KBr film): 3372, 2930, 2861, 1615, 1444, 1377, 1215, 1151, 1049, 973, 908 and 730 $cm^{-1}$;

$^1$H NMR (500 MHz, CDCl$_3$): 6.23 (1 H, <u>A</u>B, J=11.2 Hz), 6.05 (1 H, A<u>B</u>, J=11.2 Hz), 4.08 (2 H, br s), 2.58 (1 H, dd, J=13.4, 3.5 Hz), 2.50 (1 H, dd, J=12.9, 3.7 Hz), 2.35 (1 H, dd, J=13.4, 7.1 Hz), 2.20-2.17 (5 H, m), 1.90-1.82 (3 H, m), 1.80-1.74 (1 H, m), 1.61 (1 H, dd, J=12.9, 7.9 Hz), 1.57-1.43 (9 H, m), 1.35-1.27 (6 H, m), 1.22-1.17.(1 H, m), 1.21 (6 H, s) and 0.92 (1 H, dd, J=12.9, 9.5 Hz) ppm;

$^{13}$C NMR (75 MHz, CDCl$_3$): 142.2 (C), 131.4 (C), 123.9 (CH), 118.0 (CH), 71.1 (C), 67.5 (CH), 67.4 (CH), 45.2 (C+CH$_2$), 44.2 (CH$_2$), 42.2 (CH$_2$), 42.0 (CH$_2$), 39.3 (CH), 39.1 (CH$_2$), 38.2 (CH$_2$), 37.4 (CH$_2$), 37.3 (CH$_2$), 36.8 (CH$_2$), 31.9 (CH$_2$), 29.4 (CH$_3$), 29.2 (CH$_3$), 25.4 (CH$_2$) and 23.5 (CH$_2$) ppm; and MS m/z (%): 358 (M$^+$—H$_2$O, 48), 340 (31), 325 (9), 177 (35), 145 (33), 119 (32), 105 (40), 93 (69), 91 (88), 79 (69), 67 (55), 59 (100), 55 (44), 43 (68) and 41 (55).

Compounds which are comprised in category III of the present invention include, but are. not limited to, the E-isomers of 5-[2-(2-R$^{1a}$-substituted-spiro[4.5]dec-7-ylidene)-ethylidene]-cyclohexane-1,3-diols having the following structural formula:

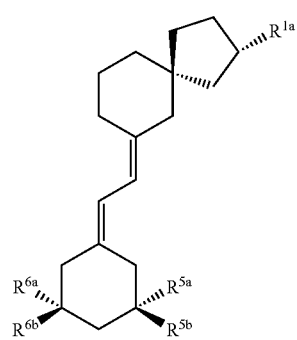

wherein the $R^{1a}$ substitutions at carbon-20 are outlined herein below in Table 4.

TABLE 4

| No. | $R^{1a}$ | $R^{5a}$ | $R^{5b}$ | $R^{6a}$ | $R^{6b}$ |
|---|---|---|---|---|---|
| 121 | 4-hydroxy-4-methylpentyl | H | OH | OH | H |
| 122 | 5-hydroxy-5-methylhex-2-yl | H | OH | OH | H |
| 123 | 6-hydroxy-6-methylhept-2-yl | H | OH | OH | H |
| 124 | 5-hydroxy-6-methylhept-2-yl | H | OH | OH | H |
| 125 | 1-hydroxy-5,5-dimethylhexyl | H | OH | OH | H |
| 126 | 7-hydroxy-7-methyloct-4-en-2-yl | H | OH | OH | H |
| 127 | 7-hydroxy-7-ethylnon-4-en-2-yl | H | OH | OH | H |
| 128 | 7-hydroxy-7-ethylnon-4-en-2-yl | H | OH | OH | H |
| 129 | 7-hydroxy-7-ethylnon-3,5-dien-2-yl | H | OH | OH | H |
| 130 | 5-hydroxy-5-methylhex-3-ynyl | H | OH | OH | H |
| 131 | 4-(2-methyl-oxyranyl)-but-3-ynyl | H | OH | OH | H |
| 132 | 6-hydroxy-6-methylhept-3-yn-2-yl | H | OH | OH | H |
| 133 | 5-(2-methyloxyranyl)-pent-4-yn-2-yl | H | OH | OH | H |
| 134 | 5-hydroxy-5-ethylhept-3-ynyl | H | OH | OH | H |
| 135 | 6-hydroxy-6-ethyloctyn-4-yn-2-yl | H | OH | OH | H |
| 136 | 4-hydroxy-4-methylpentyl | OH | H | OH | H |
| 137 | 5-hydroxy-5-methylhex-2-yl | OH | H | OH | H |
| 138 | 6-hydroxy-6-methylhept-2-yl | OH | H | OH | H |
| 139 | 5-hydroxy-6-methylhept-2-yl | OH | H | OH | H |
| 140 | 1-hydroxy-5,5-dimethylhexyl | OH | H | OH | H |
| 141 | 7-hydroxy-7-methyloct-4-en-2-yl | OH | H | OH | H |
| 142 | 7-hydroxy-7-ethylnon-4-en-2-yl | OH | H | OH | H |
| 143 | 7-hydroxy-7-ethylnon-4-en-2-yl | OH | H | OH | H |
| 144 | 7-hydroxy-7-ethylnon-3,5-dien-2-yl | OH | H | OH | H |
| 145 | 5-hydroxy-5-methylhex-3-ynyl | OH | H | OH | H |
| 146 | 4-(2-methyl-oxyranyl)-but-3-ynyl | OH | H | OH | H |
| 147 | 6-hydroxy-6-methylhept-3-yn-2-yl | OH | H | OH | H |
| 148 | 5-(2-methyloxyranyl)-pent-4-yn-2-yl | OH | H | OH | H |
| 149 | 5-hydroxy-5-ethylhept-3-ynyl | OH | H | OH | H |
| 150 | 6-hydroxy-6-ethyloctyn-4-yn-2-yl | OH | H | OH | H |
| 151 | 4-hydroxy-4-methylpentyl | H | OH | OH | H |
| 152 | 5-hydroxy-5-methylhex-2-yl | H | OH | OH | H |
| 153 | 6-hydroxy-6-methylhept-2-yl | H | OH | OH | H |
| 154 | 5-hydroxy-6-methylhept-2-yl | H | OH | OH | H |
| 155 | 1-hydroxy-5,5-dimethylhexyl | H | OH | OH | H |
| 56 | 7-hydroxy-7-methyloct-4-en-2-yl | H | OH | OH | H |
| 157 | 7-hydroxy-7-ethylnon-4-en-2-yl | H | OH | OH | H |
| 158 | 7-hydroxy-7-ethylnon-4-en-2-yl | H | OH | OH | H |
| 159 | 7-hydroxy-7-ethylnon-3,5-dien-2-yl | H | OH | OH | H |
| 160 | 5-hydroxy-5-methylhex-3-ynyl | H | OH | OH | H |
| 161 | 4-(2-methyl-oxyranyl)-but-3-ynyl | H | OH | OH | H |
| 162 | 6-hydroxy-6-methylhept-3-yn-2-yl | H | OH | OH | H |
| 163 | 5-(2-methyloxyranyl)-pent-4-yn-2-yl | H | OH | OH | H |
| 164 | 5-hydroxy-5-ethylhept-3-ynyl | H | OH | OH | H |
| 165 | 6-hydroxy-6-ethyloctyn-4-yn-2-yl | H | OH | OH | H |
| 166 | 4-hydroxy-4-methylpentyl | OH | H | H | OH |
| 167 | 5-hydroxy-5-methylhex-2-yl | OH | H | H | OH |
| 168 | 6-hydroxy-6-methylhept-2-yl | OH | H | H | OH |
| 169 | 5-hydroxy-6-methylhept-2-yl | OH | H | H | OH |
| 170 | 1-hydroxy-5,5-dimethylhexyl | OH | H | H | OH |
| 171 | 7-hydroxy-7-methyloct-4-en-2-yl | OH | H | H | OH |
| 172 | 7-hydroxy-7-ethylnon-4-en-2-yl | OH | H | H | OH |
| 173 | 7-hydroxy-7-ethylnon-4-en-2-yl | OH | H | H | OH |
| 174 | 7-hydroxy-7-ethylnon-3,5-dien-2-yl | OH | H | H | OH |

TABLE 4-continued

| No. | $R^{1a}$ | $R^{5a}$ | $R^{5b}$ | $R^{6a}$ | $R^{6b}$ |
|---|---|---|---|---|---|
| 175 | 5-hydroxy-5-methylhex-3-ynyl | OH | H | H | OH |
| 176 | 4-(2-methyl-oxyranyl)-but-3-ynyl | OH | H | H | OH |
| 177 | 6-hydroxy-6-methylhept-3-yn-2-yl | OH | H | H | OH |
| 178 | 5-(2-methyloxyranyl)-pent-4-yn-2-yl | OH | H | H | OH |
| 179 | 5-hydroxy-5-ethylhept-3-ynyl | OH | H | H | OH |
| 180 | 6-hydroxy-6-ethyloctyn-4-yn-2-yl | OH | H | H | OH |

Compounds which comprise Category III of the present invention may also have the structural formula:

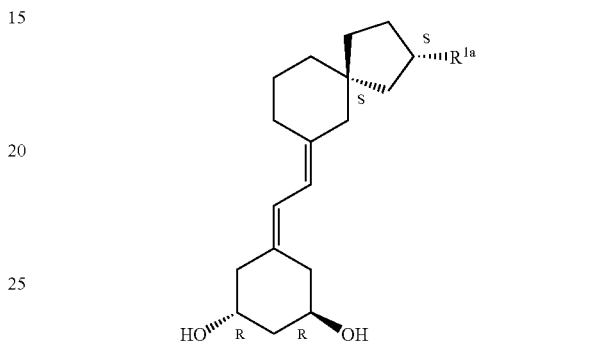

i.e. having the assigned (S,S) stereochemistry in the CF-Ring system. Non-limiting examples of $R^{1a}$ are found in Table 5 herein below.

TABLE 5

| No. | $R^{1a}$ |
|---|---|
| 83 | n-hexyl |
| 84 | 1-methylpentyl |
| 85 | 2-methylpentyl |
| 86 | 3-methyl-pentyl |
| 87 | 4-methylpentyl |
| 88 | 1,1-dimethylbutyl |
| 89 | 1,2-dimethylbutyl |
| 90 | 1,3-dimethylbutyl |
| 91 | 2,2-dimethylbutyl |
| 92 | 2,3-dimethylbutyl |
| 93 | 3,3-dimethylbutyl |
| 94 | 1-ethylbutyl |
| 95 | 2-ethylbutyl |
| 96 | n-heptyl |
| 97 | 1-methylhexyl |
| 98 | 2-methyl-hexyl |
| 99 | 3-methylhexyl |
| 100 | 4-methylhexyl |
| 101 | 5-methylhexyl |
| 102 | 1,1-dimethyl-pentyl |
| 103 | 1,2-dimethylpentyl |
| 104 | 1,3-dimethylpentyl |
| 105 | 1,4-dimethylpentyl |
| 106 | 2,2-dimethylpentyl |
| 107 | 2,3-dimethylpentyl |
| 108 | 4,4-dimethylpentyl |
| 109 | 1-hydroxy-4-methylpentan-1-yl |
| 110 | 2-hydroxy-4-methylpentan-1-yl |
| 111 | 3-hydroxy-4-methylpentan-1-yl |
| 112 | 4-hydroxy-4-methylpentan-1-yl |
| 113 | 1-hydroxy-5-methylhexan-2-yl |
| 114 | 2-hydroxy-5-methylhexan-2-yl |
| 115 | 3-hydroxy-5-methylhexan-2-yl |
| 116 | 4-hydroxy-5-methylhexan-2-yl |
| 117 | 5-hydroxy-5-methylhexan-2-yl |
| 118 | 1-hydroxy-6-methylheptan-2-yl |
| 119 | 2-hydroxy-6-methylheptan-2-yl |

TABLE 5-continued

| No. | R¹ᵃ |
|---|---|
| 120 | 3-hydroxy-6-methylheptan-2-yl |
| 121 | 4-hydroxy-6-methylheptan-2-yl |
| 122 | 5-hydroxy-6-methylheptan-2-yl |
| 123 | 6-hydroxy-6-methylheptan-2-yl |
| 124 | 1-hydroxy-1,5-dimethyl-hexan-1-yl |
| 125 | 1-hydroxy-5,5-dimethyl-hexan-1-yl |
| 126 | 4-methylpent-2-enyl |
| 127 | 5-methylhex-2-enyl |
| 128 | 5-methylhex-3-enyl |
| 129 | 4-ethylhex-2-enyl |
| 130 | 6-methylhept-2-enyl |
| 131 | 6-methylhept-3-enyl |
| 132 | 6-methylhept-4-enyl |
| 133 | 7-methyloct-4-en-2-yl |
| 134 | 6-ethyloct-2-enyl |
| 135 | 6-ethyloct-3-enyl |
| 136 | 6-ethyloct-4-enyl |
| 137 | 4-hydroxy-4-methylpent-2-enyl |
| 138 | 4-cyano-4-methylpent-2-enyl |
| 139 | 5-hydroxy-5-methylhex-2-enyl |
| 140 | 5-hydroxy-5-methylhex-3-enyl |
| 141 | 4-hydroxy-4-ethylhex-2-enyl |
| 142 | 6-hydroxy-6-methylhept-2-enyl |
| 143 | 6-hydroxy-6-methylhept-3-enyl |
| 144 | 6-hydroxy-6-methylhept-4-enyl |
| 145 | 7-hydroxy-7-methyloct-4-en-2-yl |
| 146 | 7-hydroxy-7-methyloct-3,5-dien-2-yl |
| 147 | 6-hydroxy-6-ethyloct-2-enyl |
| 148 | 6-hydroxy-6-ethyloct-3-enyl |
| 149 | 6-hydroxy-6-ethyloct-4-enyl |
| 150 | 7-hydroxy-7-ethylnon-3,5-dien-2-yl |
| 151 | pent-2-ynyl |
| 152 | hex-2-yn-2-yl |
| 153 | hex-3-yn-2-yl |
| 154 | hex-4-yn-2-yl |
| 155 | 5-methylhex-3-ynyl |
| 156 | 6-methylhept-3-yn-2-yl |
| 157 | 5-ethylhept-3-ynyl |
| 158 | 6-ethyloctyn-4-yn-2-yl |
| 159 | 5-hydroxy-5-methylhex-3-ynyl |
| 160 | 4-(2-methyl-oxyranyl)-but-3-ynyl |
| 161 | 6-hydroxy-6-methylhept-3-yn-2-yl |
| 162 | 5-(2-methyl-oxyranyl)-pent-4-yn-2-yl |
| 163 | 5-hydroxy-5-ethylhept-3-ynyl |
| 164 | 6-hydroxy-6-ethyloctyn-4-yn-2-yl |

The (S,S) CF-Ring scaffold diastereomers which comprise Category III of this invention can be prepared while starting from intermediate 14b and utilizing procedures well known to those of skill in the art, for example, like the procedures described in Schemes II and III and in Examples 2 and 3 herein above. Scheme IV provides an outline of a synthetic procedure for making the diastereomer named (1R,3R)-5-{2-[(2S, 5S)-2-(4-hydroxy-4-methylpentyl)-spiro[4.5]dec-(7E)-ylidene]-ethylidene}-cyclo-hexane-1,3-diol (hereinafter referred as compound 33). This procedure includes a sequence of eight steps as follows. Each step will now be illustrated in details, based on specific starting compounds, reactive agents, catalysts, solvents, temperature ranges and the like, but the skilled person will understand that the specific materials and conditions disclosed herein may be replaced with similar or equivalent materials and conditions without significantly altering the resulting product of the relevant step.

Scheme IV

In a first step (a), the (1,4-dioxa-dispiro[4.1.4.3]tetradec-9-yl) methanol. stereoisomer intermediate (14b) (alternatively the corresponding (1,4-dithia-dispiro[4.1.4.3]tetradec-9-yl) methanol stereoisomer, not shown in this scheme) is activated for nucleophilic displacement, e.g. sulfonated in the presence of a suitable sulfonating agent and a solvent and optionally in the presence of an effective amount of a suitable catalyst:

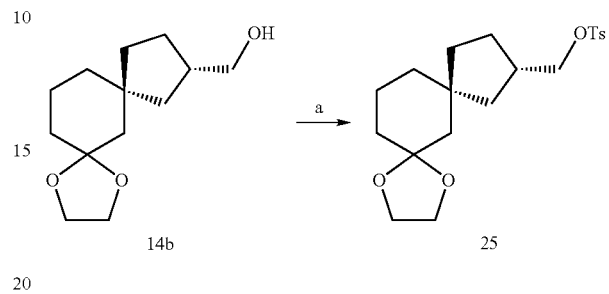

(preferred reagents and conditions for step (a): toluenesulfonyl or methanesulfonyl chloride as a sulfonating agent, dimethylaminopyridine (DMAP) as a catalyst, pyridine as a solvent; temperature ranging from about 10° C. to about 40° C.).

In a second step (b), the toluene-4-sulfonic acid 1,4-dioxadispiro[4.1.4.3]tetradec-9-ylmethyl ester stereoisomer (respectively the toluene-4-sulfonic acid 1,4-dithia-dispiro [4.1.4.3]tetradec-9-ylmethyl ester stereoisomer, not shown in this scheme) resulting from step (a) is submitted to a halo-desulfonyloxy-substitution somewhat similar to a Finkelstein reaction, preferably in the presence of a suitable solvent:

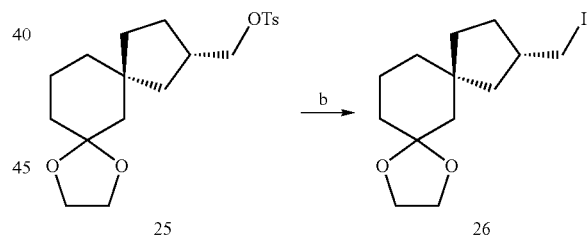

(preferred reagents and conditions for step (b): NaI, NaHCO₃, CH₃CN as a solvent; reflux temperature of the solvent; substitution may also be effected with a bromide or a chloride instead of an iodide).

In a third step (c), the 9-iodomethyl-1,4-dioxa-dispiro [4.1.4.3] tetradec-9-yl methyl ester stereoisomer (respectively the 9-iodomethyl-1,4-dithia-dispiro[4.1.4.3]tetradec-9-yl methyl ester stereoisomer, not shown in this scheme) resulting from step (b) is submitted to a 1,4-addition reaction by means of an α,β-ethylenically unsaturated carboxylic acid ester such as, but not limited to, a $C_1$-$C_8$ alkyl acrylate or $C_1$-$C_8$ alkyl methacrylate, preferably in the presence of a suitable solvent and optionally in the presence of a suitable catalyst:

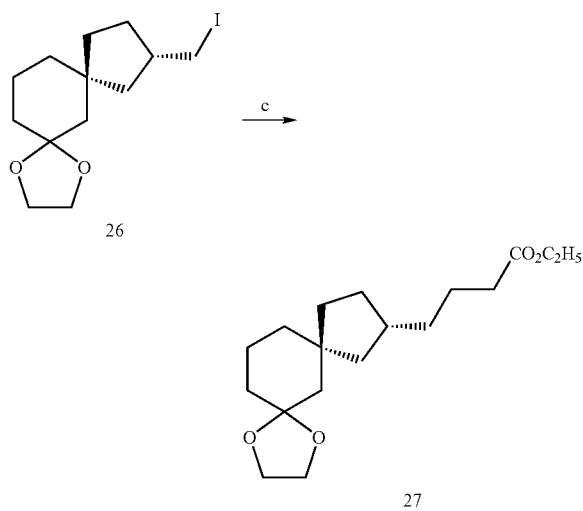

26

27

(preferred reagents and conditions for step (c): $CH_2=CHCO_2C_2H_5$, Zn and $NiCl_2.6H_2O$ as catalyst components, pyridine as a solvent; temperature ranging from about 10° C. to about 40° C.).

In a fourth step (d), the 4-(1,4-dioxa-dispiro[4.1.4.3]tetradec-9-yl)-butyric acid ethyl ester stereoisomer (respectively the 4-(1,4-dithia-dispiro[4.1.4.3]tetradec-9-yl)-butyric acid ethyl ester stereoisomer, not shown in this scheme) resulting from step (c) is alkylated, e.g. by reaction with a suitable organometallic species, preferably a Grignard reagent, preferably in the presence of a suitable solvent:

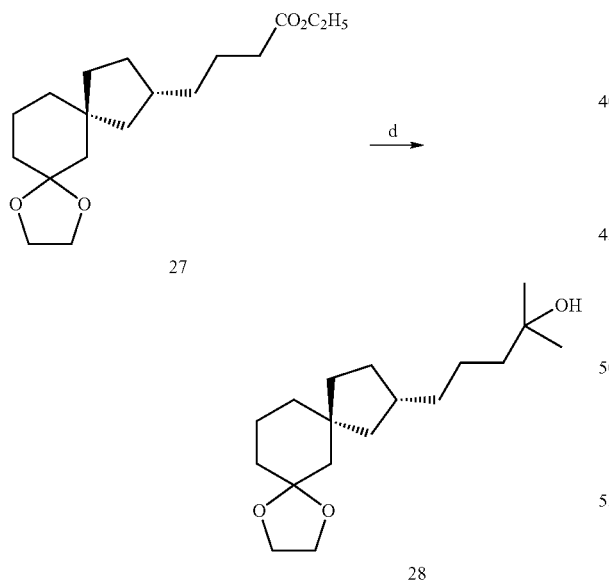

27

28

(preferred reagents and conditions for step (d): $CH_3MgBr$ as a Grignard reagent, THF as a solvent; temperature ranging from about 0° C. to about 40° C.).

In a fifth step (e), the 5-(1,4-dioxa-dispiro[4.1.4.3]tetradec-9-yl)-2-methyl pentanol stereoisomer (respectively the 5-(1,4-dithia-dispiro[4.1.4.3]tetradec-9-yl)-2-methyl pentanol stereoisomer, not shown in this scheme) resulting from step (d) is hydrolysed, preferably under acidic conditions and in the presence of an aqueous solvent:

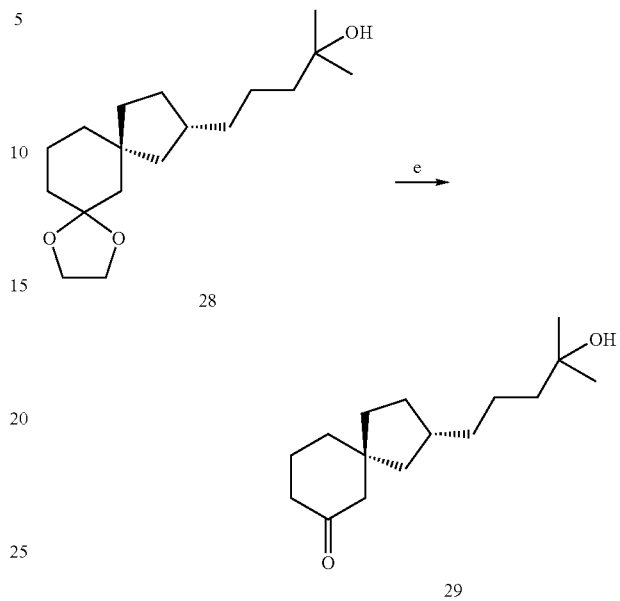

28

29

(preferred reagents and conditions for step (e): p-toluenesulfonic acid as an acidic catalyst, acetone/water as a solvent medium; temperature ranging from about 0° C. to about 40° C.).

In sixth step (f), an oxygen protecting group (such as described herein above in details) is positioned by using standard procedures well known in the art:

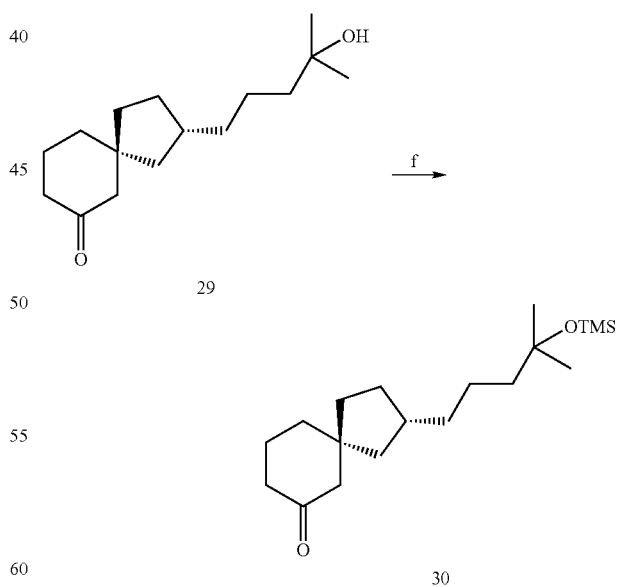

29

30

(preferred reagents and conditions for step (f): trimethylsilyl (TMS) ether as a protecting group-containing reagent, THF as a solvent; temperature ranging from about 10° C. to about 40° C.).

In a seventh step (g), the 2-(4-methyl-4-trimethylsilanyloxy-pentyl)-spiro[4.5]decan-7-one from step (f) is submitted to a Horner-Wittig reaction involving a phosphine oxide corresponding to the A-ring scaffold of the desired vitamin $D_3$ analog and wherein hydroxy groups are protected with conventional O-protecting groups (such as described hereinabove), optionally in the presence of an effective amount of a suitable catalyst (preferably an organometallic species derived from an alkaline metal such as, but not limited to, an alkyllithium) and optionally in the presence of a suitable solvent such as an ether:

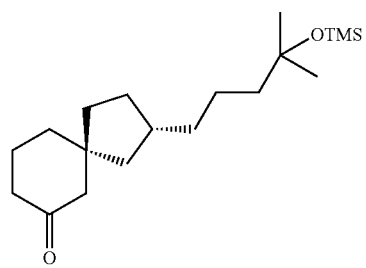

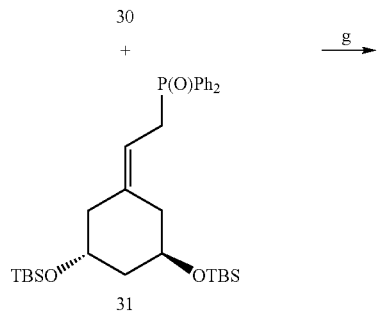

-continued

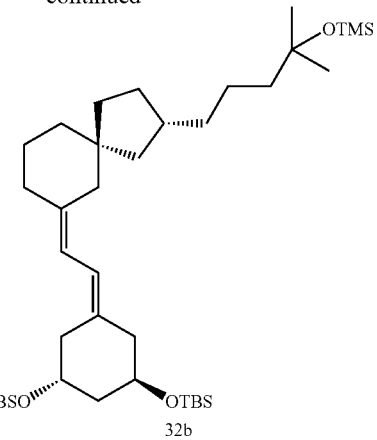

(preferred reagents and conditions for step (g): 5-[2-(diphenyl-phosphinoyl)-ethylidene]-bis-(tert-butyl-dimethyl-silanyloxy)-cyclohexane as a phosphine. oxide reagent, n-BuLi as a catalyst, THF as a solvent; temperature ranging from about 10° C. to about 40° C.).

Then in an eighth step (h), oxygen deprotection is effected under standard conditions for this kind of reaction:

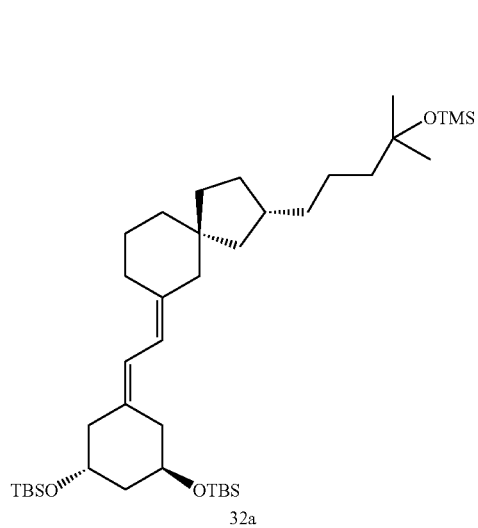

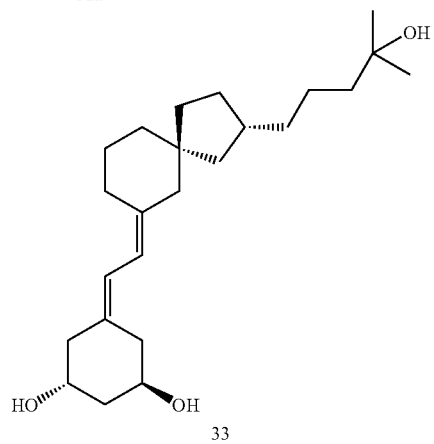

(preferred reagents and conditions: (c) tetrabutylammonium fluoride as a reagent; THF as a solvent; temperature ranging from about 10° C. to about 40° C.).

For the ease of understanding and the completion of the disclosure of other stereoisomers which are also available by this methodology, scheme IV' hereunder provides a full depiction of a similar synthetic route starting from the other stereoisomer (14b').
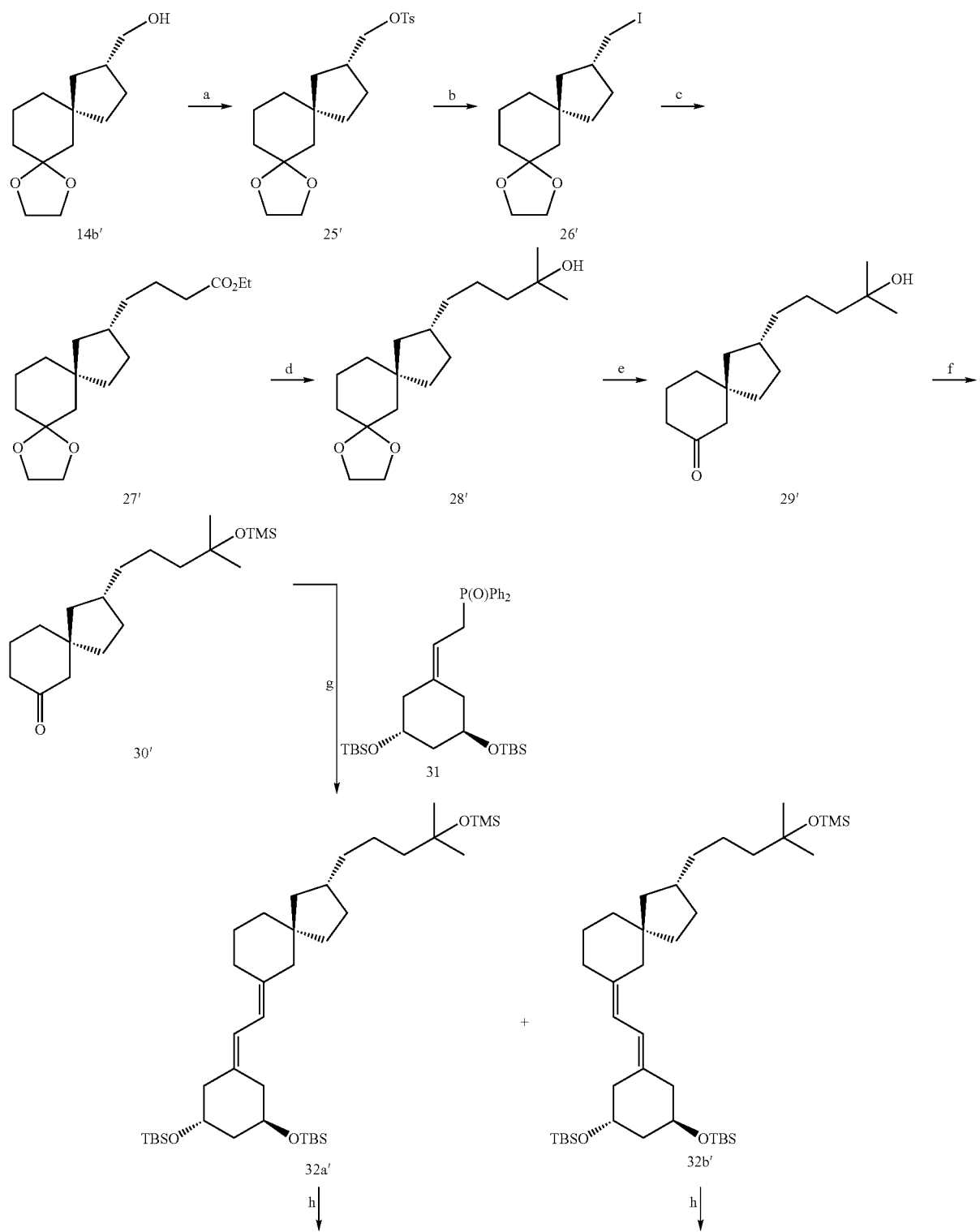
Scheme IV'

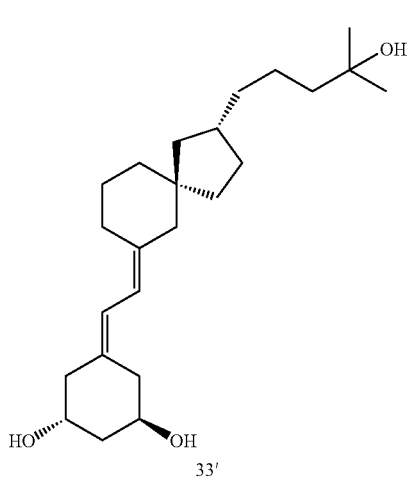

33'

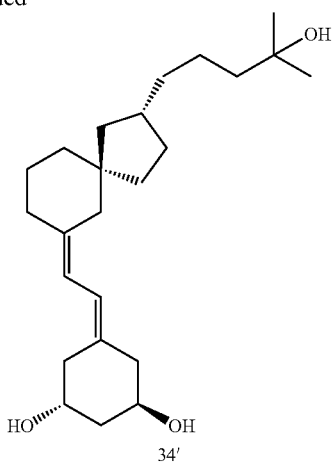

34'

The following example 4 includes characterizing data (such as optical rotation, infrared absorption bands and nuclear magnetic resonance spectra) of intermediates 26, 27, 28 and 29, and of the final vitamin $D_3$ analog 33 which have been prepared according to Scheme IV.

EXAMPLE 4

Preparation of (1R,3R)-5-{2-[(2R,5S)-2-(4-hydroxy-4-methyl-pentyl)-spiro[4.5]dec-(7E)-ylidene]-ethylidene}-cyclo-hexane-1.3-diol (33)

This preparation proceeds in eight steps according to scheme IV described hereinabove, and using the detailed process conditions of example 2, via the following fully characterized intermediates:

9-iodomethyl-1,4-dioxa-dispiro[4.1.4.3]tetradec-9-ylm-ethyl ester (26): the desired isomer was obtained via Scheme IV in 91% yield and characterized as follows:

$R_f$ (isooctane/EtOAc, 95:5) 0.30;

optical rotation at room temperature +15.7 (c=1.29, $CHCl_3$);

UV (MeOH) absorption at 254 nm;

IR (KBr film): 2934, 2865, 1444, 1424, 1362, 1317, 1275, 1205, 1182, 1103, 1082, 1057, 946, 836 and 586 $cm^{-1}$;

$^1$H NMR (500 MHz, $CDCl_3$): 3.94-3.89 (4 H, m), 3.23 (1 H, ABd, J=9.3, 6.4 Hz), 3.16 (1 H, ABd, J=9.3, 7.3 Hz), 2.25 (1 H, app. septet, J=7.9 Hz), 2.01 (1 H, dd, J=13.1, 8.1 Hz), 1.91-1.85 (1 H, m), 1.66-1.53 (8 H, m), 1.42-1.25 (3 H, m), and 1.04 (1 H, dd, J=13.1, 9.3 Hz) ppm;

$^{13}$C NMR (75 MHz, $CDCl_3$): 109.4 (C), 64.1 ($CH_2$), 64.0 ($CH_2$), 46.0 ($CH_2$), 45.3 ($CH_2$), 44.4 (C), 41.7 (CH), 39.0 ($CH_2$), 38.3 ($CH_2$), 35.0 ($CH_2$), 32.3 ($CH_2$), 21.0 ($CH_2$) and 14.6 ($CH_2$) ppm;

MS m/z (%): 336 ($M^+$, 3), 293 (42), 209 (38), 99 (100), 86 (22), 79 (11), 55 (21) and 41 (18); and elemental analysis: calculated for $C_{13}H_{21}IO_2$: C, 46.44; H, 6.30; found: C, 46.27; H, 6.41.

4-(1,4-dioxa-dispiro[4.1.4.3]tetradec-9-yl)-butyric acid ethyl ester (27): the desired isomer was obtained via Scheme IV in 91% yield and characterized as follows:

$R_f$ (isooctane/EtOAc, 9:1) 0.23;

optical rotation at room temperature: +5.7 (c=1.66, $CHCl_3$);

IR (KBr film): 2934, 2869, 1737, 1446, 1369, 1246, 1175, 1103, 1056 and 946 $cm^{-1}$;

$^1$H NMR (500 MHz, $CDCl_3$): 4.12 (2 H, q, J=7.1 Hz), 3.91 (4 H, s), 2.27 (1 H, t, J=7.6 Hz), 1.93-1.82 (2 H, m), 1.80-1.74 (1 H, m), 1.64-1.46 (10 H, m), 1.36-1.29 (4 H, m), 1.25 (3 H, t, J=7.1 Hz), 1.19-1.11 (1 H, m) and 0.94-0.91 (1 H, m) ppm;

$^{13}$C NMR (75 MHz, $CDCl_3$): 173.9 (C), 109.6 (C), 64.0 ($CH_2$), 60.2 ($CH_2$), 46.1 ($CH_2$), 46.2 ($CH_2$), 43.4 (C), 39.0 ($CH_2$), 38.7 (CH), 38.6 ($CH_2$), 36.3 ($CH_2$), 35.1 ($CH_2$), 34.6 ($CH_2$), 31.5 ($CH_2$), 24.1 ($CH_2$), 21.1 ($CH_2$) and 1.43 ($CH_2$) ppm; and MS m/z (%): 310 ($M^+$, <1), 267 (56), 195 (3), 167 (3), 151 (3), 113 (9), 99 (100), 86 (22), 55 (18) and 41 (12).

5-(1,4-dioxa-dispiro[4 1.4.3]tetradec-9-yl)-2-methyl-pentan-2-ol (28): the desired isomer was obtained via Scheme IV in 86% yield and characterized as follows:

$R_f$ (cyclohexane/EtOAc, 8:2) 0.26;

optical rotation at room temperature: +4.9 (c=0.95, $CHCl_3$);

IR (KBr film): 3438, 2932, 2868, 1445, 1362, 1317, 1279, 1173, 1100, 1056, 946, 908, 857 and 836 $cm^{-1}$;

$^1$H NMR (500 MHz, $CDCl_3$): 3.94-3.89 (4 H, m), 1.92-1.85 (2 H, m), 1.79-1.73 (1 H, m), 1.63-1.42 (11 H, m),.. 1.38-1.24 (6 H, m), 1.20 (6 H, s), 1.17-1.13 (1 H, m) and 0.95-0.88 (1 H, m) ppm;

$^{13}$C NMR (75 MHz, $CDCl_3$): 109.6 (C), 71.1 (C), 64.0 ($CH_2$), 45.9 ($CH_2$), 45.4 ($CH_2$), 44.2 ($CH_2$), 43.5 (C), 39.0 ($CH_2$), 38.6.(CH), 37.4 ($CH_2$), 35.1 ($CH_2$), 31.6 ($CH_2$), 29.3 ($CH_3$), 23.5 ($CH_2$) and 21.2 ($CH_2$) ppm; and MS m/z (%): 281 (2), 253 (25), 195 (4), 167 (3), 151 (3), 113 (9), 99 (100), 86 (22), 55 (18) and 41 (12).

2-(4-hydroxy-4-methylpentyl)-spiro[4.5]decan-7-one (29): the desired isomer was obtained via Scheme IV in 87% yield and characterized as follows:

$R_f$ (isooctane/EtOAc, 4:6) 0.43;

optical rotation at room temperature: +3.3 (c=0.89, $CHCl_3$); −3.1 (c=0.90, $CHCl_3$);

IR (KBr film): 3436, 2934, 2863, 1706, 1460, 1443, 1425, 1376, 1311, 1288, 1228, 1176, 1156, 1078, 1025, 937 and 909 $cm^{-1}$;

$^1$H NMR (500 MHz, $CDCl_3$): 2.30-2.24 (2 H, m), 2.23 (2 H, s), 1.96-1.79 (4 H, m), 1.68-1.64 (3 H, m), 1.53 (1 H, ddd, J=13.3, 9.1, 4.8 Hz), 1.44-1.40 (3 H, m), 1.35-1.25 (5 H, m), 1.22-1.16 (1 H, m), 1.19 (6 H, s) and 0.97 (1 H, dd, J=12.6, 10.3 Hz) ppm;
$^{13}$C NMR (75 MHz, CDCl$_3$): 212.1 (C), 70.9 (C), 53.7 (CH$_2$), 47.3 (C), 45.3 (CH$_2$), 44.1 (CH$_2$), 41.2 (CH$_2$), 38.8 (CH), 38.2 (CH$_2$), 38.1 (CH$_2$), 36.9 (CH$_2$), 31.4 (CH$_2$), 29.3 (CH$_3$), 23.8 (CH$_2$) and 23.4 (CH$_2$) ppm; and
MS m/z (%): 237 (7), 234 (3), 194 (6), 176 (12), 161 (9), 136 (18), 123 (10), 110 (18), 93 (31), 81 (16), 79 (16), 59 (100), 55 (31), 43 (30) and 41 (30).

(1R,3R)-5-{2-[(2S,5S)-2-(4-Hydroxy-4-methyl-pentyl)-spiro[4.5]dec-(7E)-ylidene]-ethylidene}-cyclo-hexane-1,3-diol (33) was characterized as follows:
R$_f$ (CH$_2$Cl$_2$/Me$_2$CO, 6:4) 0.37;
UV (MeOH) absorption at 259, 249, 242 nm;
IR (KBr film): 3342, 2929, 2857, 1616, 1444, 1360, 1221, 1152, 1049, 975, 908 and 733 cm$^{-1}$;
$^1$H NMR (500 MHz, CDCl$_3$): 6.23 (1 H, A$\underline{B}$, J=11.2 Hz), 5.93 (1 H, A$\underline{B}$, J=11.2 Hz), 4.11-4.03 (2 H, m), 2.68 (1 H, dd, J=13.2, 3.7 Hz), 2.47 (1 H, dd, J=13.3, 3.6 Hz), 2.32-2.28 (1 H, m), 2.25 (1 H, dd, J=13.2, 7.9 Hz), 2.19 (1 H, dd, J=13.3, 6.3 Hz), 2.14-2.09 (1 H, m), 1.98 (2 H, s), 1.93-1.66 (7. H, m), 1.55-1.25 (13 H, m), 1.20 (6 H, s), 1.20-1.11 (1 H, m) and 0.79 (1 H, dd, J=10.4, 12.5 Hz) ppm;
$^{13}$C NMR (75 MHz, CDCl$_3$): 141.9 (C), 131.5 (C), 123.8 (CH), 118.2 (CH), 71.2 (C), 67.5 (CH), 67.1 (CH), 49.6 (CH$_2$), 45.2 (C), 44.8 (CH$_2$), 44.7 (CH$_2$), 42.2 (CH$_2$), 39.9 (CH$_2$), 38.8 (CH$_2$), 38.1 (CH), 37.2 (CH$_2$), 36.9 (CH$_2$), 31.7 (CH$_2$), 29.3 (CH$_3$), 29.1 (CH$_3$), 28.7 (CH$_2$), 24.7 (CH$_2$) and 23.4 (CH$_2$) ppm; and
MS m/z (%): 358 (M$^+$—H$_2$O, 94), 340 (22), 281 (10), 207 (28), 163 (24), 145 (36), 119 (30), 107 (32), 105 (34), 93 (58), 91 (61), 69 (56), 67 (56), 55 (54), 43 (49) and 41 (100).

Compounds which are comprised in category IV of the present invention include, but are not limited to, the Z-isomers of 5-[2-(2-R$^{1a}$-substituted-spiro[4.5]dec-7-ylidene)-ethylidene]-cyclohexane-1,3-diols having the following structural formula:

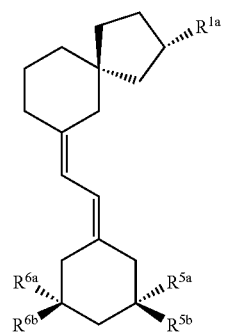

wherein the R$^{1a}$ substitutions at carbon 20 of the molecule are outlined herein below in Table 6.

TABLE 6

| No. | R$^{1b}$ | R$^{5a}$ | R$^{5b}$ | R$^{6a}$ | R$^{6b}$ |
|---|---|---|---|---|---|
| 181 | 4-hydroxy-4-methylpentyl | H | OH | OH | H |
| 182 | 5-hydroxy-5-methylhex-2-yl | H | OH | OH | H |
| 183 | 6-hydroxy-6-methylhept-2-yl | H | OH | OH | H |
| 184 | 5-hydroxy-6-methylhept-2-yl | H | OH | OH | H |

TABLE 6-continued

| No. | R$^{1b}$ | R$^{5a}$ | R$^{5b}$ | R$^{6a}$ | R$^{6b}$ |
|---|---|---|---|---|---|
| 185 | 1-hydroxy-5,5-dimethylhexyl | H | OH | OH | H |
| 186 | 7-hydroxy-7-methyloct-4-en-2-yl | H | OH | OH | H |
| 187 | 7-hydroxy-7-ethylnon-4-en-2-yl | H | OH | OH | H |
| 188 | 7-hydroxy-7-ethylnon-4-en-2-yl | H | OH | OH | H |
| 189 | 7-hydroxy-7-ethylnon-3,5-dien-2-yl | H | OH | OH | H |
| 190 | 5-hydroxy-5-methylhex-3-ynyl | H | OH | OH | H |
| 191 | 4-(2-methyl-oxyranyl)-but-3-ynyl | H | OH | OH | H |
| 192 | 6-hydroxy-6-methylhept-3-yn-2-yl | H | OH | OH | H |
| 193 | 5-(2-methyloxyranyl)-pent-4-yn-2-yl | H | OH | OH | H |
| 194 | 5-hydroxy-5-ethylhept-3-ynyl | H | OH | OH | H |
| 195 | 6-hydroxy-6-ethyloctyn-4-yn-2-yl | H | OH | OH | H |
| 196 | 4-hydroxy-4-methylpentyl | OH | H | OH | H |
| 197 | 5-hydroxy-5-methylhex-2-yl | OH | H | OH | H |
| 198 | 6-hydroxy-6-methylhept-2-yl | OH | H | OH | H |
| 199 | 5-hydroxy-6-methylhept-2-yl | OH | H | OH | H |
| 200 | 1-hydroxy-5,5-dimethylhexyl | OH | H | OH | H |
| 201 | 7-hydroxy-7-methyloct-4-en-2-yl | OH | H | OH | H |
| 202 | 7-hydroxy-7-ethylnon-4-en-2-yl | OH | H | OH | H |
| 203 | 7-hydroxy-7-ethylnon-4-en-2-yl | OH | H | OH | H |
| 204 | 7-hydroxy-7-ethylnon-3,5-dien-2-yl | OH | H | OH | H |
| 205 | 5-hydroxy-5-methylhex-3-ynyl | OH | H | OH | H |
| 206 | 4-(2-methyl-oxyranyl)-but-3-ynyl | OH | H | OH | H |
| 207 | 6-hydroxy-6-methylhept-3-yn-2-yl | OH | H | OH | H |
| 208 | 5-(2-methyloxyranyl)-pent-4-yn-2-yl | OH | H | OH | H |
| 209 | 5-hydroxy-5-ethylhept-3-ynyl | OH | H | OH | H |
| 210 | 6-hydroxy-6-ethyloctyn-4-yn-2-yl | OH | H | OH | H |
| 211 | 4-hydroxy-4-methylpentyl | H | OH | OH | H |
| 212 | 5-hydroxy-5-methylhex-2-yl | H | OH | OH | H |
| 213 | 6-hydroxy-6-methylhept-2-yl | H | OH | OH | H |
| 214 | 5-hydroxy-6-methylhept-2-yl | H | OH | OH | H |
| 215 | 1-hydroxy-5,5-dimethylhexyl | H | OH | OH | H |
| 216 | 7-hydroxy-7-methyloct-4-en-2-yl | H | OH | OH | H |
| 217 | 7-hydroxy-7-ethylnon-4-en-2-yl | H | OH | OH | H |
| 218 | 7-hydroxy-7-ethylnon-4-en-2-yl | H | OH | OH | H |
| 219 | 7-hydroxy-7-ethylnon-3,5-dien-2-yl | H | OH | OH | H |
| 220 | 5-hydroxy-5-methylhex-3-ynyl | H | OH | OH | H |
| 221 | 4-(2-methyl-oxyranyl)-but-3-ynyl | H | OH | OH | H |
| 222 | 6-hydroxy-6-methylhept-3-yn-2-yl | H | OH | OH | H |
| 223 | 5-(2-methyloxyranyl)-pent-4-yn-2-yl | H | OH | OH | H |
| 224 | 5-hydroxy-5-ethylhept-3-ynyl | H | OH | OH | H |
| 225 | 6-hydroxy-6-ethyloctyn-4-yn-2-yl | H | OH | OH | H |
| 226 | 4-hydroxy-4-methylpentyl | OH | H | H | OH |
| 227 | 5-hydroxy-5-methylhex-2-yl | OH | H | H | OH |
| 228 | 6-hydroxy-6-methylhept-2-yl | OH | H | H | OH |
| 229 | 5-hydroxy-6-methylhept-2-yl | OH | H | H | OH |
| 230 | 1-hydroxy-5,5-dimethylhexyl | OH | H | H | OH |
| 231 | 7-hydroxy-7-methyloct-4-en-2-yl | OH | H | H | OH |
| 232 | 7-hydroxy-7-ethylnon-4-en-2-yl | OH | H | H | OH |
| 233 | 7-hydroxy-7-ethylnon-4-en-2-yl | OH | H | H | OH |
| 234 | 7-hydroxy-7-ethylnon-3,5-dien-2-yl | OH | H | H | OH |
| 235 | 5-hydroxy-5-methylhex-3-ynyl | OH | H | H | OH |
| 236 | 4-(2-methyl-oxyranyl)-but-3-ynyl | OH | H | H | OH |
| 237 | 6-hydroxy-6-methylhept-3-yn-2-yl | OH | H | H | OH |
| 238 | 5-(2-methyloxyranyl)-pent-4-yn-2-yl | OH | H | H | OH |
| 239 | 5-hydroxy-5-ethylhept-3-ynyl | OH | H | H | OH |
| 240 | 6-hydroxy-6-ethyloctyn-4-yn-2-yl | OH | H | H | OH |

Compounds which are comprised in category IV of this invention can be conveniently obtained in the form of a mixture of isomers together with the corresponding E-isomer (i.e. compound of category III) and then isolated therefrom by preparative HPLC. The following non-limiting exemplary compound can thus be prepared according to Scheme IV herein above and isolated as part of the purification of compound 33:

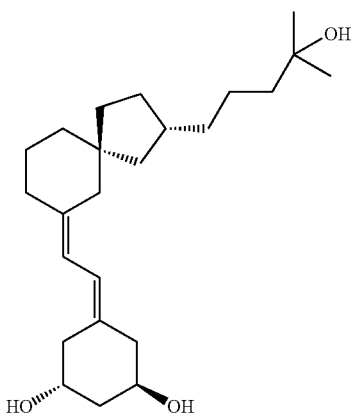

34

(1R,3R)-5-{2-[(2R,5S)-2-(4-hydroxy-4-methyl-pentyl)-spiro[4.5]dec-(7Z)-ylidene]-ethylidene}-cyclo-hexane-1,3-diol, compound 34, was characterized as follows:

$R_f$ (CH$_2$Cl$_2$/Me$_2$CO, 6:4) 0.37;

UV (MeOH) absorption at 259, 249 and 242 nm;

IR (KBr film): 3359, 2928, 2859, 1617, 1440, 1376, 1338, 1301, 1216, 1047, 976, 912 and 736 cm$^{-1}$;

$^1$H NMR (500 MHz, CDCl$_3$): 6.22 (1 H, AB, J=11.1 Hz), 6.07 (1 H, AB, J=11.1 Hz), 4.10-4.05 (2 H, m), 2.55 (1 H, dd,. J=13.4, 3.6 Hz), 2.51 (1 H, dd, J=13.0, 3.8 Hz), 2.38 (1 H, dd, J=13.4, 6.9 Hz), 2.23 (1 H, AB, J=13.1 Hz), 2.17 (1 H, dd, J=13.0, 7.5 Hz), 2.13-2.07 (2 H, m), 2.03 (1 H, AB, J=13.1 Hz), 1.95-1.87 (2 H, m), 1.85-1.79 (2 H, m), 1.66 (1 H, dd, J=12.5, 7.0 Hz), 1.59-1.25 (15 H, m), 1.21 (6 H, s), 1.20-1.14 (1 H, m) and 0.80 (1 H, dd, J=12.4,.10.5 Hz) ppm;

$^{13}$C NMR (75 MHz, CDCl$_3$): 142.3 (C), 131.5 (C), 123.9 (CH), 118.3 (CH), 71.1 (C), 67.5 (CH), 45.5 (CH$_2$), 45.3 (C), 44.7 (CH$_2$), 44.2 (CH$_2$), 42.1 (CH$_2$), 40.8 (CH$_2$), 40.0 (CH$_2$), 39.0 (CH), 38.1 (CH$_2$), 37.3 (CH$_2$), 37.0 (CH$_2$), 36.8 (CH$_2$), 31.7 (CH$_2$), 29.3 (CH$_3$), 29.2 (CH$_3$), 25.7 (CH$_2$) and 23.5 (CH$_2$) ppm; and MS m/z (%): 358 (M$^+$—H$_2$O, 16), 340 (10), 261 (9), 243 (7), 217 (8), 177 (47), 145 (26), 105 (44), 93 (68), 91 (60), 79 (55), 67 (59), 59 (98), 55 (65), 43 (100) and 41 (70).

Compounds which are comprised in category V of the present invention include, but are not limited to, the E-isomers of 5-[2-(2-R$^{2a}$-substituted-spiro[4.5]dec-7-ylidene)-ethylidene]-cyclohexane-1,3-diols having the following structural formula:

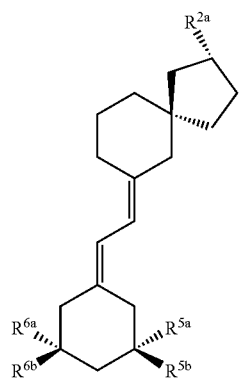

wherein the R$^{2a}$ substitutions are outlined herein below in Table 7.

TABLE 7

| R$^{2a}$ | R$^{5a}$ | R$^{5b}$ | R$^{6a}$ | R$^{6b}$ |
|---|---|---|---|---|
| 4-hydroxy-4-methylpentyl | H | OH | OH | H |
| 5-hydroxy-5-methylhex-2-yl | H | OH | OH | H |
| 6-hydroxy-6-methylhept-2-yl | H | OH | OH | H |
| 5-hydroxy-6-methylhept-2-yl | H | OH | OH | H |
| 1-hydroxy-5,5-dimethylhexyl | H | OH | OH | H |
| 7-hydroxy-7-methyloct-4-en-2-yl | H | OH | OH | H |
| 7-hydroxy-7-ethylnon-4-en-2-yl | H | OH | OH | H |
| 7-hydroxy-7-ethylnon-4-en-2-yl | H | OH | OH | H |
| 7-hydroxy-7-ethylnon-3,5-dien-2-yl | H | OH | OH | H |
| 5-hydroxy-5-methylhex-3-ynyl | H | OH | OH | H |
| 4-(2-methyl-oxyranyl)-but-3-ynyl | H | OH | OH | H |
| 6-hydroxy-6-methylhept-3-yn-2-yl | H | OH | OH | H |
| 5-(2-methyloxyranyl)-pent-4-yn-2-yl | H | OH | OH | H |
| 5-hydroxy-5-ethylhept-3-ynyl | H | OH | OH | H |
| 6-hydroxy-6-ethyloctyn-4-yn-2-yl | H | OH | OH | H |
| 4-hydroxy-4-methylpentyl | OH | H | OH | H |
| 5-hydroxy-5-methylhex-2-yl | OH | H | OH | H |
| 6-hydroxy-6-methylhept-2-yl | OH | H | OH | H |
| 5-hydroxy-6-methylhept-2-yl | OH | H | OH | H |
| 1-hydroxy-5,5-dimethylhexyl | OH | H | OH | H |
| 7-hydroxy-7-methyloct-4-en-2-yl | OH | H | OH | H |
| 7-hydroxy-7-ethylnon-4-en-2-yl | OH | H | OH | H |
| 7-hydroxy-7-ethylnon-4-en-2-yl | OH | H | OH | H |
| 7-hydroxy-7-ethylnon-3,5-dien-2-yl | OH | H | OH | H |
| 5-hydroxy-5-methylhex-3-ynyl | OH | H | OH | H |
| 4-(2-methyl-oxyranyl)-but-3-ynyl | OH | H | OH | H |
| 6-hydroxy-6-methylhept-3-yn-2-yl | OH | H | OH | H |
| 5-(2-methyloxyranyl)-pent-4-yn-2-yl | OH | H | OH | H |
| 5-hydroxy-5-ethylhept-3-ynyl | OH | H | OH | H |
| 6-hydroxy-6-ethyloctyn-4-yn-2-yl | OH | H | OH | H |
| 4-hydroxy-4-methylpentyl | H | OH | OH | H |
| 5-hydroxy-5-methylhex-2-yl | H | OH | OH | H |
| 6-hydroxy-6-methylhept-2-yl | H | OH | OH | H |
| 5-hydroxy-6-methylhept-2-yl | H | OH | OH | H |
| 1-hydroxy-5,5-dimethylhexyl | H | OH | OH | H |
| 7-hydroxy-7-methyloct-4-en-2-yl | H | OH | OH | H |
| 7-hydroxy-7-ethylnon-4-en-2-yl | H | OH | OH | H |
| 7-hydroxy-7-ethylnon-4-en-2-yl | H | OH | OH | H |
| 7-hydroxy-7-ethylnon-3,5-dien-2-yl | H | OH | OH | H |
| 5-hydroxy-5-methylhex-3-ynyl | H | OH | OH | H |
| 4-(2-methyl-oxyranyl)-but-3-ynyl | H | OH | OH | H |
| 6-hydroxy-6-methylhept-3-yn-2-yl | H | OH | OH | H |
| 5-(2-methyloxyranyl)-pent-4-yn-2-yl | H | OH | OH | H |
| 5-hydroxy-5-ethylhept-3-ynyl | H | OH | OH | H |
| 6-hydroxy-6-ethyloctyn-4-yn-2-yl | H | OH | OH | H |
| 4-hydroxy-4-methylpentyl | OH | H | H | OH |
| 5-hydroxy-5-methylhex-2-yl | OH | H | H | OH |
| 6-hydroxy-6-methylhept-2-yl | OH | H | H | OH |
| 5-hydroxy-6-methylhept-2-yl | OH | H | H | OH |
| 1-hydroxy-5,5-dimethylhexyl | OH | H | H | OH |
| 7-hydroxy-7-methyloct-4-en-2-yl | OH | H | H | OH |
| 7-hydroxy-7-ethylnon-4-en-2-yl | OH | H | H | OH |
| 7-hydroxy-7-ethylnon-4-en-2-yl | OH | H | H | OH |
| 7-hydroxy-7-ethylnon-3,5-dien-2-yl | OH | H | H | OH |
| 5-hydroxy-5-methylhex-3-ynyl | OH | H | H | OH |
| 4-(2-methyl-oxyranyl)-but-3-ynyl | OH | H | H | OH |
| 6-hydroxy-6-methylhept-3-yn-2-yl | OH | H | H | OH |
| 5-(2-methyloxyranyl)-pent-4-yn-2-yl | OH | H | H | OH |
| 5-hydroxy-5-ethylhept-3-ynyl | OH | H | H | OH |
| 6-hydroxy-6-ethyloctyn-4-yn-2-yl | OH | H | H | OH |

Other representative but not limiting compounds which comprise Category V of the present invention have the structural formula:

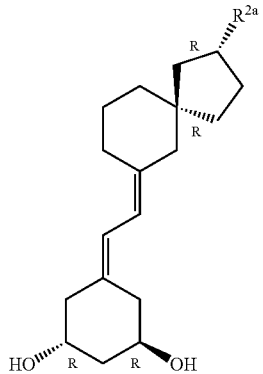

having the assigned (R,R) stereochemistry in the CF-Ring system. Non-limiting examples of $R^{2a}$ are found in Table. 8 herein below.

TABLE 8

| No. | $R^{2a}$ |
|---|---|
| 165 | n-hexyl |
| 166 | 1-methylpentyl |
| 167 | 2-methylpentyl |
| 168 | 3-methyl-pentyl |
| 169 | 4-methylpentyl |
| 170 | 1,1-dimethylbutyl |
| 171 | 1,2-dimethylbutyl |
| 172 | 1,3-dimethylbutyl |
| 173 | 2,2-dimethylbutyl |
| 174 | 2,3-dimethylbutyl |
| 175 | 3,3-dimethylbutyl |
| 176 | 1-ethylbutyl |
| 177 | 2-ethylbutyl |
| 178 | n-heptyl |
| 179 | 1-methylhexyl |
| 180 | 2-methyl-hexyl |
| 181 | 3-methylhexyl |
| 182 | 4-methylhexyl |
| 183 | 5-methylhexyl |
| 184 | 1,1-dimethyl-pentyl |
| 185 | 1,2-dimethylpentyl |
| 186 | 1,3-dimethylpentyl |
| 187 | 1,4-dimethylpentyl |
| 188 | 2,2-dimethylpentyl |
| 189 | 2,3-dimethylpentyl |
| 190 | 4,4-dimethylpentyl |
| 191 | 1-hydroxy-4-methylpentan-1-yl |
| 192 | 2-hydroxy-4-methylpentan-1-yl |
| 193 | 3-hydroxy-4-methylpentan-1-yl |
| 194 | 4-hydroxy-4-methylpentan-1-yl |
| 195 | 1-hydroxy-5-methylhexan-2-yl |
| 196 | 2-hydroxy-5-methylhexan-2-yl |
| 197 | 3-hydroxy-5-methylhexan-2-yl |
| 198 | 4-hydroxy-5-methylhexan-2-yl |
| 199 | 5-hydroxy-5-methylhexan-2-yl |
| 200 | 1-hydroxy-6-methylheptan-2-yl |
| 201 | 2-hydroxy-6-methylheptan-2-yl |
| 202 | 3-hydroxy-6-methylheptan-2-yl |
| 203 | 4-hydroxy-6-methylheptan-2-yl |
| 204 | 5-hydroxy-6-methylheptan-2-yl |
| 205 | 6-hydroxy-6-methylheptan-2-yl |
| 206 | 1-hydroxy-1,5-dimethyl-hexan-1-yl |
| 207 | 1-hydroxy-5,5-dimethyl-hexan-1-yl |
| 208 | 4-methylpent-2-enyl |
| 209 | 5-methylhex-2-enyl |
| 210 | 5-methylhex-3-enyl |
| 211 | 4-ethylhex-2-enyl |

TABLE 8-continued

| No. | $R^{2a}$ |
|---|---|
| 212 | 6-methylhept-2-enyl |
| 213 | 6-methylhept-3-enyl |
| 214 | 6-methylhept-4-enyl |
| 215 | 7-methyloct-4-en-2-yl |
| 216 | 6-ethyloct-2-enyl |
| 217 | 6-ethyloct-3-enyl |
| 218 | 6-ethyloct-4-enyl |
| 219 | 4-hydroxy-4-methylpent-2-enyl |
| 220 | 4-cyano-4-methylpent-2-enyl |
| 221 | 5-hydroxy-5-methylhex-2-enyl |
| 222 | 5-hydroxy-5-methylhex-3-enyl |
| 223 | 4-hydroxy-4-ethylhex-2-enyl |
| 224 | 6-hydroxy-6-methylhept-2-enyl |
| 225 | 6-hydroxy-6-methylhept-3-enyl |
| 226 | 6-hydroxy-6-methylhept-4-enyl |
| 227 | 7-hydroxy-7-methyloct-4-en-2-yl |
| 228 | 7-hydroxy-7-methyloct-3,5-dien-2-yl |
| 229 | 6-hydroxy-6-ethyloct-2-enyl |
| 230 | 6-hydroxy-6-ethyloct-3-enyl |
| 231 | 6-hydroxy-6-ethyloct-4-enyl |
| 232 | 7-hydroxy-7-ethylnon-3,5-dien-2-yl |
| 233 | pent-2-ynyl |
| 234 | hex-2-yn-2-yl |
| 235 | hex-3-yn-2-yl |
| 236 | hex-4-yn-2-yl |
| 237 | 5-methylhex-3-ynyl |
| 238 | 6-methylhept-3-yn-2-yl |
| 239 | 5-ethylhept-3-ynyl |
| 240 | 6-ethyloctyn-4-yn-2-yl |
| 241 | 5-hydroxy-5-methylhex-3-ynyl |
| 242 | 4-(2-methyl-oxyranyl)-but-3-ynyl |
| 243 | 6-hydroxy-6-methylhept-3-yn-2-yl |
| 244 | 5-(2-methyl-oxyranyl)-pent-4-yn-2-yl |
| 245 | 5-hydroxy-5-ethylhept-3-ynyl |
| 246 | 6-hydroxy-6-ethyloctyn-4-yn-2-yl |

The (R,R) CF-Ring scaffold diastereomers which comprise compounds of Category V of the present invention can be prepared beginning with intermediate 2 and utilizing procedures well known to those of skill in the art and as described in the schemes herein such as schemes I', II' and IV'.

The following scheme V provides an outline of the synthetic procedure for making the diastereomer (1R,3R)-5-{2-[(2R,5R)-2-(4-hydroxy-4-methyl-pentyl)-spiro[4.5]dec-(7E)-ylidene]-ethylidene}-cyclohexane-1,3-diol which is described in detail in Example 5. The procedure described herein below provides an example of how the (R,R) and (R,S) diastereomers can be conveniently separated further in the synthesis, for example, in step (p). Each synthetic step will now be illustrated in details, based on specific starting compounds, reactive agents, catalysts, solvents, temperature ranges and the like, but the skilled person will understand that the specific materials and conditions disclosed herein may be replaced with similar or equivalent materials and conditions without significantly altering the resulting product of the relevant step, except perhaps for the reaction yield or, in the case of a stereoselective reaction, the enantiomeric excess of the product shown.

Scheme V

As indicated above, the first steps of this scheme are very similar to the corresponding steps of scheme I, therefore only the schemes of these steps will be shown for brevity:

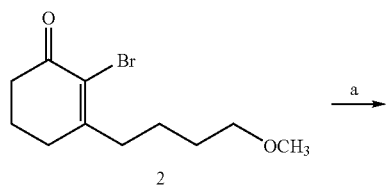

(preferred conditions for step (a) as shown above: (R)-metyloxazaborolidinone as a catalyst, catecholborane as a reducing agent, toluene as a solvent; temperature range from about −95° C. to about 25° C., more preferably from −78° C. to about 0° C.).

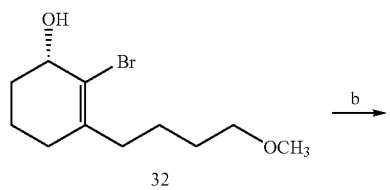

(preferred reagents and conditions for step (b): $(CH_3)_2N[CCH_3(OCH_3)_2]$ as a reagent, toluene as a solvent; temperature: reflux of the solvent).

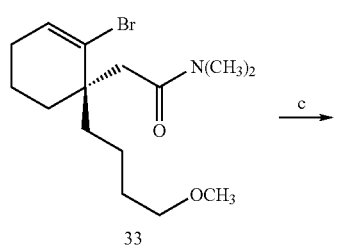

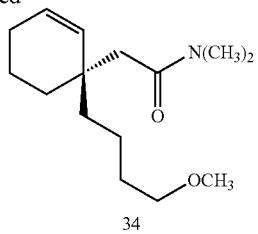

(preferred reagents and conditions for step (c): $Bu_3SnH$ as the reducing agent, azobis-isobutyronitrile as a free radical initiator; THF a solvent; temperature: reflux of the solvent).

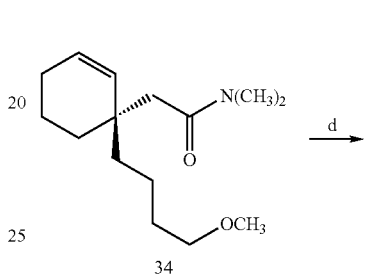

(preferred reagents and conditions for step (d): $BBr_3$ as a Lewis acid, NaI as a nucleophilic reagent, and 15-crown-5 as a catalyst, $CH_2Cl_2$ as a solvent; temperature range from about −40° C. to about −20° C.).

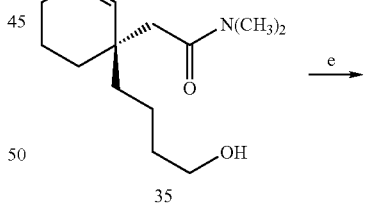

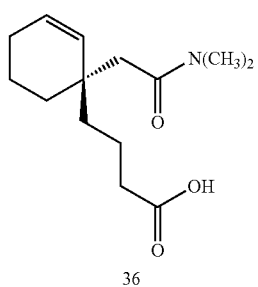

(preferred reagents and conditions for step (e): pyridinium dichromate as an oxidation reagent, DMF as a solvent; temperature range from about 10° C. to about 40° C.).

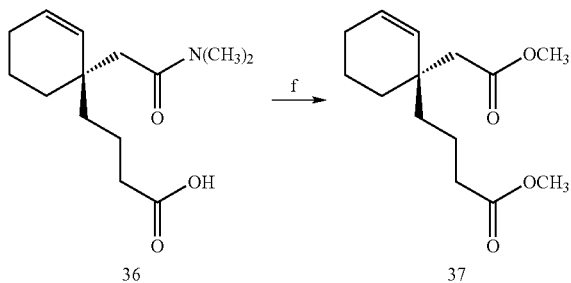

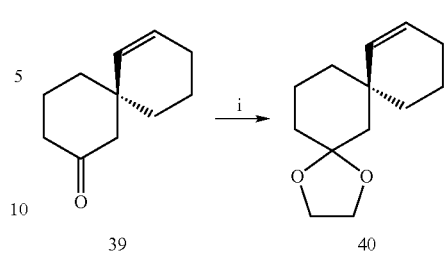

(preferred reagents and conditions for step (f): first (i) KOH, dioxane/water mixture as a solvent, temperature range from about 160° C. to about 240° C.; then (ii) diazomethane (CH$_2$N$_2$), MeOH).

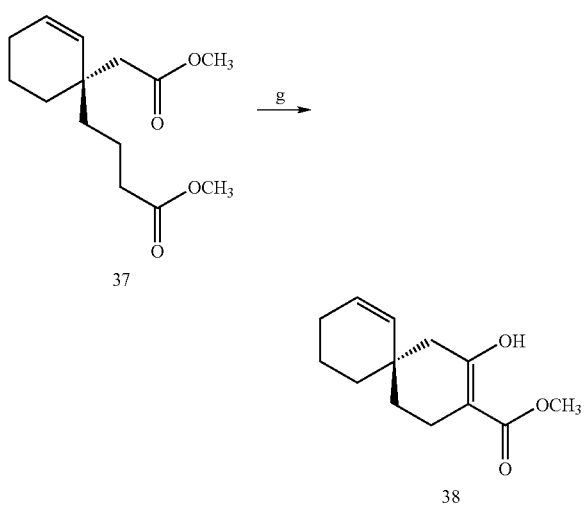

(preferred reagents and conditions for step (g): lithium diisopropylamide as a base, THF as a solvent; temperature range from about −80° C. to about 40° C.).

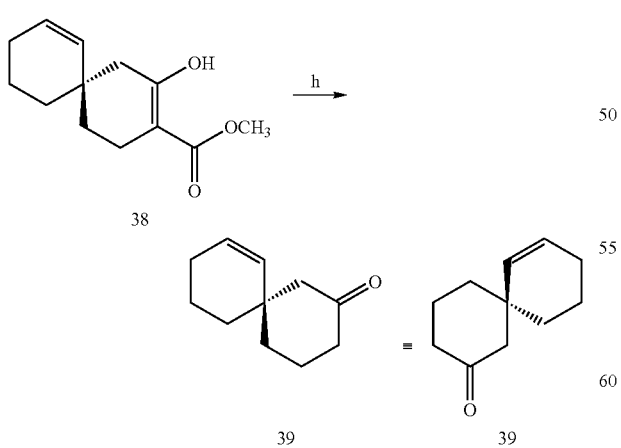

(preferred reagents and conditions for step (h): NaCl, water, and DMSO both as a solvent and an oxidative agent; temperature range from about 140° C. to about 180° C.).

(preferred reagents and conditions for step (i): HOCH$_2$CH$_2$OH as a reagent, p-toluenesulfonic acid as a catalyst, toluene as a solvent; temperature at reflux of the solvent).

In step (j), intermediate 40 obtained in step (i) is submitted to oxidative cleavage by any suitable method, for instance by ozonolysis at low temperature and optionally in the presence of a catalyst. More specifically, said step may be performed in two sub-steps, first including complex formation in the presence of ozone and a solvent, and secondly with use of trimethylphosphite as a reducing agent.

Preferred reagents and conditions for step (j): first (i) O$_3$, methanol as a solvent; temperature about −90° C. to −70° C., more specifically −78° C.; then (ii) P(OCH$_3$)$_3$; temperature ranging from about −78° C. to about −25° C.

In step (k), the 7-(4-oxo-butyl)-1,4-dioxaspiro[4.5]decane-7-carbaldehyde stereoisomer resulting from step (j) is submitted to an aldol condensation preferably in the presence of a suitable solvent and preferably in the presence of an effective amount of a suitable basic catalyst such as, but not limited to, a triflate reagent.

Preferred reagents and conditions for step (k): (PhCH$_2$)$_2$NH$_2$$^+$CF$_3$CO$_2$$^-$ as a catalyst, THF as a solvent; temperature ranging from about 10° C. to about 40° C.

In step (l), the 1,4-dioxa-dispiro[4.1.4.3]tetradec-8-ene-9-carbaldehyde stereoisomer resulting from step (k) is reduced in the presence of a suitable reducing agent such as, but not limited to, hydrogen and in the presence of a suitable solvent and optionally in the presence of an effective amount of a suitable catalyst such as platinum supported onto a carrier:

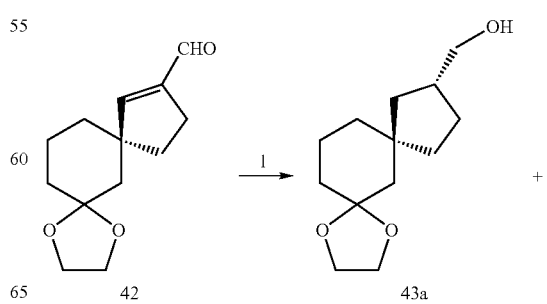

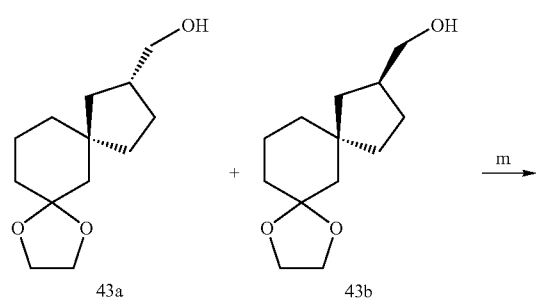

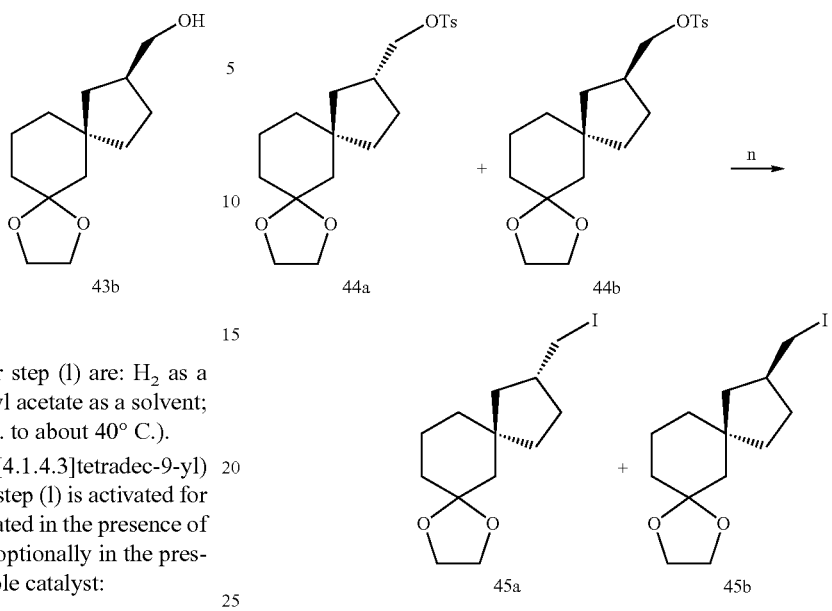

(preferred reagents and conditions for step (l) are: $H_2$ as a reducing agent, Pt/C as a catalyst; ethyl acetate as a solvent; temperature ranging from about 10° C. to about 40° C.).

In step (m), each (1,4-dioxa-dispiro[4.1.4.3]tetradec-9-yl) methanol stereoisomer resulting from step (l) is activated for nucleophilic displacement, e.g. sulfonated in the presence of a sulfonating agent and a solvent and optionally in the presence of an effective amount of a suitable catalyst:

(preferred reagents and conditions for step (n): NaI, $NaHCO_3$, $CH_3CN$ as a solvent; reflux temperature of the solvent; substitution may also be effected with a bromide or a chloride instead of an iodide).

In step (o), the 9-iodomethyl-1,4-dioxa-dispiro[4.1.4.3]tetradec-9-yl methyl ester stereoisomer resulting from step (n) is submitted to a 1,4-addition reaction by means of an α,β-ethylenically unsaturated carboxylic acid ester such as, but not limited to, a $C_1$-$C_8$ alkyl acrylate or $C_1$-$C_8$ alkyl methacrylate, preferably in the presence of a suitable solvent and optionally in the presence of a suitable catalyst:

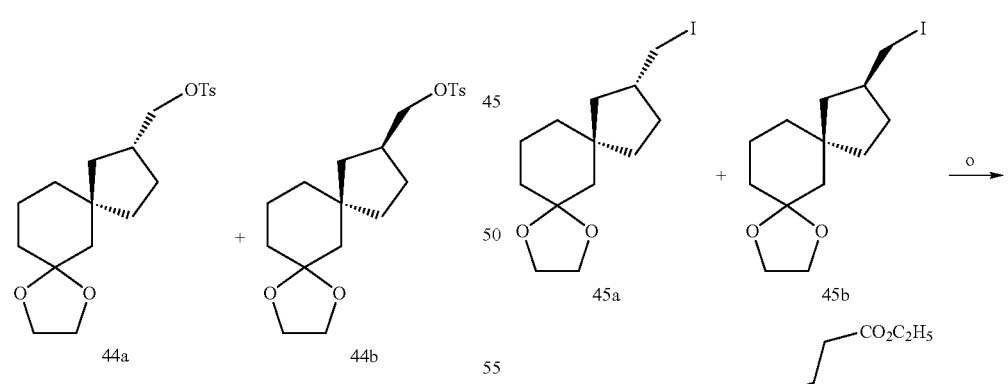

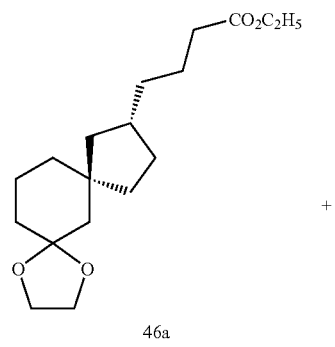

(preferred reagents and conditions for step (m): toluenesulfonyl or methanesulfonyl chloride as a sulfonating agent, dimethylaminopyridine (DMAP) as a catalyst, pyridine as a solvent; temperature ranging from about 10° C. to about 40° C.).

In step (n), the toluene-4-sulfonic acid 1,4-dioxa-dispiro [4.1.4.3]tetradec-9-ylmethyl ester stereoisomer resulting from step (m) is submitted to a halo-de-sulfonyloxy-substitution somewhat similar to a Finkelstein reaction, preferably in the presence of a suitable solvent:

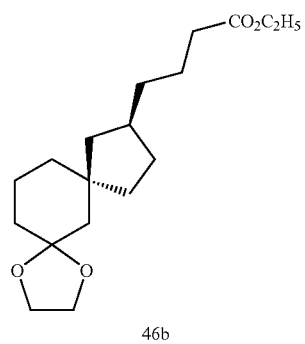

46b (preferred reagents and conditions for step (o): $CH_2=CHCO_2C_2H_5$, Zn and $NiCl_2 \cdot 6H_2O$ as catalyst components, pyridine as a solvent; temperature ranging from about 10° C. to about 40° C.).

In step (p), the 4-(1,4-dioxa-dispiro[4.1.4.3]tetradec-9-yl)-butyric acid ethyl ester stereoisomer resulting from step (o) is alkylated, e.g. by reaction with a suitable organometallic species, preferably a Grignard reagent, preferably in the presence of a suitable solvent:.

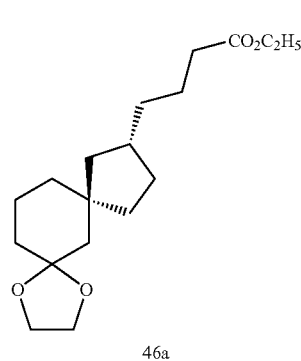

46a

+

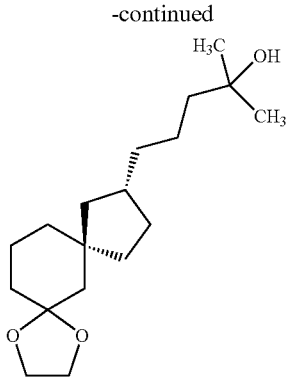

47a

+

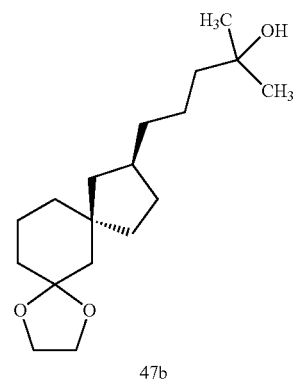

47b (preferred reagents and conditions for step (p): $CH_3MgBr$ as a Grignard reagent, THF as a solvent; temperature ranging from about 0° C. to about 40° C.).

In step (q), the 5-(1,4-dioxa-dispiro[4.1.4.3] tetradec-9-yl)-2-methyl pentanol stereoisomer resulting from step (p) is hydrolysed, preferably under acidic conditions and in the presence of an aqueous solvent:

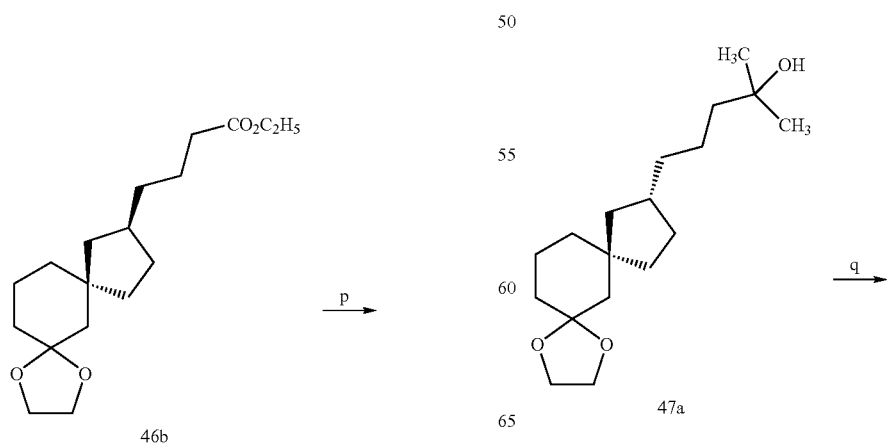

-continued

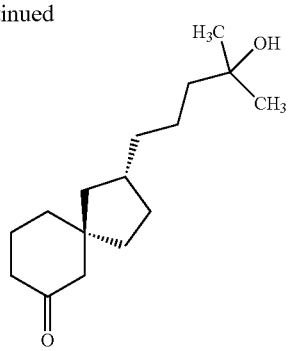
48

(preferred reagents and conditions for step (q): p-toluenesulfonic acid as an acidic catalyst, acetone/water as a solvent medium; temperature ranging from about 0° C. to about 40° C.).

In step (r), an oxygen protecting group (such as described herein above in details) is positioned by using standard procedures well known in the art:

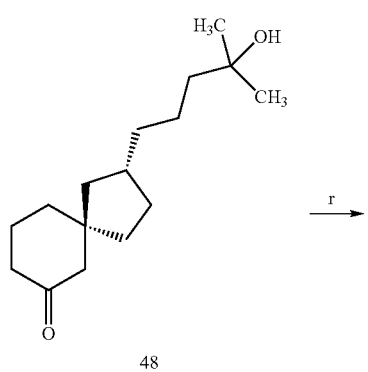

(preferred reagents and conditions for step (r): trimethylsilyl (TMS) ether as a protecting group-containing reagent, THF as a solvent; temperature ranging from about 10° C. to about 40° C.).

In step (s), the 2-(4-methyl-4-trimethylsilanyloxy-pentyl)-spiro[4.5]decan-7-one from step (r) is submitted to a Horner-Wittig reaction involving a phosphine oxide corresponding to the A-ring scaffold of the desired vitamin D₃ analog and wherein hydroxy groups are protected with conventional O-protecting groups (such as described hereinabove), optionally in the presence of an effective amount of a suitable catalyst (preferably an organometallic species derived from an alkaline metal such as, but not limited to, an alkyllithium) and optionally in the presence of a suitable solvent such as an ether:

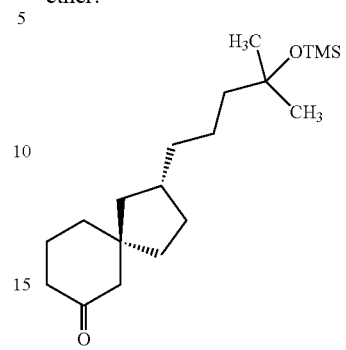

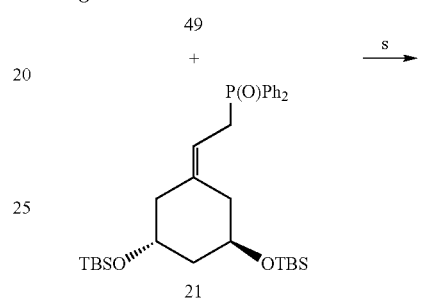

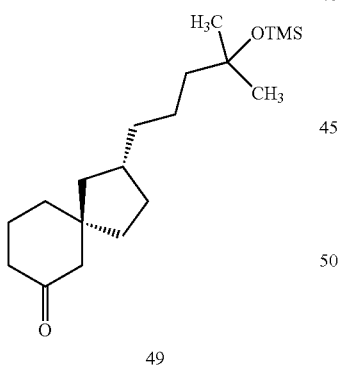
50a

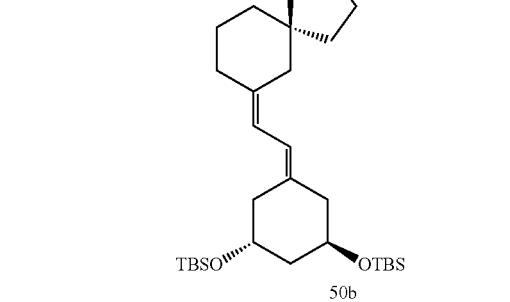
50b (preferred reagents and conditions for step (s) include: 5-[2-(diphenyl-phosphinoyl)-ethylidene]-bis-(tert-butyl-dimethyl-silanyloxy)-cyclohexane as a phosphine oxide reagent, n-BuLi as a catalyst, THF as a solvent; temperature ranging from about 10° C. to about 40° C.).

Then in a last step (t), oxygen deprotection is effected under standard conditions for this kind of reaction:

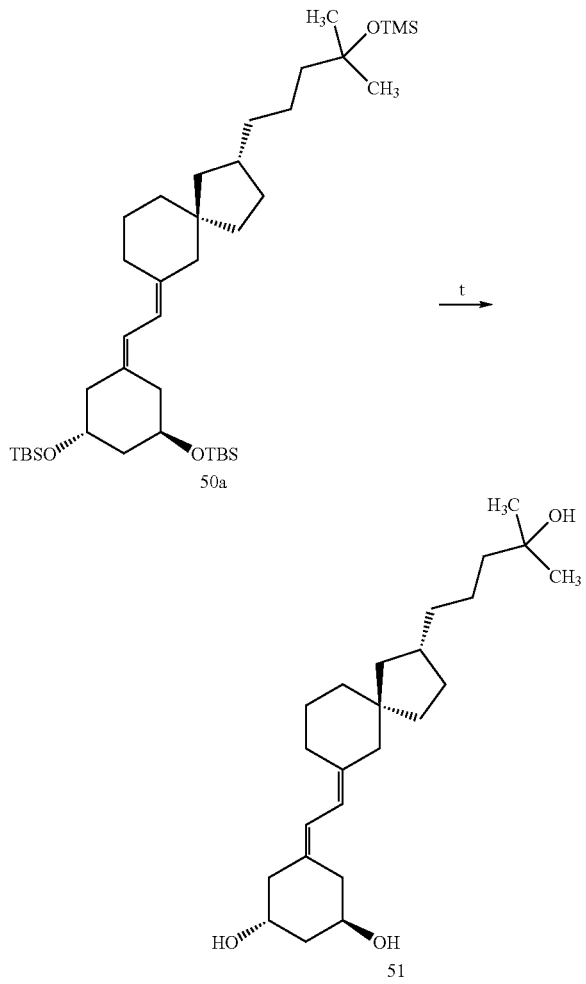

(preferred reagents and conditions for step (t) include: tetrabutylammonium fluoride as a reagent; THF as a solvent; temperature ranging from about 10° C. to about 40° C.).

EXAMPLE 5

Preparation of (1R,3R)-5-{(E)-(2R,5R))-2-[2-(4-hydroxy-4-methylhexyl)-spiro[4.5]dec-7-ylidene]-ethylidene}-cyclohexane-1,3-diol (33')

Preparation of 7-(4-oxo-butyl)-1,4-dioxaspiro[4.5]decane-7-carbaldehyde (12')

Ozone gas was bubbled into a solution of 1,4-dioxa-dispiro[4.1.5.3]pentadec-8-ene, 11', (3.0 g, 14.4 mmol) in MeOH (30 mL) at −78° C. Once the reaction is complete as determined by thin layer chromatography (TLC), argon gas is bubbled through the reaction solution for 10 minutes after which phosphorous acid trimethyl ester (3 mL, 25.4 mmol) is added. The temperature is allowed to rise to −40° C. and stirring continued for an additional 30 min. The solvent is then immediately removed under reduced pressure to afford the desired product which is used without further purification.

Preparation of 1,4-dioxa-dispiro[4.1.4.3]tetradec-8-ene-9-carbaldehyde (13')

To the crude the residue of 7-(4-oxo-butyl)-1,4-dioxaspiro[4.5]decane-7-carbaldehyde, 41, obtained in the previous step described herein above, is added dibenzylammonium trifluoroacetate (0.4 M solution in THF; 12 mL, 4.8 mmol). The resulting mixture is stirred at room temperature for 3 hours after which the solvent is removed in vacuo. The resulting residue is purified over silica (cyclohexane/EtOAc, 8:2) to provide 2.3 g (72% yield) of the desired product as a colorless oil which was characterized as follows:

$R_f$ (isooctane/EtOAc, 7:3) 0.33;

optical rotation at room temperature: +7.3 (c=0.89, $CHCl_3$);

UV (MeOH) absorption at 239 nm;

IR (KBr film): 2939, 2889, 1681, 1618, 1475, 1448, 1363, 1313, 1243, 1213, 1168, 1110, 1063, 1050, 948, 827, and 712 $cm^{-1}$;

$^1$H NMR (500 MHz, $CDCl_3$): 9.75 (1 H, s), 7.00 (1 H, s), 3.91-3.90 (4 H, m), 2.49-2.46 (2 H, m), 1.87 (1 H, ABt, J=13.2, 7.4 Hz), 1.81 (1 H, ABt, J=13.0, 7.0 Hz), 1.74-1.53 (7 H, m), and 1.40 (1 H, m) ppm;

$^{13}$C NMR (75 MHz, $CDCl_3$): 190.9, 160.0, 145.1, 108.7, 64.3, 64.2, 51.1, 44.2, 37.4, 35.8, 34.6, 26.5, 20.9 ppm; and MS m/z (%): 222 ($M^+$, 9), 195 (19), 179 (25), 151 (9),-131 (6), 107 (11), 99 (100), 86 (70), 79 (31), 77 (34), and 55 (33).

Preparation of (1,4-dioxa-dispiro[4.1.4.3]tetradec-9-yl)methanol (14a', 14b')

A mixture of 1,4-dioxa-dispiro[4.1.4.3]tetradec-8-ene-9-carbaldehyde, 42, (3.0 g, 15 mmol) and Pt (5. wt. % on activated carbon; 2.63 g) in EtOAc (70 mL) is placed under $H_2$ (1 atm) and vigorously stirred at room temperature for 36 hours. The mixture is then filtered through Celite and the filtrate concentrated in vacuo to afford an oil which is purified over silica (gradient elution: isooctane/EtOAc, 7:3 to isooctane/EtOAc 1:1) to afford a mixture of epimeric alcohols (2.4 g, 79% yield) which are not separated and which was characterized as follows.

$R_f$ (isooctane/EtOAc, 1:1) 0.31;

IR (KBr film): 3415, 2934, 2867, 1445, 1361, 1318, 1278, 1239, 1171, 1104, 1055, 1040, 948, 856 and 829 $cm^{-1}$;

$^1$H NMR (500 MHz, $CDCl_3$): 3.92-3.90 (4 H, m), 3.55-3.49 (2 H, m), 2.25-2.15 (1 H, m), 1.91 (1 H, dd, J=13.0, 8.5 Hz), 1.83-1.76 (1. H, m), 1.62-1.55 (7 H, m), 1.52-1.47 (1 H, m), 1.37-1.28 (4 H, m) and 1.04 (1 H, dd, J=13.0, 8.8 Hz) ppm;

$^{13}$C NMR (75 MHz, $CDCl_3$): 109.5, 68.0, 64.1, 64.0, 44.9, 64.3, 43.8, 41.7, 41.3, 38.8, 38.1, 35.0, 27.8 and 21.1 ppm;

MS m/z (%) 226 ($M^+$, 3), 195 (9), 183 (99), 165 (3), 121 (4), 113 (9), 99 (100), 86 (23), 79 (10), 67 (8), 55 (23) and 41 (16);

Anal. Calcd for $C_{13}H_{22}O_3$: C, 68.99; H, 9.80. Found: C, 68.85; H, 9.84.

Preparation of toluene-4-sulfonic acid 1,4-dioxa-dispiror[4.1.4.3]tetradec-9-ylmethyl ester (15',25')

To a solution of (1,4-dioxa-dispiro[4.1.4.3]tetradec-9-yl) methanol (14a', 14b') (2.4 g, 11.6 mmol) in dry pyridine (24 mL) at 0° C. is added 4-dimethylamino-pyridine (catalytic amount) and p-toluenesulfonyl chloride (4.08 g, 21.2 mmol). The reaction mixture is stirred at room temperature for 24 hours then poured into a 2 M HCl solution (100 mL). The aqueous solution is extracted with $CH_2Cl_2$ and the combined organic layers are washed with a 2 M HCl solution then saturated $K_2CO_3$ solution. After drying over anhydrous $MgSO_4$, the solvent is removed in vacuo to afford the desired product as a colorless oil which is used without further purification.

Preparation of 9-iodomethyl-1,4-dioxa-dispiro [4.1.4.3]tetradec-9-ylmethyl ester (16',26')

Toluene-4-sulfonic acid 1,4-dioxa-dispiro[4.1.4.3]tetradec-9-ylmethyl ester (44a, 44b) obtained by the procedure described herein above is dissolved in $CH_3CN$ (40 mL). To this solution is added NaI (4.8 g, 32 mmol) and $NaHCO_3$ (catalytic amount) and the reaction mixture is then refluxed for 5 hours. The mixture is allowed to cool to room temperature and the solvent removed in vacuo. The resulting residue is dissolved in $CH_2Cl_2$ (40 mL) and the solution washed with $H_2O$ and dried over anhydrous $MgSO_4$. The solvent is removed in vacuo and the resulting residue is purified over silica (isooctane/EtOAc, 9:1) to afford 2.96 g (83% yield) of the of the epimeric products which are not separated and which was characterized as follows:

$R_f$ (isooctane/EtOAc, 95:5) 0.30;
UV (MeOH) absorption at 254 nm;
IR (KBr film): 2934, 2865, 1444, 1424, 1362, 1317, 1275, 1205, 1182, 1103, 1082, 1057, 946, 836 and 586 cm$^{-1}$;
$^1$H NMR (500 MHz, CDCl$_3$): 3.94-3.89 (4 H, m), 3.23 (1 H, ABd, J=9.3, 6.4 Hz), 3.16 (1 H, ABd, J=9.3, 7.3 Hz), 2.25 (1 H, app. septet, J=7.9 Hz), 2.01 (1 H, dd, J=13.1, 8.1 Hz), 1.91-1.85 (1 H, m), 1.66-1.53 (8 H, m), 1.42-1.25 (3 H, m), and 1.04 (1 H, dd, J=13.1, 9.3 Hz) ppm;
$^{13}$C NMR (125 MHz, CDCl$_3$) 109.4, 64.1, 64.0, 46.0, 45.3, 44.4, 41.7, 39.0, 38.3, 35.0, 32.3, 21.0 and 14.6 ppm;
MS m/z (%): 336 (M$^+$, 3), 293 (42), 209 (38), 99 (100), 86 (22), 79 (11), 55 (21) and 41 (18);
elemental analysis: calc. for $C_{13}H_{21}IO_2$: C, 46.44; H, 6.30; found: C, 46.27; H, 6.41.

Preparation of 4-(1,4-dioxa-dispiro[4.1.4.3]tetradec-9-yl)-butyric acid ethyl ester (17',27')

To a suspension of Zn (powder; 2.9 mg, 44.4 mmol) in dry pyridine (35 mL) is added $CH_2$=$CHCO_2Et$ (4.8 mL, 44.4 mmol) followed by $NiCl_2 \cdot 6H_2O$ (2.54 g, 10.7 mmol) and the reaction mixture is stirred at 65° C. for 2 hours. The mixture is allowed to cool to room temperature and 9-iodomethyl-1,4-dioxa-dispiro[4.1.4.3]tetradec-9-ylmethyl ester, (16',26'), (3.09 g, 8.92 mmol) dissolved dry pyridine (35 mL) is added dropwise and the reaction mixture stirred at room temperature for 3 hours. The mixture is poured into EtOAc (30 mL) and the resulting precipitate removed by filtration through a bed of Celite. The filtrate is collected and washed with a 1 M HCl solution (2×), saturated $NaHCO_3$, and dried over anhydrous $MgSO_4$. The solvent is removed in vacuo and the resulting residue is purified over silica (isooctane/EtOAc, 9:1) to afford 2.3 g (83% yield) of the epimeric pair of the desired products, which are not separated, as a colorless oil which was characterized as follows:

$R_f$ (isooctane/EtOAc, 9:1) 0.23;
IR(KBr film): 2934, 2869, 1737, 1446, 1369, 1246, 1175, 1103, 1056 and 946 cm$^{-1}$;
$^1$H NMR (500 MHz, CDCl$_3$): 4.12 (2 H, q, J=7.1 Hz), 3.91 (4 H, s), 2.27 (1 H, t, J=7.6 Hz), 1.93-1.82 (2 H, m), 1.80-1.74 (1 H, m), 1.64-1.46 (10 H, m), 1.36-1.29 (4 H, m), 1.25 (3 H, t, J=7.1 Hz), 1.19-1.11 (1 H, m) and 0.94-0.91 (1 H, m) ppm;
$^1$C NMR/DEPT (75 MHz, CDCl$_3$): 173.9, 109.6, 64.0, 60.2, 46.1, 46.2, 43.4, 39.0, 38.7, 38.6, 36.3, 35.1, 34.6, 31.5, 24.1, 21.1 and 14.3 ppm;
MS m/z (%): 310 (M$^+$, <1), 267 (56), 195 (3), 167 (3), 151 (3), 113 (9), 99 (100), 86 (22), 55 (18) and 41 (12); and
Anal. Calcd for $C_{18}H_{30}O_4$: C, 69.64; H, 9.74. Found: C, 69.80; H, 9.87.

Preparation of 5-(1,4-dioxa-dispiro[4.1.4.3]tetradec-9-yl)-2-methyl-pentan-2-ol (18',28')

To a solution of 4-(1,4-dioxa-dispiro[4.1.4.3]tetradec-9-yl)-butyric acid ethyl ester (2.28 mg, 7.69 mmol) in dry THF (70 mL) at 0° C. was added dropwise methyl-magnesium bromide (3 M solution in Et$_2$O; 12.8 mL, 38.4 mmol) and the reaction mixture stirred at room temperature for 3 hours. The reaction is quenched by adding a saturated $NH_4Cl$ solution (30 mL), the aqueous layer is then separated and repeatedly extracted with Et$_2$O. The combined organic layers are dried over anhydrous $MgSO_4$ and the solvents removed in vacuo. The resulting residue is purified over silica (isooctane/EtOAc, 8:2) to afford 2.04 g (89% yield) of the desired epimeric alcohols which are then separated over silica (toluene/EtOAc 85:15).

The (R,S) diastereomer 18' was characterized by optical rotation at room temperature: ±11.3.

The (R,R) diastereomer 28' was characterized as follows:
optical rotation at room temperature: −4.8;
$R_f$ (cyclohexane/EtOAc, 8:2) 0.26;
IR (KBr film): 3438, 2932, 2868, 1445, 1362, 1317, 1279, 1173, 1100, 1056, 946, 908, 857 and 836 cm$^{-1}$;
$^1$H NMR (500 MHz, CDCl$_3$): 3.94-3.89 (4 H, m), 1.92-1.85 (2 H, m), 1.79-1.73 (1 H, m), 1.63-1.42 (11 H, m), 1.38-1.24 (6 H, m), 1.20 (6 H, s), 1.17-1.13 (1 H, m) and 0.95-0.88 (1 H, m) ppm;
$^{13}$C NMR (75 MHz, CDCl$_3$): 109.6 , 71.1, 64.0, 45.9 , 45.4, 44.2 , 43.5, 39.0, 38.6., 37.4, 35.1, 31.6, 29.3, 23.5 and 21.2 ppm;
MS m/z (%): 281 (2), 253 (25), 195 (4), 167 (3), 151 (3), 113 (9), 99 (100), 86 (22), 55 (18) and 41 (12).

Preparation of 2-(4-hydroxy-4-methylpentyl)-spiro [4.5]decan-7-one (29')

To a solution of 5-(1,4-dioxa-dispiro[4.1.4.3]tetradec-9-yl)-2-methyl-pentan-2-ol (28') (290 mg, 0.97 mmol) in acetone (6 mL) was added $H_2O$ (catalytic amount) and p-toluenesulfonic acid (catalytic amount). The reaction mixture is stirred at room temperature overnight and then dried over anhydrous $MgSO_4$. The solution is filtered through silica and the filtrate concentrated under reduced pressure. The resulting residue is purified over silica (isooctane/EtOAc, 7:3) to afford the desired product as a colorless oil which was characterized as follows:

R$_f$ (isooctane/EtOAc, 4:6) 0.46;
optical rotation at room temperature: −3.1;
IR (KBr film): 3436, 2934, 2863, 1706, 1460, 1443, 1425, 1376, 1311, 1288, 1228, 1176, 1156, 1078, 1025, 937 and 909 cm$^{-1}$;
$^1$H NMR (500 MHz, CDCl$_3$): 2.30-2.24 (2 H, m), 2.23 (2 H, s), 1.96-1.79 (4 H, m), 1.68-1.64 (3 H, m), 1.53 (1 H, ddd, J=13.9, 9.1, 4.8 Hz), 1.44-1.40 (3 H, m), 1.35-1.25 (5 H, m), 1.22-1.16 (1 H, m), 1.19 (6 H, s) and 0.97 (1 H, dd, J=12.6,10.3 Hz) ppm;
$^{13}$C NMR (75 MHz, CDCl$_3$): 212.1, 70.9, 53.7, 47.3, 45.3 44.1, 41.2, 38.8, 38.2, 38.1, 36.9, 31.4, 29.3, 23.8 and 23.4 ppm;
MS m/z (%): 237 (7), 234 (3), 194 (6), 176 (12), 161 (9), 136 (18), 123 (10), 110 (18), 93 (31), 81 (16), 79 (16), 59 (100), 55 (31), 43 (30) and 41 (30).

Preparation of 2-(4-methyl-4-trimethylsilanyloxy-hexyl)-spiro[4.5]decan-7-one (30')

To a solution of 2-(4-hydroxy-4-methylpentyl)-spiro[4.5]decan-7-one (29') (100 mg, 0.396 mmol) in dry THF (2 mL) is added 1-(trimethylsilyl)imidazole (0.292 mL, 1.98 mmol). The reaction mixture is stirred at room temperature for 4 hours and the solvent removed in vacuo. The resulting residue is purified over silica (petroleum ether/EtOAc, 95:5) to afford the desired product which is used directly for the next reaction step.

Preparation of 5-{(E)-(2R,5R))-2-[2-(4-trimethylsiloxy-4-methylpentyl)-spiro[4.5]dec-7-ylidene]-ethylidene}-1,3-bis(tert-butyldimethylsilyloxy)-cyclohexane (32a')

To a solution of (3R,5R)-{bis(tert-butyldimethylsilyloxy)-cyclohexylidene]ethyl-diphenylphosphine oxide (450 mg, 0.80 mmol) in dry THF (8 mL) was added dropwise n-BuLi (2.5 M solution in hexanes; 0.334 mL, 0.834 mmol) at −78° C. under Ar. The formed dark red solution which forms is stirred at −78° C. for 1 hour and a solution of 2-(5-methyl-5-trimethylsilanyloxy-hexyl)-spiro[4.5]decan-7-one (49) obtained herein above in dry THF (3.5 mL) is added dropwise. The red solution is stirred at −78° C. for 4 hours and then allowed to slowly warm to room temperature. The temperature was allowed to rise to room temperature and the solvent removed in vacuo. The resulting residue was purified over silica (petroleum ether/EtOAc, 95:5) to afford the desired product as a mixture of isomers (32a', 32b') which was used without further purification.

Preparation of (1R,3R)-5-{(E)-(2R,5R))-2-[2-(4-hydroxy-4-methylpentyl)-spiro[4.5]dec-7-ylidene]-ethylidene}-cyclohexane-1,3-diol (33')

To a solution of 5-{(E)-(2R,5R))-2-[2-(4-trimethylsilyloxy-4-methylhexyl)-spiro[4.5]dec-7-ylidene]-ethylidene}-1,3-bis(tert-butyldimethylsilyloxy)-cyclohexane (50a) obtained in the previous step in THF (4 mL) was added n-Bu$_4$NF (1 M solution in THF; 4 mL, 4 mmol). The reaction mixture was stirred at room temperature for 12 hours then loaded onto a silica gel column. The reaction product is eluted (n-pentane/Me$_2$CO) and further purified by HPLC over silica to afford the desired product which was characterizes as follows:
UV (MeOH) absorption at 259, 249, 241 nm;
IR (KBr film): 3360, 2930, 2864, 1612, 1443, 1361, 1218, 1049, 976, 936, 908, 862, 806, 733 cm$^{-1}$;

$^1$H NMR (500 MHz, CDCl$_3$): 6.25 (1 H, A<u>B</u>, J=11.3 Hz), 5.93 (1 H, A<u>B</u>, J=11.3 Hz), 4.09 (2 H, br s), 2.59 (1 H, dd, J=13.4, 3.5 Hz), 2.49 (1 H, dd, J=13.2, 3.7 Hz), 2.35 (1 H, dd, J=13.4, 7.2 Hz), 2.31-2.27 (1 H, m), 2.19-2.11 (2 H, m), 1.98 (2 H, s), 1.90-1.65 (6 H, m), 1.58-1.25 (14 H, m), 1.20 (3 H, s), 1.19 (3 H, s), 1.19-1.11 (1 H, m), and 0.79 (1 H, dd, J=12.4, 10.4 Hz) ppm;
$^{13}$C NMR (75 MHz, CDCl$_3$): 141.9 (C), 131.4 (C), 123.9 (CH), 118.2 (CH), 71.1 (C), 67.5 (CH), 67.2 (CH), 49.6 (CH$_2$), 45.2 (C), 45.0 (CH$_2$), 44.9 (CH$_2$), 44.1 (CH$_2$), 42.2 (CH$_2$), 39.9 (CH$_2$), 38.7 (CH), 37.9 (CH$_2$), 36.9 (CH$_2$), 36.8 (CH$_2$), 31.7 (CH$_2$), 29.3 (CH$_3$), 29.1 (CH$_3$), 28.7 (CH$_2$), 24.6 (CH$_2$), 23.4 (CH$_2$) ppm; and
MS m/z (%): 358 (M$^+$—H$_2$O, 22), 340 (13), 325 (5), 217 (9), 177 (36), 145 (32), 133 (23), 119 (30), 105 (39), 93 (77), 91 (67), 79 (60), 67 (56), 59 (100), 55 (54), 43 (80).

The following is the characterization for (1R,3R)-5-{(Z)-(2R,5R))-2-[2-(4-hydroxy-4-methylpentyl)-spiro[4.5]dec-7-ylidene]-ethylidene}-cyclohexane-1,3-diol (34') having the formula:

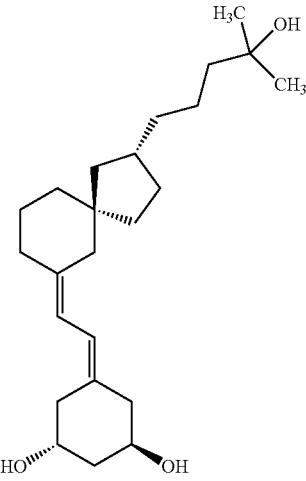

R$_f$ (CH$_2$Cl$_2$/Me$_2$CO, 6:4) 0.35;
UV (MeOH) absorption bands at 259, 249, 242 nm;
IR (KBr film): 3352, 2919, 2857, 1617, 1444, 1360, 1210, 1151, 1049, 976, 932, 906, 810, 737 cm$^{-1}$;
$^1$H NMR (500 MHz, CDCl$_3$): 6.18 (1 H, A<u>B</u>, J=11.2 Hz), 6.07 (1 H, A<u>B</u>, J=11.2 Hz), 4.10 (1 H, br s), 4.06-4.02 (1 H, m), 2.72 (1 H, dd, J=13.1, 3.6 Hz), 2.46 (1 H, dd, J=13.2, 3.0 Hz), 2.23 (1 H, A<u>B</u>, J=13.2 Hz), 2.23-2.17 (2 H, m), 2.13-2.06 (2 H, m), 2.01 (1 H, A<u>B</u>, J=13.2 Hz), 1.96-1.91 (2 H, m), 1.82-1.55 (8 H, m), 1.54-1.23 (10 H, m), 1.20 (3 H, s), 1.19 (3 H, s), 1.19-1.13 (1 H, m), and 0.79 (1 H, dd, J=11.5,11.5 Hz) ppm;

$^{13}$C NMR (75 MHz, CDCl$_3$) 142.2, 131.6, 123.7, 118.3, 71.0, 67.5 67.2, 45.4, 44.6, 44.1, 42.1, 40.8, 39.1, 38.3, 37.4, 36.9, 31.8, 29.3, 29.0, 25.7 and 23.5 ppm; and MS m/z (%): 358 (M$^+$—H$_2$O, 18), 340 (7), 325 (3), 177 (14), 145 (33), 149 (9), 105 (17), 93 (33), 79 (27), 69 (33), 59 (60), 55 (38), 43 (100).

Compounds which are comprised in category VI of the present invention include, but are not limited to, the E-isomers of 5-[2-(2-$R^{2b}$-substituted-spiro[4.5]dec-7-ylidene)-ethylidene]-cyclohexane-1,3-diols having the following structural formula:

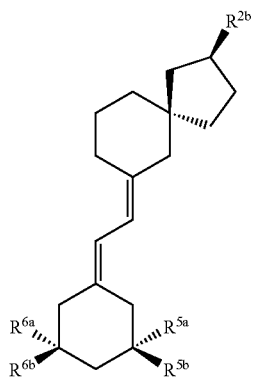

wherein the $R^{2b}$ substitutions are outlined herein below in Table 9.

TABLE 9

| $R^{2b}$ | $R^{5a}$ | $R^{5b}$ | $R^{6a}$ | $R^{6b}$ |
|---|---|---|---|---|
| 4-hydroxy-4-methylpentyl | H | OH | OH | H |
| 5-hydroxy-5-methylhex-2-yl | H | OH | OH | H |
| 6-hydroxy-6-methylhept-2-yl | H | OH | OH | H |
| 5-hydroxy-6-methylhept-2-yl | H | OH | OH | H |
| 1-hydroxy-5,5-dimethylhexyl | H | OH | OH | H |
| 7-hydroxy-7-methyloct-4-en-2-yl | H | OH | OH | H |
| 7-hydroxy-7-ethylnon-4-en-2-yl | H | OH | OH | H |
| 7-hydroxy-7-ethylnon-4-en-2-yl | H | OH | OH | H |
| 7-hydroxy-7-ethylnon-3,5-dien-2-yl | H | OH | OH | H |
| 5-hydroxy-5-methylhex-3-ynyl | H | OH | OH | H |
| 4-(2-methyl-oxyranyl)-but-3-ynyl | H | OH | OH | H |
| 6-hydroxy-6-methylhept-3-yn-2-yl | H | OH | OH | H |
| 5-(2-methyloxyranyl)-pent-4-yn-2-yl | H | OH | OH | H |
| 5-hydroxy-5-ethylhept-3-ynyl | H | OH | OH | H |
| 6-hydroxy-6-ethyloctyn-4-yn-2-yl | H | OH | OH | H |
| 4-hydroxy-4-methylpentyl | OH | H | OH | H |
| 5-hydroxy-5-methylhex-2-yl | OH | H | OH | H |
| 6-hydroxy-6-methylhept-2-yl | OH | H | OH | H |
| 5-hydroxy-6-methylhept-2-yl | OH | H | OH | H |
| 1-hydroxy-5,5-dimethylhexyl | OH | H | OH | H |
| 7-hydroxy-7-methyloct-4-en-2-yl | OH | H | OH | H |
| 7-hydroxy-7-ethylnon-4-en-2-yl | OH | H | OH | H |
| 7-hydroxy-7-ethylnon-4-en-2-yl | OH | H | OH | H |
| 7-hydroxy-7-ethylnon-3,5-dien-2-yl | OH | H | OH | H |
| 5-hydroxy-5-methylhex-3-ynyl | OH | H | OH | H |
| 4-(2-methyl-oxyranyl)-but-3-ynyl | OH | H | OH | H |
| 6-hydroxy-6-methylhept-3-yn-2-yl | OH | H | OH | H |
| 5-(2-methyloxyranyl)-pent-4-yn-2-yl | OH | H | OH | H |
| 5-hydroxy-5-ethylhept-3-ynyl | OH | H | OH | H |
| 6-hydroxy-6-ethyloctyn-4-yn-2-yl | OH | H | OH | H |
| 4-hydroxy-4-methylpentyl | H | OH | H | OH |
| 5-hydroxy-5-methylhex-2-yl | H | OH | H | OH |
| 6-hydroxy-6-methylhept-2-yl | H | OH | H | OH |
| 5-hydroxy-6-methylhept-2-yl | H | OH | H | OH |
| 1-hydroxy-5,5-dimethylhexyl | H | OH | H | OH |
| 7-hydroxy-7-methyloct-4-en-2-yl | H | OH | H | OH |
| 7-hydroxy-7-ethylnon-4-en-2-yl | H | OH | H | OH |
| 7-hydroxy-7-ethylnon-4-en-2-yl | H | OH | H | OH |
| 7-hydroxy-7-ethylnon-3,5-dien-2-yl | H | OH | H | OH |
| 5-hydroxy-5-methylhex-3-ynyl | H | OH | H | OH |
| 4-(2-methyl-oxyranyl)-but-3-ynyl | H | OH | H | OH |
| 6-hydroxy-6-methylhept-3-yn-2-yl | H | OH | H | OH |
| 5-(2-methyloxyranyl)-pent-4-yn-2-yl | H | OH | H | OH |
| 5-hydroxy-5-ethylhept-3-ynyl | H | OH | H | OH |
| 6-hydroxy-6-ethyloctyn-4-yn-2-yl | H | OH | H | OH |

TABLE 9-continued

| $R^{2b}$ | $R^{5a}$ | $R^{5b}$ | $R^{6a}$ | $R^{6b}$ |
|---|---|---|---|---|
| 4-hydroxy-4-methylpentyl | OH | H | H | OH |
| 5-hydroxy-5-methylhex-2-yl | OH | H | H | OH |
| 6-hydroxy-6-methylhept-2-yl | OH | H | H | OH |
| 5-hydroxy-6-methylhept-2-yl | OH | H | H | OH |
| 1-hydroxy-5,5-dimethylhexyl | OH | H | H | OH |
| 7-hydroxy-7-methyloct-4-en-2-yl | OH | H | H | OH |
| 7-hydroxy-7-ethylnon-4-en-2-yl | OH | H | H | OH |
| 7-hydroxy-7-ethylnon-4-en-2-yl | OH | H | H | OH |
| 7-hydroxy-7-ethylnon-3,5-dien-2-yl | OH | H | H | OH |
| 5-hydroxy-5-methylhex-3-ynyl | OH | H | H | OH |
| 4-(2-methyl-oxyranyl)-but-3-ynyl | OH | H | H | OH |
| 6-hydroxy-6-methylhept-3-yn-2-yl | OH | H | H | OH |
| 5-(2-methyloxyranyl)-pent-4-yn-2-yl | OH | H | H | OH |
| 5-hydroxy-5-ethylhept-3-ynyl | OH | H | H | OH |
| 6-hydroxy-6-ethyloctyn-4-yn-2-yl | OH | H | H | OH |

Other compounds which comprise Category VI of the present invention have the structural formula:

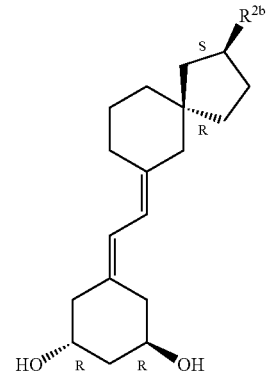

having the assigned (R,S) stereochemistry in the CF-Ring system. Non-limiting examples of $R^{2b}$ are found in Table 10 herein below.

TABLE 10

| No. | $R^{2b}$ |
|---|---|
| 247 | n-hexyl |
| 248 | 1-methylpentyl |
| 249 | 2-methylpentyl |
| 250 | 3-methyl-pentyl |
| 251 | 4-methylpentyl |
| 252 | 1,1-dimethylbutyl |
| 253 | 1,2-dimethylbutyl |
| 254 | 1,3-dimethylbutyl |
| 255 | 2,2-dimethylbutyl |
| 256 | 2,3-dimethylbutyl |
| 257 | 3,3-dimethylbutyl |
| 258 | 1-ethylbutyl |
| 259 | 2-ethylbutyl |
| 260 | n-heptyl |
| 261 | 1-methylhexyl |
| 262 | 2-methyl-hexyl |
| 263 | 3-methylhexyl |
| 264 | 4-methylhexyl |
| 265 | 5-methylhexyl |
| 266 | 1,1-dimethyl-pentyl |
| 267 | 1,2-dimethylpentyl |
| 268 | 1,3-dimethylpentyl |
| 269 | 1,4-dimethylpentyl |
| 270 | 2,2-dimethylpentyl |
| 271 | 2,3-dimethylpentyl |

TABLE 10-continued

| No. | $R^{2b}$ |
|---|---|
| 272 | 4,4-dimethylpentyl |
| 273 | 1-hydroxy-4-methylpentan-1-yl |
| 274 | 2-hydroxy-4-methylpentan-1-yl |
| 275 | 3-hydroxy-4-methylpentan-1-yl |
| 276 | 4-hydroxy-4-methylpentan-1-yl |
| 277 | 1-hydroxy-5-methylhexan-2-yl |
| 278 | 2-hydroxy-5-methylhexan-2-yl |
| 279 | 3-hydroxy-5-methylhexan-2-yl |
| 280 | 4-hydroxy-5-methylhexan-2-yl |
| 281 | 5-hydroxy-5-methylhexan-2-yl |
| 282 | 1-hydroxy-6-methylheptan-2-yl |
| 283 | 2-hydroxy-6-methylheptan-2-yl |
| 284 | 3-hydroxy-6-methylheptan-2-yl |
| 285 | 4-hydroxy-6-methylheptan-2-yl |
| 286 | 5-hydroxy-6-methylheptan-2-yl |
| 287 | 6-hydroxy-6-methylheptan-2-yl |
| 288 | 1-hydroxy-1,5-dimethyl-hexan-1-yl |
| 289 | 1-hydroxy-5,5-dimethyl-hexan-1-yl |
| 290 | 4-methylpent-2-enyl |
| 291 | 5-methylhex-2-enyl |
| 292 | 5-methylhex-3-enyl |
| 293 | 4-ethylhex-2-enyl |
| 294 | 6-methylhept-2-enyl |
| 295 | 6-methylhept-3-enyl |
| 296 | 6-methylhept-4-enyl |
| 297 | 7-methyloct-4-en-2-yl |
| 298 | 6-ethyloct-2-enyl |
| 299 | 6-ethyloct-3-enyl |
| 300 | 6-ethyloct-4-enyl |
| 301 | 4-hydroxy-4-methylpent-2-enyl |
| 302 | 4-cyano-4-methylpent-2-enyl |
| 303 | 5-hydroxy-5-methylhex-2-enyl |
| 304 | 5-hydroxy-5-methylhex-3-enyl |
| 305 | 4-hydroxy-4-ethylhex-2-enyl |
| 306 | 6-hydroxy-6-methylhept-2-enyl |
| 307 | 6-hydroxy-6-methylhept-3-enyl |
| 308 | 6-hydroxy-6-methylhept-4-enyl |
| 309 | 7-hydroxy-7-methyloct-4-en-2-yl |
| 310 | 7-hydroxy-7-methyloct-3,5-dien-2-yl |
| 311 | 6-hydroxy-6-ethyloct-2-enyl |
| 312 | 6-hydroxy-6-ethyloct-3-enyl |
| 313 | 6-hydroxy-6-ethyloct-4-enyl |
| 314 | 7-hydroxy-7-ethylnon-3,5-dien-2-yl |
| 315 | pent-2-ynyl |
| 316 | hex-2-yn-2-yl |
| 317 | hex-3-yn-2-yl |
| 318 | hex-4-yn-2-yl |
| 319 | 5-methylhex-3-ynyl |
| 320 | 6-methylhept-3-yn-2-yl |
| 321 | 5-ethylhept-3-ynyl |
| 322 | 6-ethyloctyn-4-yn-2-yl |
| 323 | 5-hydroxy-5-methylhex-3-ynyl |
| 324 | 4-(2-methyl-oxyranyl)-but-3-ynyl |
| 325 | 6-hydroxy-6-methylhept-3-yn-2-yl |
| 326 | 5-(2-methyl-oxyranyl)-pent-4-yn-2yl |
| 327 | 5-hydroxy-5-ethylhept-3-ynyl |
| 328 | 6-hydroxy-6-ethyloctyn-4-yn-2-yl |

The compounds which comprise Category VI of the present invention can be prepared according to Scheme V herein above utilizing intermediates such as intermediate 18' and 19' prepared and isolated in Example 5 herein above.

The following is the characterization for (1R,3R)-5-{(E)-(2R,5S))-2-[2-(4-hydroxy-4-methylpentyl)-spiro[4.5]dec-7-ylidene]-ethylidene}-cyclohexane-1,3-diol (23') having the formula:

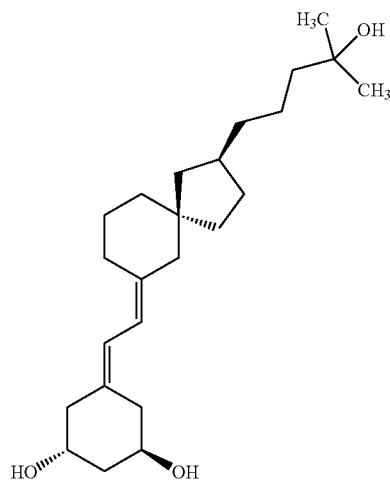

$R_f$ (CH$_2$Cl$_2$/Me$_2$CO, 6:4) 0.37;
UV (MeOH) absorption at 259, 249, and 241 nm;
IR (KBrfilm): 3358, 2929, 2857, 1617, 1443, 1364, 1296, 1216, 1049, 976, 938, 908, 863, 812 and 732 cm$^{-1}$;
$^1$H NMR (500 MHz, CDCl$_3$): 6.24 (1 H, AB, J=11.3 Hz), 5.93 (1 H, AB, J=11.3 Hz), 4.08 (2 H, br s), 2.61 (1 H, dd, J=13.4, 3.6 Hz), 2.49 (1 H, dd, J=13.2, 3.7 Hz), 2.32(1 H, dd, J=13.4, 7.3 Hz), 2.21-2.15(3 H, m), 2.02. (1 H, AB, J=13.3 Hz), 1.99 (1 ), AB, J=13.3 Hz), 1.89-1.81 (3 H, m), 1.78-1.72 (1 H, m), 1.59-1.42 (9 H, m), 1.69 (1 H, br s), 1.35-1.25 (6 H, m), 1.20 (3 H, s), 1.19 (3 H, s), 1.20-1.13 (1 H, m), and 0.93 (1 H, dd, J=12.9, 9.4 Hz) ppm;
$^{13}$C NMR (75 MHz, CDCl$_3$): 141.9, 131.4, 123.9, 117.9, 71.1, 67.5, 67.2, 50.7, 45.2, 45.0, 44.9, 44.2, 42.2, 39.4, 39.0, 38.1, 37.2, 36.9 31.9, 29.4, 29.3, 28.7, 24.4, 23.4 ppm; and
MS m/z (%): 358 (M$^+$—H$_2$O, 18), 340 (19), 217 (3), 177 (17), 145 (17), 105 (26), 93 (44), 79 (50), 59 (68), and 43 (100).

The following is the characterization for (1R,3R)-5-{(Z)-(2R,5S))-2-[2-(4-hydroxy-4-methylpentyl)-spiro[4.5]dec-7-ylidene]-ethylidene}-cyclohexane-1,3-diol (24') having the formula:

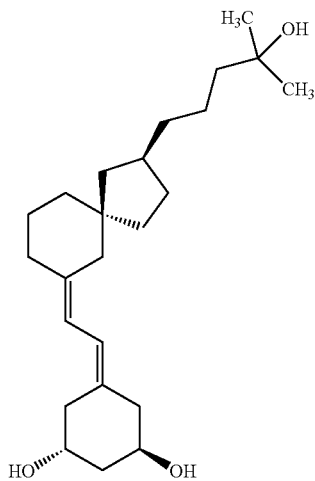

$R_f$ (CH$_2$Cl$_2$/Me$_2$CO, 6:4) 0.36;

UV (MeOH) absorption at 259, 249, 242 nm;

IR (KBr film): 3352, 2919, 2857, 1617, 1444, 1360, 1210, 1151, 1049, 976, 932, 906, 810, 737 cm$^{-1}$;

$^1$H NMR (500 MHz, CDCl$_3$): 6.21 (1 H, AB, J=11.2 Hz), 6.06 (1 H, AB, J=11.2 Hz), 4.09-4.02 (2 H, m), 2.68 (1 H, dd, J=13.3, 3.8 Hz), 2.48 (1 H, dd, J=13.2, 3.5 Hz), 2.26 (1 H, dd, J=13.3, 7.8 Hz), 2.19 (1 H, dd, J=13.2, 6.5 Hz), 2.15 (1 H, AB, J=13.3 Hz), 2.12 (1 H, AB, J=13.3 Hz), 2.09 (2 H, dd, J=6.0, 6.0 Hz), 1.94-1.74 (4 H, m), 1.62 (1 H, dd, J=12.9, 7.9 Hz), 1.57-1.41 (9 H, m), 1.35-1.25 (6 H, m), 1.23-1.17 (1 H, m), 1.21 (3 H, s), 1.20(3 H, s), and 0.93(1 H,dd, J=13.0, 9.3 Hz) ppm;

$^{13}$C NMR/DEPT (75 MHz, CDCl$_3$): 142.2, 131.4, 123.9, 118.0, 71.1, 67.5, 67.3, 45.2, 45.1, 44.9, 44.2, 42.2, 39.4, 39.1, 38.2, 37.3, 37.1, 32.0, 29.4, 29.1, 25.4, 23.4 ppm; and MS m/z (%): 358 (M$^+$—H$_2$O, 51), 340 (40), 217 (10), 145 (26), 91 (56), 79 (48), 69 (55), 55 (49), 43 (100).

Compounds listed and described herein above have been found in many instances to exhibit activities (IC$_{50}$ in the cell based assay described herein below or ones which are referenced herein) at a level below about 1 mM, more specifically 1 micromolar (μM).

Each of the disease states or conditions which the formulator desires to treat may require differing levels or amounts of the compounds described herein to obtain a therapeutic level. The formulator can determine this amount by any of the known testing procedures known to the artisan. It is well known that the effective amount of a compound is predicated on various parameters which are germane to delivery of an effective active ingredient, inter alia, in vivo activity, bioavailability, metabolism, ease of formulation, stability of compound formulation. The artisan of ordinary skill will recognize that a compound having superior properties in vitro may, when introduced into humans or higher mammals, not succeed as the best compound of a Category defined herein above.

Diseases Affected by Cell Proliferation

The compounds described herein have a selective activity on cell function. One key selective action relates to the inhibition of cell proliferation. Non-limiting examples of cells which are a target of cell proliferation inhibition include both non-malignant cells, inter alia, keratinocytes and malignant cells, inter alia, breast carcinoma cells, leukemia cells. A second selective activity on cell function relates to induction of cell differentiation, for example, leukemia cells.

However, unlike current compounds used against diseases relating to cell proliferation, inter alia, classical vitamin D compounds, the compounds of the present invention have a strikingly lower effect on calcium and bone homeostasis. Indeed, as described herein below, 1α,25-dihydroxyvitamin D$_3$ [1α,25(OH)$_2$D$_3$], a Vitamin D metabolite, is used as a control when evaluating the compounds of the present invention. One test utilizing vitamin D repleted normal mice, demonstrated the compounds of the present invention exhibited a lower toxic effect on calcium and bone homeostatsis when measured at key end points, inter alia, calcium levels in serum, urine and the femur; osteocalcin levels in serum, and against body weight.

The following diseases or disease states are affected by successfully controlling, modulating, or inhibiting cell proliferation, cell differentiation or calcium and phosphate or bone homeostasis disorders.

A) Calcium and Phosphate Disorders:

The compounds of the present invention are suitable for use in diseases and conditions which are related to calcium and phosphate metabolism. It has been found that Vitamin D and its metabolites act via nongenomic mechanisms, either by activating ion channels or other membrane related or second messenger signals.[4,5,6] Therefore, Vitamin D and metabolites have potent effects on calcium and phosphate metabolism, and therefore they can be used for prevention and therapy of Vitamin D deficiency and other disorders of plasma and bone mineral homeostasis, inter alia, osteomalacia, osteoporosis, renal osteodystrophy, and disorders of the parathyroid function. It has also been found that Vitamin D and metabolites affect intercellular calcium concentration, and that genomic as well as non-genomic mechanisms are at play in the intestine.

B) Immune Disorders:
  i) For the purposes of the present invention, type (i) immune disorders are auto-immune diseases, inter alia, diabetes mellitus type 1, multiple sclerosis, lupus and lupus like disorders, asthma, glomerulonephritis, and auto-immune throiditis.
  ii) For the purposes of the present invention, type (ii) immune disorders are selective dysfunctions of the immune system, inter alia, Acquired Immune Deficiency Syndrome (AIDS).
  iii) For the purposes of the present invention, type (iii) immune disorders are medically induced immune disorders, inter alla, the body's rejection of foreign tissue due to tissue grafts (e.g. kidney, heart, bone marrow, liver, islets or whole pancreas, and skin).
  iv) For the purposes of the present invention, type (iv) immune disorders are autoimmune and other inflammatory diseases, inter alla, rheumatoid arthritis.
  v) For the purposes of the present invention, type (v) immune disorders are skin disorders. These disorders can be due to any immune system imbalance, inter alia, those characterized by hyperproliferation, inflammation, (auto)immune reactions. Non-limiting examples include psoriasis, dyskeratosis, and acne.

Because of the advantages the present compounds exhibit, inter alla, a lower toxic effect on calcium and bone homeostatsis, the present invention also relates to the use of the compounds described herein in combination with other immuno-modulating drugs known to affect the immune system, inter alia, cyclosporin, FK 506, glucocorticoids, monoclonal antibodies, cytokines, and growth factors.

C) Cell Proliferation Disorders:

The compounds of the present invention are suitable for use in diseases, disease states, and disorders which are due to abnormal cell proliferation. Among these conditions are various types of cancer such as, but not limited to, breast cancer, leukemia, myelo-dysplastic syndromes and lymphomas, squamous cell carcinomas and gastrointestinal cancers, melanomas, and osteosarcoma.

Another advantage related to the cell differentiation capacity of the compounds of the present invention relates to the treatment or prevention of alopecia. The present invention therefore relates to methods of treating alopecia, especially when induced by chemotherapy or irradiation.

The present invention further relates to forms of the present compounds, which under normal human or higher mammalian physiological conditions, release the compounds described herein. One iteration of this aspect includes the pharmaceutically acceptable salts of the analogs described herein.

The term "pharmaceutically acceptable salts" as used herein means the therapeutically active non-toxic salt forms which some of the compounds of the above formulae, including all stereoisomers and embodiments thereof, are able to form. Therefore, the compounds of this invention optionally comprise salts of the compounds herein, especially pharmaceutically acceptable non-toxic salts containing, for example, cations such as, but not limited to, $Na^+$, $Li^+$, $K^+$, $Ca^{2+}$ and $Mg^{2+}$. Such salts may include those derived from the combination of appropriate cations such as alkali and alkaline earth metal ions or ammonium or quaternary ammonium ions with an acid, typically a carboxylic acid, anion moiety. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion.

Included within this definition is any therapeutically active non-toxic addition salt which the compounds of the present invention are able to form with a salt-forming agent. Such addition salts may conveniently be obtained by treating the compounds of the invention with an appropriate salt-forming acid or base. For instance, compounds having basic properties may be converted into the corresponding therapeutically active, non-toxic acid addition salt form by treating the free base form with a suitable amount of an appropiate acid following conventional procedures. Examples of such appropriate salt-forming acids include, for instance, inorganic acids resulting in forming salts such as but not limited to hydrohalides (e.g.hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxy-butanedioic, 2-hydroxy-1,2,3-propanetricarboxylic and cyclohexanesulfamic acids and the like.

Compounds having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylene-diamine, N-methylglucamine, procaine and the like.

Reaction conditions for treating the compounds of this invention with an appropriate salt-forming acid or base are similar to standard conditions involving the same acid or base but different organic compounds with basic or acidic properties, respectively. Preferably, in view of its use in a pharmaceutical composition or in the manufacture of medicament for treating specific diseases, the pharmaceutically acceptable salt will be designed, i.e. the salt-forming acid or base will be selected so as to impart greater water-solubility, lower toxicity, greater stability and/or slower dissolution rate to the pteridine derivative of this invention.

Moreover, as the compounds of the invention may exist in a variety of different forms, the invention is intended to encompass not only forms of these compounds that are in association with counter ions (e.g., dry salts), but also forms that are not in association with counter ions (e.g., aqueous or organic solutions). Furthermore, this term also includes the solvates which the compounds of the above formulae, including all specific stereoisomers and embodiments thereof, as well as their salts (such as above defined), are able to form, such as for example hydrates, alcoholates, solvates with solvents such as acetonitrile, esters, hydrocarbons and the like. Finally, it should be understood that the invention also includes such compounds in their non-ionized, as well as zwitterionic form, and combinations thereof with stoichiometric amounts of water as in hydrates. Also included within the scope of this invention are the salts that certain compounds are able to form with one or more amino acids, especially the naturally-occurring amino acids found as protein components. Suitable amino acids for this purpose typically have a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth metal (for example, magnesium), ammonium and $NX_4^+$ (wherein X preferably is hydrogen or $C_{1-7}$ alkyl). Physiologically acceptable salts of a compound containing a hydroxy group include the anion of said compound in combination with a suitable cation such as $Na^+$ and $NX_4^+$ (wherein X is as above defined). However, salts of acids or bases which are not physiologically acceptable may also find use, for example, in the preparation or purification of a physiologically acceptable compound. All salts, whether or not derived form a physiologically acceptable acid or base, are within the scope of the present invention.

The formulator, for the purposes of compatibility with delivery mode, excipients, and the like, can select one salt form of the present analogs over another since the compounds themselves are the active species which mitigate the disease processes described herein.

Pro-Drug Forms

Another embodiment of this aspect of the invention are the various precursor or "pro-drug" forms of the compounds of the present invention. It may be desirable to formulate the compounds of the present invention in the form of a chemical species which itself is not an agonist of a vitamin D receptor, but instead are forms of the present compounds which when delivered to the body of a human or higher mammal will undergo a chemical reaction catalyzed by the normal function of the body, inter alia, enzymes present in the stomach or in blood serum, said chemical reaction having the effect of releasing a compound as defined herein. The term "pro-drug" thus relates to these species which are converted in vivo to the active pharmaceutical ingredient.

The pro-drugs of the present invention can have any form suitable to the formulator, for example, esters are common pro-drug forms. In the present case, however, the pro-drug may necessarily exist in a form wherein a covalent bond is cleaved by the action of an enzyme present at the target situs. For example, a C—C covalent bond may be selectively cleaved by one or more enzymes at said target situs and, therefore, a pro-drug in a form other than an easily hydrolysable precursor, inter alia, esters, amides, and the like, may be utilized.

For the purposes of the present invention the term "therapeutically suitable pro-drug" is defined herein as "a vitamin D receptor agonist modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome".

Formulations

The present invention also relates to compositions or formulations which comprise the compounds according to the present invention. In general, the compositions of the present invention comprise an effective amount of one or more 7-(2-cyclohexylidene-ethylidene)-spiro[4.5]decane and derivatives thereof according to the present invention which are effective for controlling cell proliferation.

A further category of formulations relates to pharmaceutical compositions, said compositions comprising:
 a) an effective amount of one or more 7-(2-cyclohexylidene-ethylidene)-spiro[4.5]decane and derivatives thereof according to the present invention which are effective for controlling cell proliferation; and
 b) one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency and that its pharmacokinetic properties, as well as the oral bioavailability could be improved.

Another category of formulation according to the present invention relates to compositions or formulations which comprise a precursor or "pro-drug" form of the 7-(2-cyclohexylidene-ethylidene)-spiro[4.5]decanes according to the present invention. For the purposes of the present invention, as it relates to the subject of chemical entities which are converted in vivo to 7-(2-cyclohexylidene-ethylidene)-spiro[4.5]-decanes, the terms "pro-drug," "derivative," and "precursor" are considered to be interchangeable and represent the same concept. In general, these precursor-comprising compositions of the present invention comprise:
 a) an effective amount of one or more derivatives or pro-drug of 7-(2-cyclohexyl-idene-ethylidene)-spiro[4.5]decanes according to the present invention which act to release in vivo the corresponding analog which is effective for controlling cell proliferation; and
 b) one or more excipients.

The terms "effective amount" and "therapeutic amount" as discussed herein above, is typically determined because of a range of factors. For the purposes of the present invention a first aspect of "therapeutic amount" relates to compositions which deliver a compound according to the present invention wherein the plasma level of said compound is from about 0.001 pg/mL, more specifically 1 pg/mL, yet more specifically 1 µg/mL to about 100 mg/mL in humans or higher mammals.

Another category of compositions relates to compositions which wherein said plasma level of said compound is from about 10 ng/mL to about 25 mg/mL in humans or higher mammals.

Administration of the compositions of the present invention can achieve the desired therapeutic amounts in vivo as measured by the plasma level in various ways. It is not necessary to provide the therapeutic amount of compound in a single dose, for example, a single pill. Therefore, the formulator can vary the size of the dosage, and therefore the amount of compound in the compositions. Non-limiting examples of compositions according to the present invention include:
 a) from about 1 pg to about 1000 mg of one or more 7-(2-cyclohexyl-idene-ethylidene)-spiro[4.5]decanes according to the present invention; and
 b) one or more excipient.

Another embodiment according to the present invention relates to the following compositions:
 a) from about 1 ng to about 500 mg of one or more 7-(2-cyclohexyl-idene-ethylidene)-spiro[4.5]decanes according to the present invention; and
 b) one or more excipient.

Another embodiment according to the present invention relates to the following compositions:
 a) from about 1 mg to about 500 mg of one or more 7-(2-cyclohexyl-idene-ethylidene)-spiro[4.5]decanes according to the present invention; and
 b) one or more excipient.

Another embodiment according to the present invention relates to the following compositions:
 a) from about 100 mg to about 500 mg of one or more 7-(2-cyclohexyl-idene-ethylidene)-spiro[4.5]decanes according to the present invention; and
 b) one or more excipient.

Another embodiment according to the present invention relates to the following compositions:
 a) from about 0.01 mg to about 20 mg of one or more 7-(2-cyclohexyl-idene-ethylidene)-spiro[4.5]decanes according to the present invention; and
 b) one or more excipient.

Another embodiment according to the present invention relates to the following compositions:
 a) from about 0.01 mg to about 5 mg of one or more 7-(2-cyclohexyl-idene-ethylidene)-spiro[4.5]decanes according to the present invention; and
 b) one or more excipient.

A further embodiment according to the present invention relates to the following compositions:
 a) from about 0.1 mg to about 1 mg of one or more 7-(2-cyclohexyl-idene-ethylidene)-spiro[4.5]decanes according to the present invention; and
 b) one or more excipient.

In addition, the compositions of the present invention can be administered as frequently as necessary to achieve a therapeutic amount.

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved affect in controlling cellular proliferation.

Method of Use

The present invention also relates to a method for controlling cell proliferation and diseases which are related to cell proliferation. The present invention thus also relates to a method for preventing or treating cell proliferation and diseases which are related to cell proliferation. The present method comprises the step of administering to a human or higher mammal an effective amount of a composition comprising one or more of the 7-(2-cyclohexyl-idene-ethylidene)-spiro[4.5]decanes according to the present invention.

Because the 7-(2-cyclohexyl-idene-ethylidene)-spiro[4.5]decanes according to the present invention of the present invention can be delivered in a manner wherein more than one site of control can be achieved, more than one disease state can be affectively treated at the same time.

A first aspect of the methods for controlling cellular proliferation relate to calcium and phosphate metabolism: plasma and bone mineral homeostasis, such as bone disorders inter alia, osteomalacia, osteoporosis, renal osteodystrophy, and disorders of the parathyroid function.

A second aspect of the methods for controlling cellular proliferation relate to immune disorders, non-limiting examples of which include:

i) auto-immune diseases, inter alia, diabetes mellitus type 1, multiple sclerosis, lupus and lupus like disorders, asthma, glomerulonephritis, and auto-immune thyroiditis;
ii) selective dysfunctions of the immune system, inter alia, Acquired Immune Deficiency Syndrome (AIDS).
iii) medically induced immune disorders, inter alia, the body's rejection of foreign tissue due to tissue grafts (e.g. kidney, heart, bone marrow, liver, islets or whole pancreas, and skin);
iv) skin disorders, inter alia, those characterized by hyperproliferation, inflammation, (auto)immune reactions, examples of which include psoriasis, dyskeratosis, and acne.

A third aspect of the methods for controlling cellular proliferation relate to cell differentiation disorders, non-limiting examples of which include breast cancer, leukemia, myelodysplastic syndromes and lymphomas, squamous cell carcinomas and gastrointestinal cancers, melanomas, and osteosarcoma.

The present invention comprises a method for providing a therapeutic level of a 7-(2-cyclohexyl-idene-ethylidene)-spiro[4.5]decane according to the present invention, said method comprising administering to a human or higher mammal one or more 7-(2-cyclohexyl-idene-ethylidene)-spiro [4.5]decanes described herein.

For the purposes of the present invention the term "an effective amount" as it relates to the amount of one or more 7-(2-cyclohexyl-idene-ethylidene)-spiro[4.5]decanes delivered to a patient in need of treatment, is defined herein as, "an amount of a pharmaceutically active compound which produces the alleviation of symptoms or the suppression of cellular proliferation as measured directly, for example, by a laboratory test or procedure which provides a measure of the active ingredient in plasma, or indirectly, for example, by the ability of the patient not to experience undesirable disease or disease state symptoms." Said symptoms are necessarily dependent upon one or more factors, inter alia, level of cellular proliferation or differentiation activity, age of the patient, degree of disease involvement, other diseases or disease states present, desired outcome (complete cure as in a chronic illness or temporary relief as in an acute illness condition). It is recognized that the compositions of the present invention can be delivered in various dosages and therefore, the effective amount can be determined on a patient by patient basis if necessary.

Procedures

For the purposes of testing compounds according to the present invention $1\alpha,25$-dihydroxyvitamin $D_3$ [$1\alpha,25(OH)_2 D_3$], a Vitamin D metabolite, is used as the control.

Binding Affinity Evaluation

Affinity for Vitamin D Receptor (VDR)

Selected compounds of the present invention are evaluated for their affinity to bind to a Vitamin D receptor versus the active metabolite $1\alpha,25(OH)_2D_3$. The method employed and described herein are used for determining steroid hormone and steroid hormone mimetic binding. Utilizing the tritium labeled analog, $[^3H]1\alpha,25(OH)_2D_3$, the compounds are evaluated for their binding to a high speed supernatant from porcine intestinal mucosa homogenates.

Incubation is performed at 4° C. for 20 hours and the phase separation is obtained by adding dextran-coated charcoal. The relative affinity of the subject compound is then calculated by determining the concentration needed to displace 50% of the $[^3H]1\alpha,25(OH)_2D_3$ from the VDR as compared to the amount of $[^3H]1\alpha,25(OH)_2D_3$ displaced by non-tritium labeled $1\alpha,25(OH)_2D_3$, which is assigned the relative value of 100%.

Affinity for Human Vitamin D Binding Protein (hDBP)

Selected compounds of the present invention are evaluated for their affinity to bind to a Human Vitamin D receptor versus the active metabolite $1\alpha,25(OH)_2D_3$. The method employed and described herein are used for determining steroid hormone and steroid hormone mimetic binding. Utilizing the tritium labeled analog, $[^3H]1\alpha,25(OH)_2D_3$, the compounds are evaluated for their binding to a high speed supernatant from porcine intestinal mucosa homogenates.

An 5 µL solution of $[^3H]1\alpha,25(OH)_2D_3$ together with the compound to be tested, or with $1\alpha,25(OH)_2D_3$ in the case of the control experiment, dissolved in ethanol are added to glass tubes and incubated with hDBP (0.18 µM) made up to a final volume of 1 mL with a solution containing 0.01 M Tris-HCl buffer and 0.154 M NaCl at pH 7.4. The solution is incubated for 3 hours at 4° C. Final phase separation is obtained by adding 0.5 mL of cold destran-coated charcoal. The relative affinity of the subject compound is then calculated by determining the concentration needed to displace 50% of the $[^3H]1\alpha,25(OH)_2D_3$ from the VDR as compared to the amount of $[^3H]1\alpha,25(OH)_2D_3$ displaced by non-tritium labeled $1\alpha,25(OH)_2D_3$, which is assigned the relative value of 100%.

Table V herein below lists the results for several compounds according to the present invention.

TABLE V

| Compound | VDR binding % | hDBP binding % |
|---|---|---|
| 1α,25(OH)$_2$D$_3$ (control) | 100 | 100 |
| (1R,3R)-5-{2-[(2S,5S)-2-(4-hydroxy-4-methyl-pentyl)-spiro[4.5]dec-(7E)-ylidene]-ethylidene}-cyclo-hexane-1,3-diol | 0.7 | 0 |
| (1R,3R)-5-{2-[(2S,5S)-2-(4-Hydroxy-4-methyl-pentyl)-spiro[4.5]dec-(7Z)-ylidene]-ethylidene}-cyclo-hexane-1,3-diol | 0 | 0 |
| (1R,3R)-5-{2-[(2R,5S)-2-(4-Hydroxy-4-methyl-pentyl)-spiro[4.5]dec-(7E)-ylidene]-ethylidene}-cyclo-hexane-1,3-diol | 0.4 | 0 |
| (1R,3R)-5-{2-[(2R,5S)-2-(4-Hydroxy-4-methyl-pentyl)-spiro[4.5]dec-(7Z)-ylidene]-ethylidene}-cyclo-hexane-1,3-diol | 0 | 0 |
| (1R,3R)-5-{2-[(2S,5R)-2-(4-Hydroxy-4-methyl-pentyl)-spiro[4.5]dec-(7E)-ylidene]-ethylidene}-cyclo-hexane-1,3-diol | 0.8 | 3 |
| (1R,3R)-5-{2-[(2S,5R)-2-(4-Hydroxy-4-methyl-pentyl)-spiro[4.5]dec-(7Z)-ylidene]-ethylidene}-cyclo-hexane-1,3-diol | 0.4 | 3 |
| (1R,3R)-5-{2-[(2R,5R)-2-(4-Hydroxy-4-methyl-pentyl)-spiro[4.5]dec-(7E)-ylidene]-ethylidene}-cyclo-hexane-1,3-diol | 10 | 3 |
| (1R,3R)-5-{2-[(2R,5R)-2-(4-Hydroxy-4-methyl-pentyl)-spiro[4.5]dec-(7Z)-ylidene]-ethylidene}-cyclo-hexane-1,3-diol | 0.8 | 3 |

Measurement of Cell Proliferation

Breast Carcinoma Cells: MCF-7

Selected compounds of the present invention are evaluated for their effect on cell proliferation. Malignant MCF-7 cells are cultured in DMEM nutrient mix F12 (HAM) medium which is supplemented with 10% heat inactivated FCS, glutamine (2 mM), penicillin (100 units/mL) and streptomycin (0.1 mg/mL). The cultures are maintained at 37° C. in an atmosphere of humidified air containing 5% $CO_2$. The MCF-7 cells are seeded at approximately $5 \times 10^3$ cells/well in the DMEM modified medium in a 96-well microtiter plate. Each plate has the wells made up to a final volume of 0.2 mL. After 24 hours incubation, the control, 1α,25(OH)$_2$D$_3$, the compound to be tested is added in the appropriate concentration for an incubation period of 72 hours. Finally, 1 μCi of [$^3$H]thymidine is added to each well and the cells are harvested after a further 4 hour incubation period. The cells are harvested with a Parckard Harvester and the cell count measured by a Packard Topcount System.

Promyelocytic Leukemia Cells (HL-60)

Selected compounds of the present invention are evaluated for their effect on cell proliferation. Falcon tissue chambers are seeded with $4 \times 10^4$ cells/cm$^2$ of HL-60 cells using RPMI 1640 medium supplemented with 20% FCS and gentamycin (50 μg/mL) in a final cell volume of 5 mL. The cultures are maintained at 37° C. in an atmosphere of humidified air containing 5% $CO_2$. After 24 hours incubation, the control, 1α,25(OH)$_2$D$_3$, and the compound to be tested are each dissolved in ethanol and added to the cell culture with the final concentration being less than 0.2%. After 4 days, the dishes are shaken to lose adherent cells. The cells are then washed twice in RPMI medium, counted, and then assayed for differentiation markers (NBT reduction assay). Superoxide production is measured as NBT reducing activity as described by Ostrem. V. K et al. *Proc Natl Acad Sci USA,*. 1987 84: 2610-2614. HL-60 cells at $1 \times 10^6$/mL are mixed with an equal volume of freshly prepared solution of phorbol 12-myristate 13-acetate (200 ng/mL) and NBT (2 μg/mL) and incubated for 30 minutes at 37° C. The percentage of cells containing black formazan deposits is determined using a hemacytometer.

Table VI herein below lists the results for several compounds according to the present invention.

TABLE VI

| Compound | HL-60 | MCF-7 |
|---|---|---|
| 1α,25(OH)$_2$D$_3$ (control) | 100 | 100 |
| (1R,3R)-5-{2-[(2S,5S)-2-(4-Hydroxy-4-methyl-pentyl)-spiro[4.5]dec-(7E)-ylidene]-ethylidene}-cyclo-hexane-1,3-diol | 8 | 20 |
| (1R,3R)-5-{2-[(2S,5S)-2-(4-Hydroxy-4-methyl-pentyl)-spiro[4.5]dec-(7Z)-ylidene]-ethylidene}-cyclo-hexane-1,3-diol | 0.5 | 3 |
| (1R,3R)-5-{2-[(2R,5S)-2-(4-Hydroxy-4-methyl-pentyl)-spiro[4.5]dec-(7E)-ylidene]-ethylidene}-cyclo-hexane-1,3-diol | 4 | 9 |
| (1R,3R)-5-{2-[(2R,5S)-2-(4-Hydroxy-4-methyl-pentyl)-spiro[4.5]dec-(7Z)-ylidene]-ethylidene}-cyclo-hexane-1,3-diol | <1 | 4 |
| (1R,3R)-5-{2-[(2S,5R)-2-(4-Hydroxy-4-methyl-pentyl)-spiro[4.5]dec-(7E)-ylidene]-ethylidene}-cyclo-hexane-1,3-diol | 10 | 50 |
| (1R,3R)-5-{2-[(2S,5R)-2-(4-Hydroxy-4-methyl-pentyl)-spiro[4.5]dec-(7Z)-ylidene]-ethylidene}-cyclo-hexane-1,3-diol | 0.9 | 8 |
| (1R,3R)-5-{2-[(2R,5R)-2-(4-Hydroxy-4-methyl-pentyl)-spiro[4.5]dec-(7E)-ylidene]-ethylidene}-cyclo-hexane-1,3-diol | 200 | 450 |
| (1R,3R)-5-{2-[(2R,5R)-2-(4-Hydroxy-4-methyl-pentyl)-spiro[4.5]dec-(7Z)-ylidene]-ethylidene}-cyclo-hexane-1,3-diol | 8 | 75 |

In Vivo Determination of Calcium Levels

Eight weeks old, male NMRI mice were obtained from the Proefdierencentrum of Leuven (Belgium) and fed a vitamin D-replete diet (0.2% calcium, 1% phosphate, 2000 U vitamin D/kg; Hope Farms, Woerden, The Netherlands). Groups of six mice were IP injected daily during 7 consecutive days with different doses of 1α,25(OH)$_2$D$_3$ (0.1, 0.2 and 0.4 μg/kg/day) or analogues. The control group was injected with vehicle (arachis oil). The average weight of each group of 6 mice was determined at the beginning and at the end of the experiment. The following parameters were evaluated: serum calcium and femur calcium. Serum calcium was measured by a microcolorimetric assay (Sigma, St. Louis, Mo.). Femurs were removed and femur calcium content was measured in HCl-dissolved bone ash (obtained by heating for 24 h in an oven at 100° C.), using the same technique as for serum calcium.

A non-limiting example of in vivo testing relates to (1R,3R)-5-{2-[(2R,5R)-2-(4-hydroxy-4-methyl-pentyl)-spiro[4.5]dec-(7E)-ylidene]-ethylidene}-cyclo-hexane-1,3-diol which afforded an estimated serum calcium of 0.5%, as compared with 1α,25(OH)$_2$D$_3$ (control assigned a value of 100%). This compound is therefore approximately 200 times less calcemic than the control. Table VII presents the serum and femur calcium levels in mice after intraperitoneal injections after 7 consecutive days. NMRI mice were injected with vehicle (arachis oil), 1α,25-(OH)$_2$-D$_3$ (0.1, 0.2 or 0.4 μg/kg/d) or the compound according to the present invention (0.4 or 5 or 10 μg/kg/d).

TABLE VII

| Compound | Dose μg/kg/d | Serum Ca mg/dl | Femur Ca mg | Body Weight g |
|---|---|---|---|---|
| Vehicle | — | 11.4 | 10.9 | 31.3 |
| 1α,25(OH)2D3 | 0.1 | 13.3 | 10.9 | 30.5 |
| 1α,25(OH)2D3 | 0.2 | 14.1 | 10.3 | 27.8 |
| 1α,25(OH)2D3 | 0.4 | 18.2 | 8.9 | 23.2 |
| Test compound* | 0.4 | 11.7 | 10.1 | 34.4 |
| Test compound* | 5 | 11.1 | 11.3 | 32.9 |
| Test compound* | 10 | 11.3 | 12.3 | 34.0 |

*(1R,3R)-5-{2-[(2R,5R)-2-(4-Hydroxy-4-methyl-pentyl)-spiro[4.5]dec-(7E)-ylidene]-ethylidene}-cyclo-hexane-1,3-diol

*(1R,3R)-5{2-[(2R,5R)-2-(4-Hydroxy-4-methyl-pentyl)-spiro[4.5]dec-(7E)-ylidene]-ethtylidene}-cyclo-hexane-1,3-diol Measurement of Prevention of Osteoporosis A) Primary Prevention of Osteoporosis by Compound of the Present Invention.

12 Week old $C_3H$ female mice are subjected to bilateral ovariectomy or sham surgery. The animals are treated with a test compound or vehicle by oral gavage or intraperitoneally. Dosing is started 3 days after surgery and continued for 8-9 weeks.

Prior to the first treatment, in vivo measurements are performed to determine bone mineral density (BMD), bone mineral content (BMC) of total body and spine by dual-energy X-ray absorptiometry (DXA). Urine and serum is collected to measure calcium levels together with collagen cross-links in urine and osteocalcin in serum. The animals are weighed regularly during the experimental period. After 4 weeks treatment urine and serum is again collected and biochemical parameters are determined. At the end of the experiment (8-9 weeks) urine is collected and DXA measurement is performed in vivo to determine BMD and BMC. After sacrificing the animals, the tibiae and femora are dissected. The following biochemical parameters are investigated: serum calcium, serum osteocalcin, urine calcium, urine collagen cross-links, femur calcium.

The tibiae are used for histomorphometric analysis and femurs for measurement of cortical and trabecular volumetric density and geometry by peripheral quantitative computed tomography (PQCT) ex vivo.

B) Secondary Prevention of Osteoporosis by Compound of the Present Invention.

12 Week old $C_3H$ female mice are subjected to bilateral ovariectomy or sham surgery. The animals are treated with the analog or vehicle by oral gavage or intraperitoneally. Dosing is started 4 weeks after surgery and continued for 4-10 weeks.

Prior to the first treatment in vivo measurements are performed to determine bone mineral density (BMD), bone mineral content (BMC) of total body and spine by dual-energy X-ray absorptiometry (DXA). Urine and serum is collected to measure calcium levels together with collagen cross-links in urine and osteocalcin in serum. The animals are weighed regularly during the experimental period. After 4 weeks treatment urine and serum is again collected and biochemical parameters are determined and urine is collected and DXA measurement is performed in vivo to determine BMD and BMC. After sacrificing the animals tibiae and femora are dissected. The following biochemical parameters are investigated: serum calcium, serum osteocalcin, urine calcium, urine collagen cross-links, femur calcium.

The tibiae are used for histomorphometric analysis and femurs for measurement of cortical and trabecular volumetric density and geometry by peripheral quantitative computed tomography (PQCT) ex vivo.

The following references relate to various diseases, disease states, and conditions which the compounds of the present invention are effective against:

Wali R. Ket al., J Cell Biochem (2003) 88: 794-801;
Buitrago C. et al. Biochem Biophys Res Commun (2001) 289:1150-1156.
6. Norman A. W. et al. Steroids (2002) 67: 457-466.
7. Bouillon R. et al., Endocr Rev 1995,16, 200-257.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound having the formula:

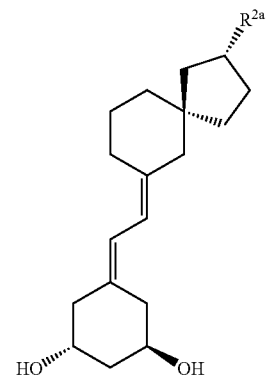

wherein $R^{2a}$ is hydrogen or $C_1$-$C_{20}$ substituted or unsubstituted linear, or branched hydrocarbyl, or C3 to C20 substituted or unsubstituted cyclic hydrocarbyl,
wherein said substitution is chosen from:
i) —$NHCOR^{30}$;
ii) —$COR^{30}$;
iii) —$CO_2R^{30}$;
iv) —$OCOR^{30}$;
v) —$C(=NH)NH_2$;
vi) —$NHC(=NH)NH_2$;
vii) —$N(R^{30})_2$;
viii) —$NHC_6H_5$;
ix) =$CHC_6H_5$;
x) —$CON(R^{30})_2$;
xi) —$CONHNH_2$;
xii) NHCN;
xiii) —OCN;
xiv) —CN;
xv) halogen;
xvi) —$NHN(R^{30})_2$;
xvii) —$OR^{30}$;
xviii) —$NO_2$;
xix) —$CH_mX_n$; wherein X is halogen, m is selected from 0, 1 and 2, n is selected from 0, 1, 2 and 3, and m+n=3;
xx) —$SO_2R^{30}$;
xxi) —$OSO_2R^{30}$;

xxii) —OSO$_3$R$^{30}$;
xxiii) —SO$_2$N(R$^{30}$)$_2$;
xxiv) =O;
xxv) =NR$^{30}$;
xxvi) C$_1$-C$_{20}$ acyclic hydrocarbyl;
xxvii) C$_3$-C$_{20}$ cyclic hydrocarbyl;
xxviii) two hydrogen atoms on adjacent carbon atoms are substituted by a single oxygen atom, thereby forming an epoxy unit; and
xxix) two hydrogen atoms on non-adjacent carbon atoms are substituted to form a C$_3$-C$_{20}$ cyclic hydrocarbyl;

and wherein R$^{30}$ is selected from the group consisting of hydrogen, C$_1$-C$_{10}$ linear or branched alkyl, C$_2$-C$_{10}$ linear or branched alkenyl, C$_2$-C$_{10}$ linear or branched alkynyl, C$_3$-C$_{20}$ heterocyclic, C$_5$-C$_{20}$ heteroaryl and C$_6$-C$_{14}$ aryl.

2. A compound according to claim 1 wherein R$^{2a}$ is unsubstituted C$_1$-C$_{10}$ linear or branched alkyl.

3. A compound according to claim 1 wherein R$^{2a}$ is substituted C$_1$-C$_{20}$ linear or branched alkyl wherein said substitution is chosen from:
  i) —OR$^{30}$;
  ii) halogen;
  iii) —CH$_m$X$_n$; wherein X is halogen, and the index m is 0, 1, or 2; the index n is 1, 2, or 3; and m+n=3; and
  iv) a unit wherein two hydrogens from adjacent carbon atoms are substituted by a single oxygen atom thereby forming an epoxy unit;
  R$^{30}$ is hydrogen, C$_1$-C$_{10}$ linear or branched alkyl, C$_2$-C$_{10}$ linear or branched alkenyl, C$_2$-C$_{10}$ linear or branched alkynyl, and C$_6$ or C$_{10}$ aryl.

4. A compound according to claim 1 wherein R$^{2a}$ is substituted or unsubstituted C$_2$-C$_{20}$ linear or branched alkenyl.

5. A compound having the formula:

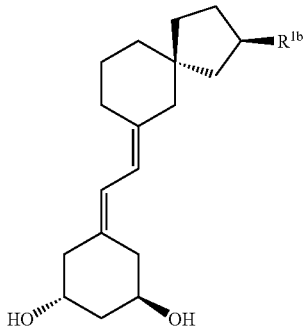

wherein R$^{1b}$ is chosen from:
a) substituted or unsubstituted C$_1$-C$_{10}$ linear or branched alkyl; and
b) substituted or unsubstituted C$_2$-C$_{20}$ linear or branched alkenyl; and
  i) —NHCOR$^{30}$;
  ii) —COR$^{30}$;
  iii) —CO$_2$R$^{30}$;
  iv) —OCOR$^{30}$;
  v) —C(=NH)NH$_2$;
  vi) —NHC(=NH)NH$_2$;
  vii) —N(R$^{30}$)$_2$;
  viii) —NHC$_6$H$_5$;
  ix) =CHC$_6$H$_5$;
  x) —CON(R$^{30}$)$_2$;
  xi) —CONHNH$_2$;
  xii) —NHCN;
  xiii) —OCN;
  xiv) —CN;
  xv) halogen;
  xvi) —NHN(R$^{30}$)$_2$;
  xvii) —OR$^{30}$;
  xviii) —NO$_2$;
  xix) —CH$_m$X$_n$; wherein X is halogen, m+n=3;
  xx) —SO$_2$R$^{30}$;
  xxi) —OSO$_2$R$^{30}$;
  xxii) —OSO$_3$R$^3$;
  xxiii) —SO$_2$N(R$^{30}$)$_2$;
  xxiv) =O; and
  xxv) =NR$^{30}$; and
  wherein R$^{30}$ is selected from the group consisting of hydrogen, C$_1$-C$_{10}$ linear or branched alkyl, C$_2$-C$_{10}$ linear or branched alkenyl, C$_2$-C$_{10}$ linear or branched alkynyl, and C$_6$ or C$_{10}$ aryl.

6. A compound according to claim 5 wherein R$^{1b}$ is chosen from n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, n-heptyl, 1-methylhexyl, 2-methylhexyl, 3-methylhexyl, 4-methylhexyl, 5-methylhexyl, 1,1-dimethyl-pentyl, 1,2-dimethylpentyl, 1,3-dimethyl-pentyl, 1,4-dimethyl-pentyl, 2,2-dimethyl-pentyl, 2,3-dimethyl-pentyl, 4,4-dimethyl-pentyl, 1-hydroxy-4-methylpentan-1-yl, 2-hydroxy-4-methylpentan-1-yl, 3-hydroxy-4-methylpentan-1-yl, 4-hydroxy-4-methylpentan-1-yl, 1-hydroxy-5-methylhexan-2-yl, 2-hydroxy-5-methylhexan-2-yl, 3-hydroxy-5-methylhexan-2-yl, 4-hydroxy-5-methylhexan-2-yl, 5-hydroxy-5-methylhexan-2-yl, 1-hydroxy-6-methylheptan-2-yl, 1-hydroxy-6-methylheptan-2-yl, 2-hydroxy-6-methylheptan-2-yl, 3-hydroxy-6-methylheptan-2-yl, 4-hydroxy-6-methylheptan-2-yl, 5-hydroxy-6-methylheptan-2-yl, 1-hydroxy-1,5-dimethyl-hexan-1-yl, and 1-hydroxy-5,5-dimethyl-hexan-1-yl.

7. A compound according to claim 5 wherein R$^{1b}$ is chosen from 4-methylpent-2-enyl, 5-methylpent-2-enyl, 5-methylpent-3-enyl, 4-ethylhex-2-enyl, 6-methylhept-2-enyl, 6-methylhept-3-enyl, 6-methylhept-4-enyl, 7-methyloct-4-en-2-yl, 6-ethyloct-2-enyl, 6-ethyloct-3-enyl, 6-ethyloct-4-enyl, 4-hydroxy-4-methylpent-2-enyl, 4-cyano-4-methylpent-2-enyl, 5-hydroxy-5-methylhex-2-enyl, 5-hydroxy-5-methylhex-3-enyl, 4-hydroxy-4-ethylhex-2-enyl, 6-hydroxy-6-methylhept-2-enyl, 6-hydroxy-6-methylhept-3-enyl, 6-hydroxy-6-methylhept-4-enyl, 7-hydroxy-7-methyloct-4-en-2-yl, 7-hydroxy-7-methyloct-3,5-dien-2-yl, 6-hydroxy-6-ethyloct-2-enyl, 6-hydroxy-6-ethyloct-3-enyl, 6-hydroxy-6-ethyloct-4-enyl, 7-hydroxy-7-ethylnon-3,5-dien-2-yl, pent-2-ynyl, hex-2-yn-2-yl, hex-3-yn-2-yl, hex-4-yn-2-yl, 5-methylhex-3-ynyl, 5-methylhex-3-ynyl, 5-ethylhept-3-ynyl, 6-ethyloctyn-4-yn-2-yl, 5-hydroxy-5-methylhex-3-ynyl, 4-(2-methyl-oxyranyl)-but-3-ynyl, 6-hydroxy-6-methylhept-3-yn-2-yl, 5-(2-methyl-oxyranyl)-pent-4-yn-2-yl, 5-hydroxy-5-ethylhept-3-ynyl, and 6-hydroxy-6-ethyloctyn-4-yn-2-yl.

8. A compound having the formula:

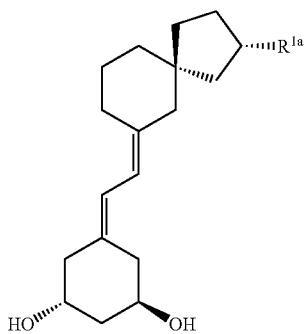

wherein $R^{1a}$ is chosen from:
a) substituted or unsubstituted $C_1$-$C_{10}$ linear or branched alkyl; and
b) substituted or unsubstituted $C_2$-$C_{20}$ linear or branched alkenyl; and
i) —NHCOR$^{30}$;
ii) —COR$^{30}$;
iii) —CO$_2$R$^{30}$;
iv) —OCOR$^{30}$;
v) —C(=NH)NH$_2$;
vi) —NHC(=NH)NH$_2$;
vii) —N(R$^{30}$)$_2$;
viii) —NHC$_6$H$_5$;
ix) =CHC$_6$H$_5$;
x) —CON(R$^{30}$)$_2$;
xi) —CONHNH$_2$;
xii) —NHCN;
xiii) —OCN;
xiv) —CN;
xv) halogen;
xvi) —NHN(R$^{30}$)$_2$;
xvii) —OR$^{30}$;
xviii) —NO$_2$;
xix) —CH$_m$X$_n$; wherein X is halogen, m+n=3;
xx) —SO$_2$R$^{30}$;
xxi) —OSO$_2$R$^{30}$;
xxii) —OSO$_3$R$^3$;
xxiii) —SO$_2$N(R$^{30}$)$_2$;
xxiv) =O; and
xxv) =NR$^{30}$; and
wherein R$^3$ is selected from the group consisting of hydrogen, $C_1$-$C_{10}$ linear or branched alkyl, $C_2$-$C_{10}$ linear or branched alkenyl, $C_2$-$C_{10}$ linear or branched alkynyl, and $C_6$ or $C_{10}$ aryl.

9. A compound according to claim 8 wherein $R^{1a}$ is chosen from n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, n-heptyl, 1-methylhexyl, 2-methylhexyl, 3-methylhexyl, 4-methylhexyl, 5-methylhexyl, 1,1-dimethyl-pentyl, 1,2-dimethyl-pentyl, 1,3-dimethyl-pentyl, 1,4-dimethyl-pentyl, 2,2-dimethyl-pentyl, 2,3-dimethyl-pentyl, 4,4-dimethyl-pentyl, 1-hydroxy-4-methylpentan-1-yl, 2-hydroxy-4-methylpentan-1-yl, 3-hydroxy-4-methylpentan-1-yl, 4-hydroxy-4-methylpentan-1-yl, 1-hydroxy-5-methylhexan-2-yl, 2-hydroxy-5-methylhexan-2-yl, 3-hydroxy-5-methylhexan-2-yl, 4-hydroxy-5-methylhexan-2-yl, 5-hydroxy-5-methylhexan-2-yl, 1-hydroxy-6-methylheptan-2-yl, 1-hydroxy-6-methylheptan-2-yl, 2-hydroxy-6-methylheptan-2-yl, 3-hydroxy-6-methylheptan-2-yl, 4-hydroxy-6-methylheptan-2-yl, 5-hydroxy-6-methylheptan-2-yl, 1-hydroxy-1,5-dimethyl-hexan-1-yl, and 1-hydroxy-5,5-dimethyl-hexan-1-yl.

10. A compound according to claim 8 wherein $R^{1a}$ is chosen from 4-methylpent-2-enyl, 5-methylpent-2-enyl, 5-methylpent-3-enyl, 4-ethylhex-2-enyl, 6-methylhept-2-enyl, 6-methylhept-3-enyl, 6-methylhept-4-enyl, 7-methyloct-4-en-2-yl, 6-ethyloct-2-enyl, 6-ethyloct-3-enyl, 6-ethyloct-4-enyl, 4-hydroxy-4-methylpent-2-enyl, 4-cyano-4-methylpent-2-enyl, 5-hydroxy-5-methylhex-2-enyl, 5-hydroxy-5-methylhex-3-enyl, 4-hydroxy-4-ethylhex-2-enyl, 6-hydroxy-6-methylhept-2-enyl, 6-hydroxy-6-methylhept-3-enyl, 6-hydroxy-6-methylhept-4-enyl, 7-hydroxy-7-methyloct-4-en-2-yl, 7-hydroxy-7-methyloct-3,5-dien-2-yl, 6-hydroxy-6-ethyloct-2-enyl, 6-hydroxy-6-ethyloct-3-enyl, 6-hydroxy-6-ethyloct-4-enyl, 7-hydroxy-7-ethylnon-3,5-dien-2-yl, pent-2-ynyl, hex-2-yn-2-yl, hex-3-yn-2-yl, hex-4-yn-2-yl, 5-methylhex-3-ynyl, 5-methylhex-3-ynyl, 5-ethylhept-3-ynyl, 6-ethyloctyn-4-yn-2-yl, 5-hydroxy-5-methylhex-3-ynyl, 4-(2-methyl-oxyranyl)-but-3-ynyl, 6-hydroxy-6-methylhept-3-yn-2-yl, 5-(2-methyl-oxyranyl)-pent-4-yn-2-yl, 5-hydroxy-5-ethylhept-3-ynyl, and 6-hydroxy-6-ethyloctyn-4-yn-2-yl.

11. A compound according to claim 1
wherein $R^{2a}$ is chosen from:
a) substituted or unsubstituted $C_1$-$C_{10}$ linear or branched alkyl; and
b) substituted or unsubstituted $C_2$-$C_{20}$ linear or branched alkenyl;
wherein said substitution is chosen from:
i) —NHCOR$^{30}$;
ii) —COR$^{30}$;
iii) —CO$_2$R$^{30}$;
iv) —OCOR$^{30}$;
v) —C(=NH)NH$_2$;
vi) —NHC(=NH)NH$_2$;
vii) —N(R$^{30}$)$_2$;
viii) —NHC$_6$H$_5$;
ix) =CHC$_6$H$_5$;
x) —CON(R$^{30}$)$_2$;
xi) —CONHNH$_2$;
xii) —NHCN;
xiii) —OCN;
xiv) —CN;
xv) halogen;
xvi) —NHN(R$^{30}$)$_2$;
xvii) —OR$^{30}$;
xviii) —NO$_2$;
xix) —CH$_m$X$_n$; wherein X is halogen, m+n=3;
xx) —SO$_2$R$^{30}$;
xxi) —OSO$_2$R$^{30}$;
xxii) —OSO$_3$R$^{30}$;
xxiii) —SO$_2$N(R$^{30}$)$_2$;
xxiv) =O; and
xxv) =NR$^{30}$; and
wherein R$^{30}$ is selected from the group consisting of hydrogen, $C_1$-$C_{10}$ linear or branched alkyl, $C_2$-$C_{10}$ linear or branched alkenyl, $C_2$-$C_{10}$ linear or branched alkynyl, and $C_6$ or $C_{10}$ aryl.

12. A compound according to claim 11 wherein $R^{2a}$ is chosen from n-hexyl, 1-methylpentyl, 2-methylpentyl, 3-methyl-pentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, n-heptyl, 1-methylhexyl, 2-methylhexyl, 3-methylhexyl, 4-methylhexyl, 5-methylhexyl, 1,1-dimethyl-pentyl, 1,2-dimethyl-pentyl, 1,3-dimethyl-pentyl, 1,4-dimethyl-pentyl, 2,2-dimethyl-pentyl, 2,3-dimethyl-pentyl, 4,4-dimethyl-pentyl, 1-hydroxy-4-methylpentan-1-yl, 2-hydroxy-4-methylpentan-1-yl, 3-hydroxy-4-methylpentan-1-yl, 4-hydroxy-4-methylpentan-1-yl, 1-hydroxy-5-methylhexan-2-yl, 2-hydroxy-5-methylhexan-2-yl, 3-hydroxy-5-methylhexan-2-yl, 4-hydroxy-5-methylhexan-2-yl, 5-hydroxy-5-methylhexan-2-yl, 1-hydroxy-6-methylheptan-2-yl, 1-hydroxy-6-methylheptan-2-yl, 2-hydroxy-6-methylheptan-2-yl, 3-hydroxy-6-methylheptan-2-yl, 4-hydroxy-6-methylheptan-2-yl, 5-hydroxy-6-methylheptan-2-yl, 1-hydroxy-1,5-dimethyl-hexan-1-yl, and 1-hydroxy-5,5-dimethyl-hexan-1-yl.

13. A compound according to claim 11 wherein $R^{2a}$ is chosen from 4-methylpent-2-enyl, 5-methylpent-2-enyl, 5-methylpent-3-enyl, 4-ethylhex-2-enyl, 6-methylhept-2-enyl, 6-methylhept-3-enyl, 6-methylhept-4-enyl, 7-methyloct-4-en-2-yl, 6-ethyloct-2-enyl, 6-ethyloct-3-enyl, 6-ethyloct-4-enyl, 4-hydroxy-4-methylpent-2-enyl, 4-cyano-4-methylpent-2-enyl, 5-hydroxy-5-methylhex-2-enyl, 5-hydroxy-5-methylhex-3-enyl, 4-hydroxy-4-ethylhex-2-enyl, 6-hydroxy-6-methylhept-2-enyl, 6-hydroxy-6-methylhept-3-enyl, 6-hydroxy-6-methylhept-4-enyl, 7-hydroxy-7-methyloct-4-en-2-yl, 7-hydroxy-7-methyloct-3,5-dien-2-yl, 6-hydroxy-6-ethyloct-2-enyl, 6-hydroxy-6-ethyloct-3-enyl, 6-hydroxy-6-ethyloct-4-enyl, 7-hydroxy-7-ethylnon-3,5-dien-2-yl, pent-2-ynyl, hex-2-yn-2-yl, hex-3-yn-2-yl, hex-4-yn-2-yl, 5-methylhex-3-ynyl, 5-methylhex-3-ynyl, 5-ethylhept-3-ynyl, 6-ethyloctyn-4-yn-2-yl, 5-hydroxy-5-methylhex-3-ynyl, 4-(2-methyl-oxyranyl)-but-3-ynyl, 6-hydroxy-6-methylhept-3-yn-2-yl, 5-(2-methyl-oxyranyl)-pent-4-yn-2-yl, 5-hydroxy-5-ethylhept-3-ynyl, and 6-hydroxy-6-ethyloctyn-4-yn-2-yl.

14. A compound having the formula:

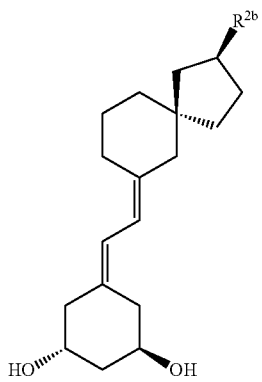

wherein $R^{2b}$ is chosen from:
a) substituted or unsubstituted $C_1$-$C_{10}$ linear or branched alkyl; and
b) substituted or unsubstituted $C_2$-$C_{20}$ linear or branched alkenyl; and
i) —NHCOR$^{30}$;
ii) —COR$^{30}$;
iii) —CO$_2$R$^{30}$;
iv) —OCOR$^{30}$;
v) —C(=NH)NH$_2$;
vi) —NHC(=NH)NH$_2$;
vii) —N(R$^{30}$)$_2$;
viii) —NHC$_6$H$_5$;
ix) =CHC$_6$H$_5$;
x) —CON(R$^{30}$)$_2$;
xi) —CONHNH$_2$;
xii) —NHCN;
xiii) —OCN;
xiv) —CN;
xv) halogen;
xvi) —NHN(R$^{30}$)$_2$;
xvii) —OR$^{30}$;
xviii) —NO$_2$;
xix) —CH$_m$X$_n$; wherein X is halogen, m+n 32 3;
xx) —SO$_2$R$^{30}$;
xxi) —OSO$_2$R$^{30}$;
xxii) —SO$_3$R$^{30}$;
xxiii) —SO$_2$N(R30)$_2$;
xxiv) =O; and
xxv) =NR$^{30}$; and
wherein R$^{30}$ is selected from the group consisting of hydrogen, $C_1$-$C_{10}$ linear or branched alkyl, $C_2$-$C_{10}$ linear or branched alkenyl, $C_2$-$C_{10}$ linear or branched alkynyl, and $C_6$ or $C_{10}$ aryl.

15. A compound according to claim 14 wherein $R^{2b}$ is chosen from n-hexyl, 1-methylpentyl, 2-methylpentyl, 3-methyl-pentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, n-heptyl, 1-methylhexyl, 2-methylhexyl, 3-methylhexyl, 4-methylhexyl, 5-methylhexyl, 1,1-dimethyl-pentyl, 1,2-dimethyl-pentyl, 1,3-dimethyl-pentyl, 1,4-dimethyl-pentyl, 2,2-dimethyl-pentyl, 2,3-dimethyl-pentyl, 4,4-dimethyl-pentyl, 1-hydroxy-4-methylpentan-1-yl, 2-hydroxy-4-methylpentan-1-yl, 3-hydroxy-4-methylpentan-1-yl, 4-hydroxy-4-methylpentan-1-yl, 1-hydroxy-5-methylhexan-2-yl, 2-hydroxy-5-methylhexan-2-yl, 3-hydroxy-5-methylhexan-2-yl, 4-hydroxy-5-methylhexan-2-yl, 5-hydroxy-5-methylhexan-2-yl, 1-hydroxy-6-methylheptan-2-yl, 1-hydroxy-6-methylheptan-2-yl, 2-hydroxy-6-methylheptan-2-yl, 3-hydroxy-6-methylheptan-2-yl, 4-hydroxy-6-methylheptan-2-yl, 5-hydroxy-6-methylheptan-2-yl, 1-hydroxy-1,5-dimethyl-hexan-1-yl, and 1-hydroxy-5,5-dimethyl-hexan-1-yl.

16. A compound according to claim 14 wherein $R^{2b}$ is chosen from 4-methylpent-2-enyl, 5-methylpent-2-enyl, 5-methylpent-3-enyl, 4-ethylhex-2-enyl, 6-methylhept-2-enyl, 6-methylhept-3-enyl, 6-methylhept-4-enyl, 7-methyloct-4-en-2-yl, 6-ethyloct-2-enyl, 6-ethyloct-3-enyl, 6-ethyloct-4-enyl, 4-hydroxy-4-methylpent-2-enyl, 4-cyano-4-methylpent-2-enyl, 5-hydroxy-5-methylhex-2-enyl, 5-hydroxy-5-methylhex-3-enyl, 4-hydroxy-4-ethylhex-2-enyl, 6-hydroxy-6-methylhept-2-enyl, 6-hydroxy-6-methylhept-3-enyl, 6-hydroxy-6-methylhept-4-enyl, 7-hydroxy-7-methyloct-4-en-2-yl, 7-hydroxy-7-methyloct-3,5-dien-2-yl, 6-hydroxy-6-ethyloct-2-enyl, 6-hydroxy-6-ethyloct-3-enyl, 6-hydroxy-6-ethyloct-4-enyl, 7-hydroxy-7-ethylnon-3,5-dien-2-yl, pent-2-ynyl, hex-2-yn-2-yl, hex-3-yn-2-yl, hex-4-yn-2-yl, 5-methylhex-3-ynyl, 5-methylhex-3-ynyl, 5-ethylhept-3-ynyl, 6-ethyloctyn-4-yn-2-yl, 5-hydroxy-5-methylhex-3-ynyl, 4-(2-methyl-oxyranyl)-but-3-ynyl, 6-hydroxy-6-methylhept-3-yn-2-yl, 5-(2-methyl-oxyranyl)-pent-4-yn-2-yl, 5-hydroxy-5-ethylhept-3-ynyl, and 6-hydroxy-6-ethyloctyn-4-yn-2-yl.

17. A composition comprising:
a) a compound according to claim 1 in an amount effective for controlling osteoporosis; and
b) one or more excipients.

18. A composition comprising:
 a) from about 0.001 mg to about 1000 mg of a compound according to claim 1; and
 b) one or more excipients.

19. A method of treating osteoporosis comprising administering to a human or higher mammal an effective amount of a compound according to claim 1.

20. A method of treating osteoporosis comprising administering to a human or higher mammal a composition comprising:
 a) a compound according to claim 1 in an amount effective for controlling osteoporosis; and
 b) one or more excipients.

21. A method of treating osteoporosis comprising administering to a human or higher mammal a composition comprising:
 a) from about 0.001 mg to about 1000 mg of a compound according to claim 1; and
 b) one or more excipients.

* * * * *

UNITED STATES PATENT AND TRADEMARK OFFICE
CERTIFICATE OF CORRECTION

PATENT NO. : 7,888,338 B2
APPLICATION NO. : 11/295000
DATED : February 15, 2011
INVENTOR(S) : Bouillon et al.

It is certified that error appears in the above-identified patent and that said Letters Patent is hereby corrected as shown below:

Column 1, Lines 36-37, replace "thyroidis" with --thyroiditis--.

Column 4, Lines 30-31, replace "n8-hydroxy-quinolinyl" with --8-hydroxy-quinolinyl--.

Column 5, Line 29, replace "suchas" with --such as--;

Line 44, replace "is a substituted $C_8$ alkyl unit," with --is a "substituted $C_8$ alkyl unit,"--.

Column 14, Line 56, replace "($C_9$)," with --($C_9$),--.

Column 19, Lines 16-17, replace "1,4-trifluoromethyl-6-methyl-heptan-2-yl" with
    --1-trifluoromethyl-6-methyl-heptan-2-yl--.

Column 34, Line 27, replace "isomer 3")" with --isomer 3')--.

Column 47, Line 43-44, replace "2-(4-hydroxy-4-methylpentyl)-spiro[4.51]decan-7-one" with
    --2-(4-hydroxy-4-methylpentyl)-spiro[4.5]decan-7-one--.

Column 48, Line 47, replace "(1 4a)" with --(14a)--.

Column 49, Line 18, replace "(9) (100)," with --(9), 99 (100), --.

Column 53, Lines 39-40, replace "speciesderived" with --species derived--.

Column 57, Lines 25-28, replace "(1R, 3R)-5-{2-[(2R,5S)-2-(4-
    hydroxy-4-methyl-pentyl)spiro[4.5]dec-(7E)-ylidenel]-
    ethylidene}-cyclo-hexane-1,3-diol" with --(1R,3R)-5-{2-
    [(2R, 5S)-2-(4-hydroxy-4-methyl-pentyl)spiro[4.5]dec-(7E)-
    ylidene]-ethylidene}-cyclo-hexane-1,3-diol--.

Signed and Sealed this
Twentieth Day of December, 2011

David J. Kappos
*Director of the United States Patent and Trademark Office*

CERTIFICATE OF CORRECTION (continued)

U.S. Pat. No. 7,888,338 B2

Column 60, Line 14, replace "sponding" with --corresponding--.

Column 72, Line 34, replace "and 1.43" with --and 14.3--.

Column 80, Line 39, replace "nucleophic" with --nucleophilic--.

Column 90, Line 33, replace "(9),-131" with --(9), 131--.

Column 98, Line 30, replace "(1 ), A$\underline{B}$, J=13.3 Hz)" with --(1H, A$\underline{B}$, J=13.3 Hz)--.

Column 99, Line 60, replace "homeostatsis" with --homeostasis--.

Column 100, Line 30, replace "inter alla" with --inter alia--;

Line 43, replace "inter alla" with --inter alia--;

Lines 43-44, replace "homeostatsis" with --homeostasis--.

Column 101, Line 32, replace "appropiate" with --appropriate--.

Column 102, Line 45, replace "derived form a" with --derived from a--.

Column 109, Lines 15-18, delete "*(1R,3R)-5{2-[(2R,5R)-2-(4-Hydroxy-4-methyl-pentyl)-spiro[4.5]dec-(7E)-ylidene]-ethtylidene}-cyclo-hexane-1,3-diol";

Line 47, replace "(PQCT)" with --(pQCT)--.

Column 110, Line 6, replace "(PQCT)" with --(pQCT)--.

Column 111, Lines 53-54, replace "b) substituted or unsubstituted $C_2$-$C_{20}$ linear or branched alkenyl; and" with --b) substituted or unsubstituted $C_2$-$C_{20}$ linear or branched alkenyl; and wherein said substitution is chosen from:--.

Column 113, Lines 21-22, replace "b) substituted or unsubstituted $C_2$-$C_{20}$ linear or branched alkenyl; and" with --b) substituted or unsubstituted $C_2$-$C_{20}$ linear or branched alkenyl; and wherein said substitution is chosen from:--.

Column 115, Lines 54-55, replace "b) substituted or unsubstituted $C_2$-$C_{20}$ linear or branched alkenyl; and" with --b) substituted or unsubstituted $C_2$-$C_{20}$ linear or branched alkenyl; and wherein said substitution is chosen from:--.